US012661098B2

(12) United States Patent
Goetz et al.

(10) Patent No.: US 12,661,098 B2
(45) Date of Patent: Jun. 23, 2026

(54) MEDICAL APPARATUS AND METHOD FOR CLOSING AN APERTURE IN A TISSUE

(71) Applicant: Venock Medical GmbH, Regensburg (DE)

(72) Inventors: Wolfgang Goetz, Regensburg (DE); Terrence G Barnes, Munich (DE)

(73) Assignee: VENOCK MEDICAL GMBH, Regensburg (DE)

( * ) Notice: Subject to any disclaimer, the term of this patent is extended or adjusted under 35 U.S.C. 154(b) by 1135 days.

(21) Appl. No.: 17/638,171

(22) PCT Filed: Aug. 26, 2020

(86) PCT No.: PCT/EP2020/073907
§ 371 (c)(1),
(2) Date: Feb. 24, 2022

(87) PCT Pub. No.: WO2021/037943
PCT Pub. Date: Mar. 4, 2021

(65) Prior Publication Data
US 2022/0296223 A1     Sep. 22, 2022

(30) Foreign Application Priority Data

Aug. 26, 2019     (EP) ..................................... 19193644
Apr. 21, 2020     (EP) ..................................... 20170612

(51) Int. Cl.
*A61B 17/064*          (2006.01)
*A61B 17/00*           (2006.01)
(Continued)

(52) U.S. Cl.
CPC ...... *A61B 17/0057* (2013.01); *A61B 17/0644* (2013.01); *A61B 17/0682* (2013.01);
(Continued)

(58) Field of Classification Search
CPC ... A61B 17/0057; A61B 17/08; A61B 17/083; A61B 17/10; A61B 2017/081
See application file for complete search history.

(56) References Cited

U.S. PATENT DOCUMENTS

| | | | |
|---|---|---|---|
| 4,217,902 A | 8/1980 | March | |
| 5,674,231 A | 10/1997 | Green et al. | |

(Continued)

FOREIGN PATENT DOCUMENTS

| | | | |
|---|---|---|---|
| AU | 2010227037 B2 | 4/2015 | |
| CA | 2188210 C | 3/2006 | |

(Continued)

OTHER PUBLICATIONS

International Search Report and Written Opinion from corresponding PCT application PCT/EP2020/073907 dated Mar. 4, 2021.

(Continued)

*Primary Examiner* — Diane D Yabut
(74) *Attorney, Agent, or Firm* — Aird & McBurney LP

(57) ABSTRACT

The present invention relates to a medical apparatus for closing an aperture, an incision, a puncture, a passage through tissue and/or a communication with a blood vessel or other body lumen (short: aperture) of a tissue of a patient, the medical apparatus comprising a closing device holder, for releasably receiving one or more closing devices; and a retracting unit to come into contact with opposite sides of the aperture and for retracting them and/or for spreading the aperture causing it to change its shape into a slit or a slit-like or a more slit-like aperture or to spread or to augment the dimension or diameter of the aperture in at least one or in exactly one dimension of the aperture.

25 Claims, 53 Drawing Sheets

(51) Int. Cl.
    *A61B 17/068*           (2006.01)
    *A61B 17/08*            (2006.01)

(52) U.S. Cl.
    CPC .............. *A61B 2017/00668* (2013.01); *A61B 2017/00862* (2013.01); *A61B 2017/00867* (2013.01); *A61B 2017/0645* (2013.01); *A61B 2017/0649* (2013.01); *A61B 2017/081* (2013.01)

(56) References Cited

U.S. PATENT DOCUMENTS

| | | | |
|---|---|---|---|
| 5,766,189 A | 6/1998 | Matsuno | |
| 5,964,782 A | 10/1999 | Lafontaine et al. | |
| 6,287,322 B1 * | 9/2001 | Zhu ........................ | A61B 17/08 606/139 |
| 6,358,258 B1 | 3/2002 | Arcia et al. | |
| 6,391,048 B1 | 5/2002 | Ginn et al. | |
| 6,533,762 B2 | 3/2003 | Kanner et al. | |
| 6,726,704 B1 | 4/2004 | Loshakove et al. | |
| 6,749,622 B2 | 6/2004 | Mcguckin, Jr. et al. | |
| 6,767,356 B2 | 7/2004 | Kanner et al. | |
| 7,628,306 B2 | 12/2009 | Spurchise et al. | |
| 7,740,640 B2 | 6/2010 | Ginn | |
| 7,744,610 B2 | 6/2010 | Hausen | |
| 7,875,053 B2 | 1/2011 | Bender et al. | |
| 7,942,301 B2 | 5/2011 | Sater | |
| 8,282,654 B2 | 10/2012 | Ferrari et al. | |
| 8,317,807 B1 | 11/2012 | Post | |
| 8,545,974 B2 | 10/2013 | Creasy, Jr. | |
| 8,758,398 B2 | 6/2014 | Carley | |
| 8,932,324 B2 | 1/2015 | Sibbitt, Jr. et al. | |
| 9,585,647 B2 | 3/2017 | Clark | |
| 9,668,724 B2 | 6/2017 | Tang et al. | |
| 9,980,728 B2 | 5/2018 | Cummins et al. | |
| 10,111,664 B2 | 10/2018 | Ginn et al. | |
| 10,143,460 B2 | 12/2018 | Green | |
| 2001/0053922 A1 | 12/2001 | Zhu et al. | |
| 2002/0107542 A1 | 8/2002 | Kanner et al. | |
| 2002/0133193 A1 | 9/2002 | Ginn et al. | |
| 2003/0045893 A1 | 3/2003 | Ginn | |
| 2005/0059985 A1 | 3/2005 | Kimura | |
| 2006/0282118 A1 | 12/2006 | Surti | |
| 2007/0049967 A1 | 3/2007 | Sibbitt et al. | |
| 2007/0049968 A1 | 3/2007 | Sibbitt et al. | |
| 2008/0221599 A1 | 9/2008 | Starksen | |
| 2008/0221614 A1 | 9/2008 | Mas | |
| 2008/0300628 A1 | 12/2008 | Ellingwood | |
| 2008/0312666 A1 | 12/2008 | Ellingwood et al. | |
| 2008/0319455 A1 * | 12/2008 | Harris ................ | A61B 17/0684 606/139 |
| 2009/0039138 A1 | 2/2009 | Bender et al. | |
| 2009/0048665 A1 | 2/2009 | Miron et al. | |
| 2009/0259249 A1 | 10/2009 | Lobello | |
| 2010/0160958 A1 | 6/2010 | Clark | |
| 2010/0228286 A1 | 9/2010 | Ginn | |
| 2011/0054521 A1 | 3/2011 | Ventura et al. | |
| 2012/0209318 A1 | 8/2012 | Qadeer | |
| 2012/0226308 A1 | 9/2012 | Martin et al. | |
| 2015/0039008 A1 | 2/2015 | Suzuki et al. | |
| 2015/0066055 A1 | 3/2015 | Sibbitt, Jr. et al. | |
| 2017/0049426 A1 | 2/2017 | Gianotti et al. | |
| 2018/0085101 A1 * | 3/2018 | Flanagan ................ | A61B 17/30 |
| 2018/0193600 A1 | 7/2018 | Kassab et al. | |
| 2018/0256139 A1 | 9/2018 | Miller et al. | |
| 2018/0256166 A1 | 9/2018 | Cummins et al. | |

FOREIGN PATENT DOCUMENTS

| | | |
|---|---|---|
| CN | 201668444 U | 12/2010 |
| CN | 111836585 A | 10/2020 |
| DE | 29923269 U1 | 8/2000 |
| EP | 0681811 A2 | 11/1995 |
| JP | 2003518975 A | 6/2003 |
| JP | 2008505697 A | 2/2008 |
| WO | 2007025018 A2 | 3/2007 |
| WO | 2007025019 A2 | 3/2007 |
| WO | 2007099448 A2 | 9/2007 |
| WO | 2008150915 A1 | 12/2008 |
| WO | 2010081103 A1 | 7/2010 |
| WO | 2019135236 A1 | 7/2019 |
| WO | 2019166573 A1 | 9/2019 |

OTHER PUBLICATIONS

English Translation of DE29923269 from ESPACENET dated Feb. 23, 2022.
European Search Report from corresponding EP Application No. EP19193644 dated Feb. 4, 2020.
English Translation of CN 201668444U from Google Patent dated Feb. 23, 2022.

* cited by examiner

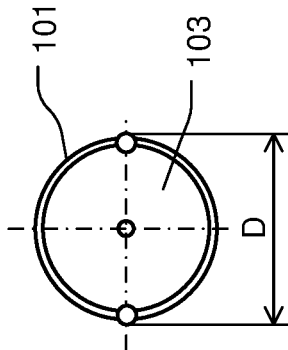
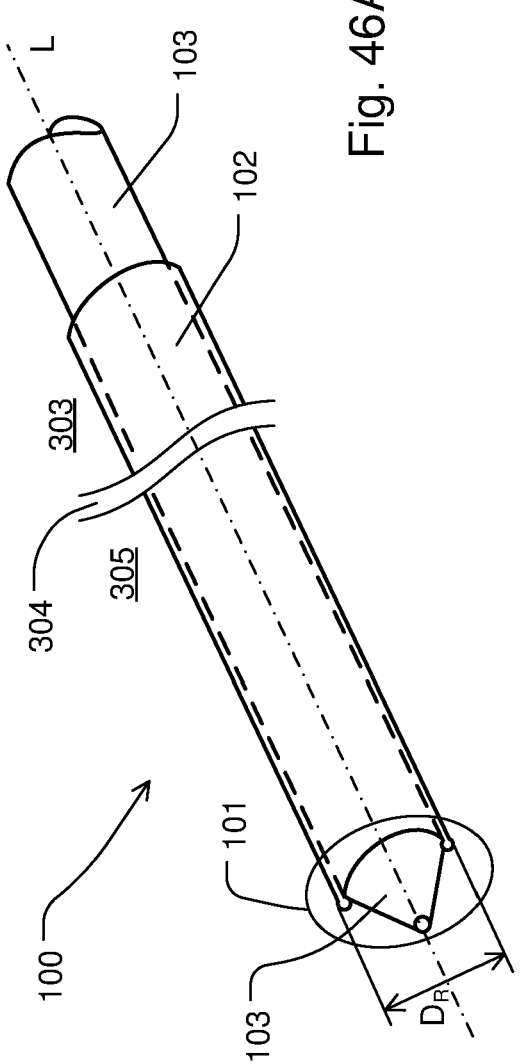
Fig. 46A
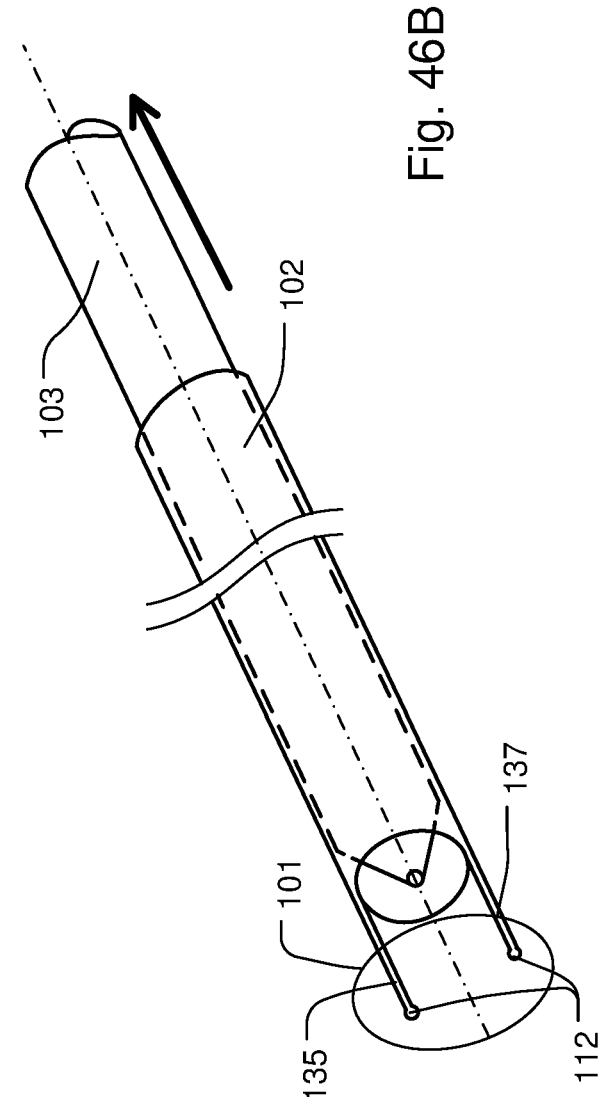
Fig. 46B

102

103

103

$D_N$

101

$D_N$

103

L

139

139

103

139

102

L $D_N$

101

MEDICAL APPARATUS AND METHOD FOR CLOSING AN APERTURE IN A TISSUE

FIELD OF THE INVENTION

The present invention relates to a medical apparatus for closing an aperture or opening and a method for closing an aperture. It also relates to a closing device.

The present invention relates generally to a medical apparatus (in short: apparatus) and methods for engaging tissue and/or closing openings through tissue, and more particular for closing apertures in a blood vessel or other body lumen, which is an alternative to suturing; and, more particularly, relates to a closure apparatus having applications for closure of openings in body organs or blood vessel walls, in particular after invasive procedures in a patient's system, and corresponding methods of use.

BACKGROUND OF THE INVENTION

There exist several interventional procedures which are generally performed by puncture and inserting a hollow needle in a blood vessel or other body organ, a guide wire may then be advanced through the needle lumen into the patient's blood vessel or other organs. The guide-wire may be advanced through the needle and the needle may be removed and an introducer casing may be advanced over the guide wire into the vessel or other body organ (Seldinger technique). Such casings are generally flexible tubes having thin walls and diameters matching the needs of the utilized treatment system in the range of up to about 30 F or more. The proximal end of the casing is retained outside of the skin of the patient, commonly utilized with a hemostatic valve to prevent blood flow from the blood vessel through the casing. A catheter or other device may then be advanced through a lumen of the introducer casing and over the guide-wire into a position for performing a medical procedure. The punctures are utilized for a number of reasons including, but not limited to, diagnostic cardio-vascular procedures, coronary and peripheral angioplasties or stenting, heart valve prosthesis implantation and heart valve repair, thoracoscopic, laparoscopic or endoscopic surgery, and the like. These procedures all require making a puncture in body organs or in the wall of a blood vessel to be used in the treatment of the patient's system. The size of the puncture will vary depending on the procedure and the inserted system. Depending on the procedure, commonly the femoral artery or the femoral vein is utilized as point of entry into the patient's system. Typical punctures can range from 2 mm to more than 10 mm in diameter, or from 6 French (Fr) to more than 30 French (Fr) for interventional procedures.

Other procedures, such as may be encountered with the use of endoscopes or other instruments, may utilize trocars for insertion. Typical trocar punctures can range from 2 mm to more than 15 mm in diameter, or from 6 French (Fr) to more than 45 French (Fr). Closure of such openings is typically accomplished using multiple levels of surgical sutures.

Upon completing the interventional diagnostic or treatment procedures utilizing vascular puncture as access site, whether of the peripheral circulation, the coronary circulation system or the heart, the devices and introducer casing may be removed, leaving a puncture site in the vessel wall or in the body organ.

Such perforations can be closed and sutured tight with common open surgical methods utilizing a single knot or running surgical sutures.

An alternative open procedure to stop the bleeding is the use of clips or staples. One form of a hemostatic clip is shown in U.S. Pat. No. 4,217,902 by March et al. that requires open surgical access of the perforation to allow operation of the clamping mechanism. And more sophisticated surgical staplers are described, as shown in US 2008/272173 by Coleman James et al., that require an open access.

Various procedures and devices have been developed to address the hemostasis after perforation of a blood vessel for a diagnostic or treatment procedure in a closed, non-surgical way.

A common way to stop the bleeding is by applying pressure to the location of the perforation and waiting for the natural blood clotting and self-healing characteristics of the patient to seal the vessel opening. Such pressure may be required for relatively long time, such as 30 minutes to up to an hour, followed by the patient being bedridden during this time, essentially immobilized and with a heavy sandbag placed on the puncture site to provide compression for several hours until the bleeding has stopped. Additional risk of hematoma exists from bleeding before complete hemostasis and sealing occur. This procedure may be time consuming with related downsides.

With the increasing size of the vessel perforation like in heart valve prosthesis implantation or heart valve repair systems, the compression of the perforation and waiting for the natural sealing of the opening becomes less effective or even ineffective.

While excessive bleeding can occur already in persons having a normal blood clotting response, there are patients who are utilizing anticoagulation medications which inhibit clotting, suffer from bleeding disorders, hypertension or obesity, which increases the risk of excessive bleeding following removal of the penetrating casing or treatment systems.

An improved way to stop the bleeding is by applying a collagen or polymer plug as shown in U.S. Pat. No. 5,275,616. Such procedure is effective especially in smaller perforations. However, placement of such plug material adds to the risk of intravascular thrombus formation and development of an inflammatory reaction.

Various percutaneous clips or staplers were developed to avoid an open access closure. The systems are inserted over the already utilized guide wire and the clips are operated percutaneously.

Various percutaneous suturing systems have been developed having closure systems that provide a plurality of needles that are joined by a suture. After the needles have passed through the vascular wall surrounding an opening, they are captured, drawn outward, tied and the knot pushed back through the tract to complete the closure. The placement of the suture needles requires an adequate engagement of tissue such that the placed sutures can hold and close the hole, which limits the system to the closure of rather smaller vascular perforations.

In procedures with perforations of body cavities and organs like thoracoscopic, laparoscopic or endoscopic surgeries, it is common to make an entry to the patient's body with a trocar of suitable size, large enough to insert the applicable system. Closure of such large bore perforations is commonly done by open surgical suturing.

SUMMARY OF THE INVENTION

An object of the present invention may be to propose a further medical apparatus for closing an aperture and a method thereto. Also, a closing device is proposed.

The above-mentioned object is achieved by the medical apparatus for closing an aperture with features as described herein, and is further achieved by the method for closing an aperture described herein, and by the closing device described herein.

In all of the aforementioned and following statements, the use of the expressions "may be" or "may have" and so on, is to be understood synonymously with "preferably is" or "preferably has", and so on respectively, and is intended to illustrate an embodiment according to the present invention.

Whenever numerical words are mentioned herein, the person skilled in the art shall recognize or understand them as indications of numerical lower limits. Hence, unless this leads to a contradiction evident for the person skilled in the art, the person skilled in the art shall comprehend for example "one" as encompassing "at least one". This understanding is also equally encompassed by the present invention as the interpretation that a numerical word, for example, "one" may alternatively mean "exactly one", wherever this is evidently technically possible in the view of the person skilled in the art. Both of these understandings are encompassed by the present invention and apply herein to all used numerical words.

If it is disclosed herein that the subject-matter of the present invention comprises one or several features in a particular embodiment, it is also respectively disclosed herein that the subject-matter according the present invention expressly does not comprise this or these features in other embodiments which likewise are according to the present invention, e.g. in the sense of a disclaimer. For each embodiment mentioned herein, the opposite embodiment, e.g. formulated as a negation, is also disclosed.

The present invention thus proposes a medical apparatus for closing an aperture, an incision, a puncture, a passage through tissue and/or a communication with a blood vessel or other body lumen (in short: aperture) of a tissue of a patient. Herein, the medical apparatus comprises a closing device holder for releasably receiving and/or holding one or more closing devices. The medical apparatus further comprises a retracting unit. The retracting unit may be designed or arranged to come, during use of the medical apparatus, into contact with, preferably opposite sides of the tissue of the aperture in order to retract them or the tissue and/or in order to spread the aperture, optionally causing it to change its shape into a slit or a slit-like or a more slit-like aperture. To this end, or for achieving this, the retracting unit may be suitably configured. For example, this retracting or this change may be achieved by widening a gap or distance between parts of the retracting unit (e. g. between retracting devices or their arms (if provided) or tips thereof) which in turn may result in spreading or augmenting the dimension or diameter of the aperture in at least one or in exactly one dimension of the aperture.

Moreover, a method for closing an aperture of a tissue is proposed. The method encompasses firstly the step of providing a medical apparatus according to the present invention and secondly the step of closing the aperture by using the medical apparatus.

Advantageous developments of the present invention are also described herein.

Whenever an embodiment is mentioned herein, it represents an exemplary embodiment according to the present invention. Whenever an invention is mentioned herein, the present invention is meant.

Embodiments according to the present invention may comprise one or several of the features mentioned supra and/or in the following in any combination which is technically possible.

In some embodiments, the retracting unit of the medical apparatus according to the present invention comprises at least one retracting device holder and at least one retracting device. The latter may preferably be at least partially received in the retracting device holder. The retracting device may optionally be at least partially received in the retracting device holder, preferably in a releasable manner, and is preferably arranged there in a moveable or slidable manner with respect to the retracting device holder.

The retracting device holder may have both a distal end, preferably configured to be advanced or extended through or into the aperture to be closed, and a proximal end.

In several embodiments, the retracting unit of the medical apparatus according to the present invention comprises at least one engaging device connected to said retracting device in order to releasably engage with the tissue.

In some embodiments, the engaging device may have a closed section having a through-opening. The closed section may have the shape of a rectangle, a square, a circle, an ellipse, or combinations thereof.

In several embodiments, the engaging device may comprise a wire or consist of a wire.

In some embodiments, the engaging device may be formed from a single wire.

In several embodiments, the engaging device may have or cover a convex or concave shape. In other embodiments it is flat or substantially plane.

In some embodiments, the engaging device of the medical apparatus according to the present invention is configured to be foldable and/or to be comprised or captured at least partially within the retracting device holder.

A mechanism for moving the engaging device and/or the retracting device into or out of the retracting device holder may be provided.

In several embodiments, the engaging device may be connected to the above-mentioned retracting device such that they are configured for engaging with the tissue surrounding the aperture from within or from below the aperture opening.

In some embodiments, at least two retracting devices and/or at least two engaging devices of the medical apparatus according to the present invention are captured within the retracting device holder in a releasable manner. In particular, they are captured such that they are arranged to be at least partly released from the retracting device holder by manipulating the retracting device holder or the engaging device or a mechanism configured to do so when required, in particular in order to be positioned below the opening level of the aperture to be closed.

In several embodiments, the retracting device holder and/or the retracting device and/or said engaging device of the medical apparatus according to the present invention are configured to retract the opposite sides of the aperture, in particular such that the aperture changes its shape. For example, the aperture may change from a rather round shape to a slit aperture. Preferably, this results in an extended transverse diameter that is at least double the length of the retracted longitudinal diameter of the aperture. "Transverse" may refer to a direction perpendicular to the longitudinal direction of the vessel. The longitudinal diameter may run in the direction of the longitudinal axis of the vessel.

In some embodiments, the retracting unit of the medical apparatus according to the present invention comprises at least a retracting device having at least one of the following:

a first side and an opposite second side, a first arm and a second arm, a first retracting device and a second retracting device, a first retracting device holder and a second retracting device holder, and/or a first engaging device and a second engaging device.

Additionally, the retracting unit or any other component may have a mechanism for moving the first side apart or away from the second side, the first arm apart or away from the second arm, the first retracting device apart or away from the second retracting device, the first retracting device holder apart or away from the second retracting device holder and/or the first engaging device apart or away from the second engaging device.

In several embodiments, the above-mentioned mechanism comprises or consists of a shape memory characteristic.

In some embodiments, the mechanism may comprise or consist of a mechanical means comprising, e. g., gears, rods, an actuating means, a control means such as a knob or handle, and the like.

In certain embodiments, an optional knob and/or a handle member or handle member casing (or at least or part thereof, respectively) of the medical apparatus is made from resin, plastic, glass fiber, wood, metal or composite materials or combinations of the materials mentioned here. In other embodiments, the optional knob and/or the handle member or handle member casing (or at least or part thereof, respectively) of the medical apparatus is not made from resin, or not from plastic, or not from glass fiber, or not from wood, or not from metal or not from composite materials or not from combinations of the materials mentioned here.

In some embodiments, the handle member or its casing comprises at least one slider, e. g., for the user. In others, it does not comprise any slider.

In some embodiments, the handle member or its casing comprises at least one rotational element, e. g., for the user, that translates rotation into translation. In others, it does not comprise such a rotational element.

In several embodiments, the mechanism may comprise or consist of a vacuum device configured to amend the shape of the retracting device, the retracting unit or any other component such that the first side or the first arm, and so on, is moved apart or away from the second side or the second arm, and so on.

The vacuum device may be arranged to suck a fluid (e. g., air) from an inner, preferably closed, lumen of, e.g., the retracting unit such that the cross section of that component, e.g. the retracting unit, is changed: by attempting to achieve a vacuum inside the lumen, the cross section of, e.g., the retracting unit will increase in a first dimension but decrease in a second dimension perpendicular to the first one. That way, opposite first and second sides of, e.g., the retracting unit will move away from each other while the circumference of the retracting unit is kept constant.

The preferably closed lumen which is in fluid communication with the vacuum device may in at least one state (having applied vacuum or not) have a cross section that is longer in a first direction thereof than in a second direction perpendicular to the first one.

In some embodiments, the retracting unit or the retracting device has a curve or a step or it bends on its front side or on its rear side that might be used as a stop or give the surgeon tactile feedback while partly withdrawing the medical apparatus from the vessel lumen. The curve, step or the like may indicate that the tip of the medical apparatus, or its retracting unit, retracting device or the like has come to rest at the rim of the vessel or the aperture. This, in turn, indicates that the medical apparatus is in a suitable position for deploying the closing device. To achieve this, the curve, step or the like is arranged under a pre-determined distance from, e. g., the free end of the medical apparatus or the retracting device. Also, the curve, step or position at which it is bent may serve as protection against pulling the medical apparatus too far out from the vessel lumen before releasing the closing device.

In several embodiments, the medical apparatus does not comprise vacuum device or source and/or is not connected to one.

In some embodiments, the medical apparatus is not a pressure stabilizer.

In several embodiments, parts of the retracting device (e. g., the tips of their arms, if provided) deviate or part from each other when released or in the unstressed state and/or when used for retracting issue.

In some embodiments, parts of the retracting device (e. g., two arms or the tips of these arms, if provided) deviate or part from each other when released or in the unstressed state and/or when used for retracting issue in common plane. The longitudinal axis of the handle member may be part of this plane or have an angle of less than 10°, 15° or 20° to this plane.

In several embodiments, the retracting device and the closing members, or parts thereof, respectively, may exit, at least in part, from the same handle member.

In some embodiments, the retracting unit is designed to come into contact with, e.g., opposite sides, of the aperture or the tissue surrounding the aperture and for retracting them and/or for spreading the aperture causing it to change its shape into a slit or a slit-like or a more slit-like aperture or to spread or to augment the dimension or diameter of the aperture in at least one or in exactly one dimension of the aperture by opening a space or gap between parts of the retracting device, e. e., by moving arms or tips of these arms, if provided, of the retracting device apart from each other, respectively.

In several embodiments, the medical apparatus according to the present invention comprises at least one closing device comprised in the closing device holder.

In some embodiments, the closing device of the medical apparatus according to the present invention is at least partially comprised within the closing device holder in a stressed state of the closing device. In particular, it is comprised within the distal end of the closing device holder, in particular when the closing device is in an undeployed state. Herein, the closing device has preferably two or more ends and a junction connecting with the two or more ends, e. g., via two or more arms.

In several embodiments, the closing device of the medical apparatus according to the present invention is comprised within the closing device holder such that when the closing device is manipulated to exit the distal end of the closing device holder during the use of the medical apparatus, the closing device releases its stress, or part of it, e.g., by bending the two or more arms outside of the closing device holder. Thereby, the two or more ends are arranged to perforate the inner wall of the tissue surrounding the aperture.

In some embodiments, at least part of the closing device, the retracting device, the retracting device holder and/or the engaging device of the medical apparatus according to the present invention is made of a deformable shape memory alloy and/or has a self-expanding shape memory section or a wire body.

In several embodiments, at least part of the closing device, the retracting device, the retracting device holder and/or the engaging device of the medical apparatus according to the present invention is made of Nitinol.

In some embodiments, at least part of the closing device, the retracting device, the retracting device holder and/or the engaging device of the medical apparatus according to the present invention is made of biocompatible and/or bio-absorbable material.

In several embodiments, the biocompatible and/or bio-absorbable material is at least one material selected from the group consisting of Ti, Ti alloys, Nitinol, stainless steel, polymeric materials, and ceramic.

In some embodiments of the medical apparatus according to the present invention, the closing device or parts thereof curl into a closed form (having, e.g., a through-opening surrounded by arm, struts or the like of the closing device) when in a stress-free state.

In several embodiments of the medical apparatus according to the present invention, the closing device or parts thereof curl into a loop- or ring- or circle-like shape when in a stress-free state.

In several embodiments of the medical apparatus according to the present invention, the closing device after deployment has a cross-sectional dimension ranging from 10 micrometers to 1 centimeter, preferably from 40 micrometers to 200 micrometers, more preferably from 50 micrometers to 100 micrometers.

In some embodiments, the closing device has two arms.

In some embodiments, at least one of the arms has a or one first bending direction and a or one second bending direction. Hence, a or one first section of the arm is bent in the first bending direction whereas a or one second section of this arm is bent in the second bending direction, wherein the first bending direction and the second bending direction are at least one of not identical to each other, opposite to each other and facing away from each other, or the like.

In some embodiments, in a closed state of the closing device or the vessel aperture, the end or tip of a first one of the arms points away from a second one of the arms, whereas the end or tip of the second arm points away from the first arm.

In some embodiments, the medical apparatus comprises or consists of a handle member (or handle or handle device).

In some embodiments, in order to activate or advance the retracting device, the handle member may have a first slider and optionally also a second slider arranged to be moved by the user, preferably in a longitudinal direction of the handle member.

Optionally, in its end position, or in another position, the first slider may be locked in place. A suitable mechanism may be provided, e. g., in the handle member.

In some embodiments, all or some of the closing device holders are parallel to each other, fully or only in parts thereof.

In some embodiments, the casing of the handle member comprises an opening in which a switch can be moved by the user to advance the closing device holders relative to the casing of the handle member.

In certain embodiments, the closing device holders are arranged to remain parallel to each other throughout the closing of the vessel aperture. In other embodiments, they are arranged to part or deviate from each other when being advanced towards the vessel aperture.

In some embodiments, the closing device holders are not parallel to each other, or only parts of them (e. g. their proximal parts) are parallel, but, for example, not their distal parts (their tips, e. g.). In certain embodiments, the proximal parts are parallel to each other. In some embodiments, the distal parts are under an—optionally constant—angle with regard to each other.

In some embodiments, the distance between the tips or distal ends of some of the closing device holders—for example when having been advanced towards the vessel aperture for closure—is larger than the diameter of the opening of the medical apparatus or the handle member from which the closing device holders exit for closing the vessel aperture.

In particular embodiments, the distance between the tips or distal ends or between any other corresponding parts of the closing device holders is equidistant between neighboring closing device holders in their unstressed or fully deployed state and/or when advanced for closing the vessel aperture.

In certain embodiments, the distance between the tips or distal ends of some of the retracting devices or of their arms—for example when having been advanced towards the vessel aperture for closure or in their unstressed or fully deployed stated—is larger than the distance between the tips or distal ends of some of the closing device holders mentioned supra.

In some embodiments, a delivery support for assuring that the closing device holders deviate or part from each other when being advanced towards the vessel aperture is provided.

In some embodiments, the delivery support comprises a wire, a wire net or structure, or consist thereof, respectively.

In some embodiments, the delivery support is a foldable and/or unfoldable element.

In some embodiments, at the outer or lateral sides of the closing member, of the closing device holders or of the delivery support bumpers are arranged.

In some embodiments, the handle member comprises a sleeve or another, preferably rotatable element or cylindric, element with an—optionally U- or V-shaped—guide slot (guidance groove). The guide slot can be part of the sleeve's outer surface or added to the latter.

In some embodiments, the guide slot comprises a first slot section and a second slot section each being connected with each other by another slot section, called a turning point.

In some embodiments, the handle member, the knob or the sleeve itself comprises an elastic element, a spring or the like arranged to also guide the pin through the turning point of the guide slot.

In some embodiments, the retracting device comprises a multitude (here: two) of arms.

In some embodiments, an arm of the retracting device comprises two legs, called an outer leg and an inner leg.

In some embodiments, the outer leg and the inner leg may be welded to each other in or by a welding section.

In some embodiments, the outer leg and the inner leg surround or circumscribe one or two middle openings which may be through-openings, or form the latter between them.

In some embodiments, the inner leg is straight or substantially straight.

In some embodiments, the outer leg is bent such that it has or forms an indentation, a bulge or a dent.

In some embodiments, the arms of the retracting device each exits through separate openings of the retracting unit. In other embodiments, some or all of the arms exit through a common opening of the retracting unit.

In some embodiments, at least one of the openings of the retracting unit through which the arms exit in use has a width that is smaller than its length.

In some embodiments, at least one of the openings of the retracting unit through which at least one arm exits has an oval opening area.

In some embodiments, the medical apparatus according to the present invention further comprises a pushing device, preferably extending through the proximal end of the closing device holder, for the manipulation of the closing device. The pushing device may be configured not to deform the closing device by acting on it, e.g., by pushing it.

In several embodiments of the medical apparatus according to the present invention, the pushing device is or comprises a rod or a piston.

In some embodiments, the medical apparatus according to the present invention further comprises a holding or withdrawing device extending through the proximal end of the closing device holder for the manipulation of the closing device. Herein, said holding device is, in particular releasably, attached to the closing device or connected therewith.

In several embodiments, the holding device of the medical apparatus according to the present invention is a string or a suture.

In some embodiments, the closing device holder of the medical apparatus according to the present invention has one or more grooves on the inner wall of the closing device holder and/or one or more grooves on the pushing device for guiding the holding device along the longitudinal direction of the closing device holder, preferably through or along the groove(s).

In several embodiments of the medical apparatus according to the present invention, the distal end of the closing device holder has two or more channels on the wall of the closing device holder. These channels allow one or more ends of the closing device to exit the closing device holder upon manipulation of the medical apparatus or when required by the user. The ends may exit from one side or both sides of the closing device holder. The channels may be slit-like. The channels or the proximal ends thereof may be exceeded in a distal direction of the closing device holder by the distal end.

In some embodiments of the medical apparatus according to the present invention, the distal end of the closing device holder has at least one channel or two channels arranged opposite to each other on the wall, in particular in the circumference of the closing device holder, of the closing device holder.

In several embodiments of the medical apparatus according to the present invention, the retracting device holder is or comprises an elongated tube. This elongated tube comprises or consists of, e.g., metal or plastic and is preferably configured to capture a retracting device.

The closing device holder may have a distal end for being advanced or extended through or into the aperture of the tissue, and a proximal end in particular suitable for providing access for manipulating a closing device when and if received in the closing device holder.

In some embodiments, at least one of the closing device holder and the retracting unit is at least one of slidably and moveably arranged within the medical apparatus with respect to each other, to other elements of the medical apparatus, and/or to a casing or an outer sheath of the medical apparatus.

In some embodiments, the medical apparatus comprises an outer housing, sheath or casing that comprises some or all elements (except for the housing or casing and the like, of course) of the medical apparatus, in particular the closing device holder and/or the retracting unit.

In some embodiments, the medical apparatus comprises a lumen for guiding and/or encompassing a guide wire. The lumen may be open to both the distal end and the proximal end of the medical apparatus or to just one of those.

In some embodiments, the medical apparatus comprises several lumen or openings. One of them may house a first closing device holder, another one may house a second closing device holder, a retracting device holder and/or any other element of the medical apparatus, for example.

Any lumen of the medical apparatus may be a through-opening of the medical apparatus, preferably extending in a longitudinal direction of the medical apparatus.

In some embodiments the medical apparatus has an outer housing or unit that is, along its entire length or along only parts of it, not flexible and/or flexible.

In several embodiments of the method according to the present invention, the method comprises the following further steps:

introducing parts of the retracting unit into the aperture;

contacting opposite sides of the aperture with the retracting unit or elements comprised by it;

retracting the opposite sides of the aperture and/or spreading the aperture with the retracting unit or elements comprised by it; and releasing at least one closing device from the closing device holder and connecting the opposite sides of the aperture to each other with the closing device.

In some embodiments of the method according to the present invention, the step of retracting opposite sides of the aperture and/or spreading the aperture causes the aperture to change its shape, e.g., into a slit or a slit-like or a more slit-like aperture. This change may result in spreading or augmenting the dimension or diameter of the aperture in at least one or in exactly one dimension of the aperture.

In some embodiments at least one of the closing device holder and the retracting device holder is a partly hollow tube.

In some embodiments at least one of the closing device holder and the retracting device holder are arranged within a common casing or housing, preferably slidable or moveable with respect to that casing.

In some embodiments the closing member is identical to the closing device holder.

In some embodiments the retracting unit is identical to the retracting device holder.

In some embodiments the retracting unit and the closing member are embodied by one device only.

In some embodiments the device has no guide wire. It may, however, have a lumen for running a guide wire through the length of the device and/or in the direction of its length.

In some embodiments the closing device is a staple or a clip, a wire structure, or the like. It may have any features disclosed herein in any arbitrary combination.

In some embodiments the closing device holder is not configured to eject or to release the closing devices, in particular staples or clips, in a first direction wherein a component of the device or of the closing device holder configured to eject the closing device or to assist in ejecting them, is arranged to be moveable at best (or ideally only) in the first direction or at best substantially in the first direction. However, in those embodiments, that component is not configured or arranged to be moveable in a second direction which is substantially perpendicular to the first direction.

In some embodiments at least one of the closing device holder and the device has no devices configured for plastically deforming the closing devices, in particular not for plastically deforming them while there are ejected or released. Also, there is preferably no device provided for closing a closing device.

In some embodiments the closing device holder is configured to simultaneously eject or release two or more closing devices. For example, the closing device may be ejected from one common opening of the holder through which they leave side by side. Alternatively, the configuration may be such that two or more closing devices may leave the closing device holder or the device through separate openings but at the same time.

In some embodiments, the closing device holder is configured such that the closing device can only be ejected or released in the longitudinal direction of the closing device holder.

In some embodiments, the closing device holder is configured such that the closing device can only be ejected or released at the same position with respect to the length or the longitudinal direction of the closing device holder.

In some embodiments the retracting unit comprises at least two elements that move apart from each other while retracting the aperture, for example, two sides, two arms, two retracting devices or two retracting device holders.

In some embodiments the retracting unit and the closing device holder are separate from each other, and, in particular, may move separately from each other. In other embodiments, they are interconnected to each other or embodied by the same unit such that they cannot move independently from each other.

In some embodiments the retracting unit and the closing device holder are spaced apart from each other such that the closing device holder is configured to eject or release the closing device or devices into the tissue in order to have them close the rim or seam of the long sides of aperture in retracted state of the aperture, that is while the aperture is being retracted or spread by the retracting unit.

In some embodiments at least one of the components of the retracting unit configured to retract the opposite sides of the aperture by directly touching them is an elongated or oblong section. At least one of them may have the shape of a pole, a tube or the like, and they are, preferably, straight.

In some embodiments at least one of the components of the retracting unit configured to retract opposite sides of the aperture by directly touching them (such as the first and the second arms or sections, the first and the second retracting devices, the first and the second retracing device holder and/or the first and the second engaging device) does not comprise one or more hinges, articulations, joints or sections where it bends, in particular not in a middle section thereof, more particular not facing to opposite directions from each other.

In some embodiments the components of the retracting unit configured to retract the opposite sides of the aperture by directly touching them have a free distal end.

In some embodiments, some or all of the components of the retracting unit configured to retract opposite sides of the aperture by directly touching them are configured to move with respect to each other in a first common plane while retracting the aperture. Optionally, in these or in different embodiments the at least one closing device extends (e. g., in a deployed state of the closing device, e. g., when being released or ejected) entirely or substantially in a second plane. Also, the closing device may optionally close in the second plane. For example, the closing device may comprise arms or tines that move towards each other upon closing or deploying. That movement can also take place in substantially one plane, namely the second plane. The first plane and the second plane may intersect each other. They may be substantially perpendicular to each other.

In some embodiments, some or all of the components of the retracting unit configured to retract opposite sides of the aperture by directly touching them are configured to move with respect to each other in a first direction while retracting the aperture. Optionally, in these or in different embodiments the device is configured to eject or to release the at least one closing device in a second direction. The first direction and the second direction may be different from each other. In fact, they may be perpendicular or substantially perpendicular to each other. Hence, the direction of retracting may be perpendicular or substantially perpendicular to the direction in which the closing device is ejected or released and/or in which the closing device closes when the device is used by the surgeon.

In some embodiments the first and the second retracting devices, or first and second arms or sections thereof, are connected to each other by just one hinge or joint or hinge or joint section. That hinge or joint or section may be arranged to move—preferably exclusively—inside the retracting device holder and/or along the longitudinal axis of the medical device or the of the retracting device holder. Additionally, or alternatively, that hinge or joint or section may be arranged to move—preferably exclusively—in the second direction, not, however, in the first direction. Hence, in those embodiments the hinge or joint or section may optionally not move in the direction in which the opposite sides of the aperture are retracted or spread.

According to the present invention, a medical apparatus for closing an aperture of a tissue is also suggested, comprising a closing device holder, wherein said closing device holder has a distal end for extending through the aperture of the tissue in a deployed state of the medical apparatus, and a proximal end for providing access for manipulation of a closing device; and a closing device at least partially captured in a stressed state within the distal end of the closing device holder when the medical apparatus or the closing device is in an undeployed state; wherein the closing device has two or more ends and a junction connecting with the two or more ends via two or more arms;

wherein the closing device is configured relative to the closing device holder so that when the closing device is manipulated to exit the distal end of the closing device holder during the deployment of the medical apparatus or the closing device, the closing device releases its stress by bending the two or more arms outside of the closing device holder, whereby the two or more ends perforate the inner wall of the tissue surrounding the aperture.

According to the present invention, a method for closing an aperture of a tissue is also suggested, the method encompassing the steps:

providing a medical apparatus according to the present invention;

closing the aperture by means of the medical apparatus.

In some embodiments according to the present invention, at least part of the closing device is made of a deformable shape memory alloy.

In some embodiments according to the present invention, at least part of the closing device is made of Nitinol.

In some embodiments according to the present invention, at least part of the closing device is made of biocompatible and/or bio-absorbable material.

In some embodiments according to the present invention, the biocompatible and/or bio-absorbable material is at least one material selected from the group consisting of Ti, Ti alloys, Nitinol, stainless steel, polymeric materials, and ceramic.

In some embodiments according to the present invention, the closing device curls into a closed form when in a stress-free state.

In some embodiments according to the present invention, the closing device curls into a loop- or ring- or circle-like shape when in a stress-free state.

In some embodiments according to the present invention, the closing device after deployment of the medical apparatus has a cross-sectional dimension ranging from 10 micrometers to 1 centimeter, preferable from 40 micrometers to 200 micrometers, more preferably from 50 micrometers to 100 micrometers.

In some embodiments according to the present invention, the medical apparatus comprises a pushing device extending through the proximal end of the closing device holder for the manipulation of the closing device.

In some embodiments according to the present invention, the pushing device is a rod or piston.

In some embodiments according to the present invention, the medical apparatus comprises a holding device extending through the proximal end of the closing device holder for the manipulation of the closing device, wherein said holding device is attached with the closing device.

In some embodiments according to the present invention, the holding device is a string or suture.

In some embodiments according to the present invention, the closing device holder has one or more grooves on the inner wall of the closing device holder and/or one or more grooves on the pushing device for guiding the holding device along the longitudinal direction of the closing device holder.

In some embodiments according to the present invention, the distal end of the closing device holder has two or more channels on the wall of the closing device holder, allowing the one or more ends of the closing device to exit the closing device holder when deploying the closing device.

In some embodiments according to the present invention, the distal end of the closing device holder has two channels arranged opposite to each other on the wall of the closing device holder.

Most of the systems that are state of the art like utilizing plugs, clips or sutures can only close rather smaller size arterial perforation up to 10 French (Fr) and are only approved for arterial access sites. Some of the systems are used off-label for closing larger arterial or venous punctures.

The present invention may advantageously provide a more effective method and a medical apparatus for sealing large bore punctures up to 30 French (Fr) and larger in veins and other passages through tissues.

The present invention allows to connect tissue segments together or to close and/or seal an opening through tissue, such as very large bore vascular perforations in the venous system in particular the Vena femoralis.

Such large vascular access and perforations are required for more complex interventional procedures like transseptal mitral and tricuspid valve repair and prosthesis implantation.

The femoral vein has a diameter of approximately 8 mm or 24 French (Fr), and more, allowing introduction of systems with a similar diameter. It is very challenging to close such large bore perforations of the vein with a percutaneous system utilizing plugs, sutures or clips. When closing such large bore perforations in a circular or longitude way, the risk of a vascular stenosis is high.

According to the present invention, a particular technique is advantageously used to stretch the perforation in a direction orthogonal to the vessel long axis and to suture the perforation close along this stretch. In this way narrowing of the vessel lumen is avoided.

The present invention allows closing a large bore vascular perforation in particular in veins by stretching the perforation in an orthogonal direction to the vessel long axis and placing single clips along the stretch that close the perforation along the stretched line.

In some embodiments, the medical apparatus may include a handle member and a tube set coupled to the handle member on one side (not shown) and on the other side, retracting units and closing members that are deployed subsequently or simultaneously in a tissue aperture. The handle member may also include any number of mechanisms (not shown) necessary to deploy a retractor and closing members. The retracting units and closing members are deployed through a casing that allows these units and members to be disposed at least partially in the aperture or lumen of a vessel in a controlled manner, in particular along a guiding structure, like a guide-wire or other rail (not shown) that is commonly placed in a vessel for performing interventional procedures.

The retracting units optionally include two retracting device holders with distal ends configured for extending through the aperture and to be positioned at the opposing inner side of the aperture to be closed. The retracting devices or their holders may have engaging devices mounted at, e.g., the distal end thereof. The engaging devices may be arranged for engaging the opposing end of the aperture and of the inner vessel wall, e. g. by contacting, pushing and/or abutting them. The engaging devices are configured to move apart, retracting the opposing sides of the aperture and stretching the aperture which approximates the opposing sides of the aperture between the retracting devices, such that the aperture becomes straight with one extended long diameter and an orthogonal retracted short diameter.

The closing member optionally includes one or more closing device holders with a distal end extending through the aperture to be closed, the closing device holders having closing devices mounted at, e.g., the distal end. The closing devices are arranged for engaging the tissue wall as the closing device holders are withdrawn.

The closing devices are preferably pointed needles that penetrate the tissue wall surrounding the aperture when the closing device holders are withdrawn. When the closing devices are engaged with the tissue wall it can be detected as a firm resistance to further withdrawal.

The closing devices are then deployed, bend further into a circular structure and draw the ends of the transversely retracted aperture together in a manner such that it closes the aperture in a straight line.

The closing devices optionally comprise a plurality of round needles of size, orientation and form such that when the closing devices are moved outwardly from inside of the aperture, the closing devices bend in an anchor like manner according to the preset memory shape of the closing devices, perforate the tissue wall and also grab tissue that is in close proximity to the wall causing the tissue surrounding the perforation to be drawn into close proximity of the closed aperture, such that the aperture can be closed and the drawn-in surrounding tissue will additionally seal the tissue closure.

The closing device, or the plurality of closing devices, can optionally be disengaged from the closing device holders and delivery mechanism, and left in place.

With the tissue aperture closed in such way, blood stasis can be achieved in a vessel by leaving the closing devices attached to the tissue wall. The closing devices may be constructed of metal, plastic or bio-absorbable material preferably having a memory material effect.

In some embodiments according to the present invention, for use in closing an aperture, incision, puncture, or other passage through tissue, communication with a blood vessel or other body lumen, a medical apparatus is suggested comprising one or more retracting units.

The retracting units have, e.g., two retracting device holders with a distal end for extending through the aperture to be closed and with a proximal end for selectively providing manipulation.

Engaging devices are captured in the retracting device holders, to be released by manipulation and positioned below the aperture to be closed. Said manipulation of said retracting device holders causes retraction of opposite sides of the aperture, causing the aperture to change the shape from a rather round aperture to a slit aperture whose extended transverse diameter (which is the longer diameter of the aperture after having retracted it) is at least double the length of the retracted longitudinal diameter (which is the shorter one) of the aperture.

In some embodiments according to the present invention, for use in closing an aperture in a tissue, a medical apparatus is suggested, the medical apparatus comprising closing members, the closing members having closing device holders with a distal end for extending through the aperture to be closed and having a proximal end for selectively providing manipulation; and having closing devices captured at the distal end of the said closing device holders to be deployed and whereby said manipulation of said closing device holders and deployment of closing devices causes the aperture to be closed.

In some embodiments according to the present invention, the medical apparatus comprises a set of retracting units.

In some embodiments according to the present invention, the medical apparatus comprises an indication for the user indicating the orientation or direction of the retracting units of the medical apparatus, e.g. being embodied as a sign, an arrow, or the like.

In some embodiments according to the present invention, the medical apparatus further includes delivery devices for delivering said closing device holder, engaging device and closing device to an operative proximity with the aperture, said delivery device being slidably connected, e.g., to said closing device holder.

In some embodiments according to the present invention, the retracting device holder comprises an elongated tube made of metal or plastic capable to capture a retracting device.

In some embodiments according to the present invention, the retracting units can be moved apart to retract an aperture.

In some embodiments according to the present invention, the retracting device holder comprises an elongated tube made of metal, plastic or other material capable to capture a retracting device.

In some embodiments according to the present invention, the closing device holder has a lateral channel at the end of the said elongated tube through which the closing device will leave the closing device holder, avoiding contact of the closing device with a structure opposite to the end of the elongated tube.

In some embodiments according to the present invention, the closing member can be manipulated to evenly distribute closing devices along the line to be closed.

In some embodiments according to the present invention, the closing devices are made of a perforating material, preferably a needle, selected from a class of material including metal, metal alloys, Nitinol, plastics, preferably having memory effect characteristics, and having a permanent or bio absorbable protective coating and being bio-absorbable.

In some embodiments, according to the present invention, the closing devices have a predetermined cross section, a proximal end and two arms each with a pointed end; both arms are the bending portion of the closing device, to expand between a first position when compressed and captured in the said closing device holder into a second position. The closing device is substantially linear and can be moved along the axis inside of the closing device holder in both directions in a compressed or strained state and can be released at the end of the closing device holder, returning the arms to the expanded second position with the arms having a bent shape, forming a ring with two hemi-circles or semi-circles.

In some embodiments according to the present invention, the closing devices have a preset form that allows connecting the closing devices with said closing device holder.

In some embodiments according to the present invention, the invention relates to a method for closing an aperture in a wall, incision, puncture, or other passage through tissue, communication with a blood vessel or other body lumen, in particularly, but not exclusively, the wall of a blood vessel, wherein the blood vessel has a lumen carrying blood.

It encompasses the steps:
a. retracting opposite sides of the aperture to be closed, causing the aperture to change the shape from a rather round aperture to a more slit-like aperture with a diminished diameter in axial direction to a vessel long axis and an expanded orthogonal diameter to the vessel long axis diameter, in preparation for connecting the expanded orthogonal sides of the aperture;
b. inserting and evenly deploying one or a plurality of closing devices through the aperture into the vessel lumen, the closing devices are manipulated to engage the vessel wall surrounding the aperture at the extended long sides of the aperture between the shoulders, and to connect the two expanded orthogonal sides of the retracted aperture sides and to close the aperture.

In some embodiments according to the present invention, the step of closing includes suturing, clamping or similar mechanical approximation of the engaged aperture wall.

In some embodiments, the retracting unit comprises an engaging device connected to said retracting device for releasably engaging with the tissue.

In some embodiments, the engaging device is configured to be foldable and/or to be comprised or captured at least partially within the retracting device holder.

In some embodiments, at least two retracting devices and/or at least two engaging devices are captured within the retracting device holder in a releasable manner, in particular such that they are arranged to be at least partly released from the retracting device holder by manipulating the retracting device holder or the engaging device, in particular to be positioned below the opening level of the aperture which is to be closed.

In some embodiments, the retracting device holder and/or the retracting device and/or said engaging device are configured to retract the opposite sides of the aperture, in particular such that the aperture changes its shape, e. g. from a rather round aperture, to a slit aperture, preferably such that the extended transverse diameter is at least double the length of the retracted longitudinal diameter of the aperture.

In some embodiments, the mechanism comprises or consists of a shape memory characteristic.

In some embodiments, the closing device is at least partially comprised within the closing device holder in a stressed state, in particular within the distal end of the closing device holder, in particular when the medical apparatus is in an undeployed state; wherein the closing device has preferably two or more ends and a junction connecting with the two or more ends, e. g., via two or more arms.

In some embodiments, the closing device is comprised within the closing device holder such that when the closing device is manipulated to exit the distal end of the closing device holder during the use of the medical apparatus, the closing device releases its stress or part of its stress by bending the two or more arms outside of the closing device holder, whereby the two or more ends are arranged to perforate the inner wall of the tissue surrounding the aperture.

In some embodiments, at least part of the closing device, of the retracting device, of the retracting device holder and/or of the engaging device is made of a deformable shape memory alloy and/or has a self-expanding shape memory section or wire body.

In some embodiments, at least part of the closing device, the retracting device, the retracting device holder and/or the engaging device is made of Nitinol.

In some embodiments, at least part of the closing device, of the retracting device, of the retracting device holder and/or of the engaging device is made of biocompatible and/or bio-absorbable material.

In some embodiments, the biocompatible and/or bio-absorbable material is at least one material selected from the group consisting of Ti, Ti alloys, Nitinol, stainless steel, polymeric materials, and ceramic.

In some embodiments, the closing device or parts thereof curl into a closed form when in a stress-free state.

In some embodiments, the closing device or parts thereof curl into a loop- or ring- or circle-like shape when in a stress-free state.

In some embodiments, the closing device after deployment, has a cross-sectional dimension ranging from 10 micrometers to 1 centimeter, preferably from 40 micrometers to 200 micrometers, more preferably from 50 micrometers to 100 micrometers.

In some embodiments, the medical apparatus further comprises a pushing device, preferably extending through the proximal end of the closing device holder, for the manipulation of the closing device.

In some embodiments, the pushing device is a rod or piston.

In some embodiments, the medical apparatus further comprises a holding device extending through the proximal end of the closing device holder for the manipulation of the closing device, wherein said holding device is attached to the closing device.

In some embodiments, the holding device is a string or suture.

In some embodiments, the closing device holder has one or more grooves on the inner wall of the closing device holder and/or one or more grooves on the pushing device for guiding the holding device along the longitudinal direction of the closing device holder.

In some embodiments, the distal end of the closing device holder has two or more channels on the wall of the closing device holder, allowing the one or more ends of the closing device to exit the closing device holder upon manipulation of the medical apparatus or when required by the user.

In some embodiments, the distal end of the closing device holder has at least one channel or two channels arranged opposite to each other on the wall of the closing device holder.

In some embodiments, the retracting device holder comprises an elongated tube, e.g., comprising or consisting of metal or plastic, preferably configured to capture a retracting device).

In some embodiments, the method further comprises the steps:

introducing parts of the retracting unit into the aperture;

contacting opposite sides of the aperture with the retracting unit or elements comprised by it;

retracting the opposite sides of the aperture and/or spreading the aperture with the retracting unit or elements comprised by it; and releasing at least one closing device from the closing device holder and connecting the opposite sides of the aperture to each other with the closing device.

In some embodiments, the step of retracting opposite sides of the aperture and/or spreading the aperture causes the aperture to change its shape into a slit or a slit-like or a more slit-like aperture or to spread or to augment the dimension or diameter of the aperture in at least one or in exactly one dimension of the aperture.

In some embodiments, the retracting device is configured to retract the aperture in a direction perpendicular to the longitudinal axis of the retracting unit and/or the closing device holder.

In some embodiments, the retracting device is configured to retract the aperture in a direction with an angle between 90 degrees and 45 degrees relative to the longitudinal axis of the retracting unit and/or the closing device holder. The angle can be 90 degrees, 85 degrees, 80 degrees, 75 degrees, 70 degrees, 65 degrees, 60 degrees, 55 degrees, 50 degrees, 45 degrees or any angle between these degrees. Of course, in other embodiments, the angle may be 0 degrees or between 0 and 45 degrees.

In some embodiments, the retracting device is configured to retract the aperture in a direction not parallel to the longitudinal axis of the retracting unit and/or the closing device holder.

In some embodiments, the retracting device or the retracting unit does not have a motor or mechanism, e. g., for rotating or moving the arms or other parts for retracting opposite sides of an aperture around the axis or parallel to the axis which is the longitudinal axis of the retracting unit and/or the closing device holder.

In other embodiments, the retracting device or the retracting unit does have a motor and/or a mechanism for acting on the retracting device and/or on the retracting device holder.

In certain embodiments, the retracting device and the retracting device holder are arranged for not being moveable independently from each other.

In some embodiments the arms are part, extensions or protrusions of the retracting device holder. For example, the retracting device holder may have two distal tips, or it can terminate in a half-moon shape, a C-shape, and/or in any other shape that allows two parts separated by a gap to deviate from each and increase the gap or the distance between them, for example, should the shape of the retractor device holder change. Hence, the two tips mentioned here may be understood as arms as noted herein. Also, what has been stated herein with regard to "arm" may undiminishedly hold true for the tips, the two free ends of the C-shape or the half-moon shape mentioned supra.

The term mechanism as used herein refers in particular to a mechanism comprising moveably arranged parts such as plungers, gears, a motor, and the like.

In some embodiments, the medical apparatus comprises a deploying device configured to be at least partially releasably received in a lumen of the retracting device holder. The deploying device can comprise a cylindrical shaped body. The cylindrical shaped body can be hollow, partially hollow or solid inside. The distal end section of the deploying device can comprise a conical shaped end section. The very distal end of its tip, end or end section can comprise a spherical shaped tip.

In some embodiments, the retracting device is positioned at the distal tip, end or end section of the retracting device holder. The retracting device and the retracting device holder are preferably designed integrally with each other and/or preferably are connected to each other in a non-releasable manner or in a manner that does not require releasing during use of the invention.

In some embodiments, the retracting device comprises a first arm and a second arm (or consists thereof). Preferably, the first arm and the second arm are positioned or provided parallel to each other, preferably at least while positioning the retracting unit into the aperture.

In some embodiments, the retracting device comprises a first arm and a second arm (or consists thereof), which are arranged at or in contact with the surface of the deploying device while (during the) positioning (of) the retracting device to the aperture and which are expanded to a retracted state of the aperture after having pulled the deploying device out of the retracting device holder.

In some embodiments, the retracting device comprises a first arm and a second arm (or consists thereof), which are releasably attached to or in contact with the surface of the deploying device while advancing the retracting device to or into the aperture and which are expanded to assume a retracting or state of the aperture after pulling out the deploying device from the retracting device holder.

In some embodiments, the retracting device comprises a first arm and a second arm (or consists thereof), which are arranged at the surface of the deploying device while positioning the retracting device to the aperture and which are expanded passively, without a mechanism to a retracting state of the aperture after pulling out the deploying device from the retracting device holder.

In some embodiments, the retracting device holder or its lumen exhibits, assumes or shows a first shape or a first cross section, preferably a circular cross-section with a cross section diameter, while positioning the retracting unit into the aperture, and a second shape or a second cross section, preferably an oval cross section with a main axis length, preferably larger than the cross section diameter, after pulling out the deploying device, partly or completely, from the retracting device holder.

In some embodiments, the retracting device holder or its lumen exhibits, assumes or shows a first shape or a first cross section, preferably a circular cross-section with a cross section diameter, while positioning the retracting unit into the aperture, and a second shape or a second cross section, preferably an oval cross section with a main axis length, preferably larger than the cross section diameter, preferably an elliptical cross section with two symmetry axes, main axis and minor axis, after pulling out the deploying device, partly or completely, from the retracting device holder.

In some embodiments, the shape of the closing device holder or of its cross section mainly assumes the second shape or takes on the second cross section, corresponds to it and/or has an oval cross section, preferably with a main axis length slightly smaller than this length.

In some embodiments, the retracting device holder or parts of it are sufficiently flexible and/or elastic to enable the closing device holder to adapt the retracting device holder's shape or cross section while it is being inserted/introduced into the retracting device holder (and preferably (by it alone being introduced, i. e.,) without any additional assistance). For example, if the closing device holder or parts of it have an elliptical cross section, in these embodiments the retracting device holder or its inner lumen also assumes an elliptical cross section. Also, if the deploying device having a round cross section is inserted into the inner lumen of the retracting device holder, the inner lumen may assume a round cross section.

Hence, in some embodiments, the retracting device holder or parts thereof defining its inner lumen may have been produced from a material that is flexible or elastic.

Also, in some embodiments, the retracting device holder or parts thereof which define/determine (defining) its inner lumen may have been produced from a material that has no memory effect.

Hence, in some embodiments, the retracting device holder or parts thereof defining its inner lumen may have been produced from a material that is not flexible and/or not elastic.

In some embodiments, the medical apparatus comprises one or more bars or other protrusions that are arranged between or adjacent to openings of the closing device holder for discharging the closing devices. The bars are arranged to protrude over the opening area of at least one of the openings. They may be integral to the closing device holder, and they may serve to avoid damaging the opposite vessel wall or tissue when releasing the closing devices from the closing device holder.

In some embodiments, the medical apparatus comprises a connector to be connected, or to be an integral part of, the retracting device holder, providing an opening for advancing the deploying device and/or the closing device holder into the inner lumen of the retracting device holder.

In some embodiments, the inner lumen of the connector, or of a cross section thereof, or the opening area of the opening may comprise both sections that delimit a round shape (at least partially) and sections that delimit an oval shape (at least partially).

In some embodiments, the connector may comprise a seal, membrane, diaphragm or the like acting as a seal by adapting or abutting itself to the outer surface of a device inserted through the connector and into the inner lumen of the retracting device holder.

In some embodiments, the seal, membrane, diaphragm or the like may comprise slits through its material that allow the material to deviate or diverge in order to receive the device and to close the opening again once the device has been removed from the retracting device holder.

Hence, in some embodiments, the shape of the inner lumen of the connector, or of a cross section thereof, or of the opening area is neither exclusively round nor exclusively oval.

In some embodiments, the closing device holder is preferably at least partially releasably received in the retracting device holder, preferably translationally in a longitudinal direction of the closing device holder.

In some embodiments, a method for closing an aperture of a tissue, encompasses the steps:

- providing a medical apparatus, comprising a retracting device holder, a retracting device with a first arm and a second arm, and a deploying device, wherein the retracting device is positioned at the distal end section of the retracting device holder or attached to the latter;
- inserting the deploying device into the lumen of the retracting device holder;
- pushing forward both the deploying device and the retracting device holder, comprising the retracting device, up to the aperture until the first arm and the second arm are positioned inside the aperture;
- pulling back the deploying device out of the lumen of the retracting device holder;
- inserting a closing device holder with closing devices into the lumen of the retracting device holder, whereas the lumen is optionally mostly elliptical or oval shaped, so that the distal opening or openings of the closing device holder, for discharging the closing devices from the closing device holder is/are positioned at the aperture;
- pushing out, bringing out or releasing the closing devices for closing the aperture;
- optionally closing the aperture by means of the closing devices.

In some embodiments, a number of arms are provided to act as retraction unit or as part thereof. In some embodiments, some or all of the arms are provided in a line or in a common plane, or in contact with or crossed by a common plane.

In some embodiments, the tip of the retraction unit is formed by the tips of the arms that are arranged to not deviate from each other in a lateral direction, preferably at no state while closing the aperture.

In some particular embodiments, the lengths of the arms are different from each other. Hence, two or more different lengths can be provided for the arms, or some of the arms may be moved out from the retracting unit, a common sheath or a casing thereof by a greater length than other ones.

Hence, in some embodiments, the retraction unit may comprise or consist of a number of arms. Some of the arms may differ in lengths or by the extent to which they may be advanced from the inner of the retraction unit to an outside thereof.

In certain embodiments, all of some of the arms of the retraction unit may be arranged to be advanced into an advanced position and retracted from the advanced position again without being bent or deviated to a lateral side.

In some embodiments, the arms can be straight or longitudinal components which either cannot be bent during use or will always run in parallel to each other (or both).

In some embodiments there is no form the arms would assume (due to shape memory features, for example) other than the form the arms have while not being advanced.

The arms may be arranged to be moved out of the casing or an inner of the medical device only if moved together.

Hence, they may be interconnected to each other in a way such that they can only be advanced as a group.

In some embodiments, protectors are provided. They may comprise wire, or consist thereof.

The protectors may be connected to the arms. They may be arranged to be slided out of the casing or relative to other parts of the medical apparatus, together or only together with the respective arm.

In some embodiments, one arm is connected to one protector on its upper face, another protector is connected to the lower face thereof.

In some embodiments, the protectors are arranged to unfold in a direction that is preferably perpendicular (or also perpendicular) to the longitudinal axis of the retracting unit or of the respective arm.

The protectors may be arranged to unfold in a direction that is preferably perpendicular (or also perpendicular) to the direction of the largest extension of the retracting unit or of the respective arm in a breadth of the retraction unit or its casing.

In some embodiments, the breadth of the casing or the retracting unit width or depth thereof, preferably rendering the casing or the retracting unit not round but rather flat, rectangular, elliptical or the like in cross section.

In some embodiments, the closing device comprises or consists of two arms. The may either originate from a common integral material or they may be attached one to the other in an attaching area. They may be glued, welded or attached in any other way to each other.

In some embodiments, the shape of the closing device is not symmetrical, preferably in no state thereof.

In some embodiments, the attaching area is inclined to a center line of the closing device.

For example, the attaching area may be inclined to a line perpendicular to the line of maximum breadth or to a straight line connecting the tips of the arms by an angle between 20° and 70°, preferably between 30° to 60°.

In some embodiments, the attaching area comprises a through-opening 611. The through-opening 611 may have a closed circumference, or it may be open toward the circumference by means of an extension of it. The extension may be narrower than the radius of the through-opening itself. Hence, the extension may turn the overall-shape of the through-opening into a key-hole-shape. The extension may be a bottle neck, in one plane, to the main area of the through-opening.

The wire the arms of the closing device are made of are preferably made from a flat wire or comprise a flat wire. A flat wire has, in contrast to a round wire, no round cross section. Its cross section is elliptical, rectangular or deviates in another way from a round design. Flat wire allows for higher grip force without surpassing for example nitinol's irreversible strain threshold. Also, it appears that the closing device is able to hold a vessel wall with a relevant amount of perivascular tissue and cinch together to create hemostasis and full closure.

In some embodiments according to the present invention, the medical apparatus for closing an aperture comprises features as disclosed herein, in any arbitrary combination unless not considered technically impossible by the skilled one. These and other more detailed and specific objectives and an understanding of the various embodiments of the invention will become apparent from a consideration of the following detailed description of the exemplary embodiments in the view of the drawings.

BRIEF DESCRIPTION OF THE DRAWINGS

FIG. 2A to 2F are side views of an alternative embodiment of the retracting unit;

FIG. 13A to 13H are schematic, partially sectioned longitudinal cross-section views of an alternative closing member from FIG. 10 and the closing device from FIG. 6 deployed in the aperture, penetrating the tissue and connecting the free edges of the aperture;

FIG. 15 is a schematic, partially sectioned perspective view of two retracting units deployed within the aperture, the two retracting devices from FIG. 4 advanced and deployed within the vessel;

FIG. 16 is a schematic, partially sectioned perspective view of two retracting units deployed within the aperture, the two retracting devices from FIG. 4 advanced and deployed within the vessel and the aperture is retracted;

FIG. 31 shows a closing device in another embodiment in a front view;

FIG. 31A shows the closing device of FIG. 31 in a perspective view;

FIG. 33 shows parts of the medical apparatus according to an embodiment of the present invention in a perspective view;

FIG. 34 shows in a perspective view a part of another embodiment of the medical apparatus;

FIG. 36 shows a highly simplified view onto the front-end surface of the medical apparatus;

FIG. 46A to 46E are schematic views of alternative embodiments of a retracting unit of a medical apparatus, according to this invention;

DETAILED DESCRIPTION OF EXEMPLARY EMBODIMENTS OF THE INVENTION

Specific embodiments of the present disclosure are directed to a vascular closing apparatus and a method for closing an aperture in a tissue such as a vascular closing device comprising a tissue retracting unit and an aperture closing member.

Tissue Retraction

In one aspect of the present invention, a retracting unit is provided to retract two opposing sites of a tissue aperture. After the two arms, sides or the like are deployed at opposite sides in the aperture to close, the distance between the arms, sides and so on is increased in order to retract the opposing sides, changing the shape of the tissue opening (aperture) to a slit, in which the two long straight sides of the aperture are approximated in preparation for the closure.

It will be appreciated by those skilled in the art, that the closure of the vessel as described herein follows the principle of surgical vascular closure techniques to prevent a narrowing or stenosis of the vessel to be treated. The retracting device is preparing the aperture in the tissue to become a transverse slit orthogonal to the vessel's long axis, comparable with an open surgical transverse suture-line. A circular retraction of the aperture, like in an open surgical cross-stich procedure or a longitudinal suture-line is prevented to avoid stenosis of the vessel to be treated, see FIG. 27.

Aperture Closure

Another aspect of the present invention relates to a closing member to close a tissue aperture that was prepared with the retractor unit. It should be recognized that the retracting unit and the closing member might be used for general tissue repair, not just limited to vascular repair. It will be appreciated throughout the following description that the closing device of the medical apparatus can be formed of any biocompatible and/or bio-absorbable material, including, for example, Titanium (and Titanium alloys), Nitinol, stainless steel, polymeric materials (synthetic and/or natural), ceramic, etc. It will also be apparent from the description that the closing device has preferably the shape of a needle in the form of a loop or circle formed of a deformable shape memory alloy, e.g., Nitinol. As a general overview, the closing device of the present invention undergoes two positions of deformation: a first position in a compressed, straight configuration in which the closing device is captured in a closing device holder and deployed in the aperture and a second expanded round configuration in which the closing device approximates the aperture ends and closes the perforation in the tissue.

After the aperture in the tissue was prepared by the retracting device in order to form a slit, the two long sides of the slit are connected by the closing device to close the tissue opening.

Figures 1, 1A, 1B, 1C, 1D:
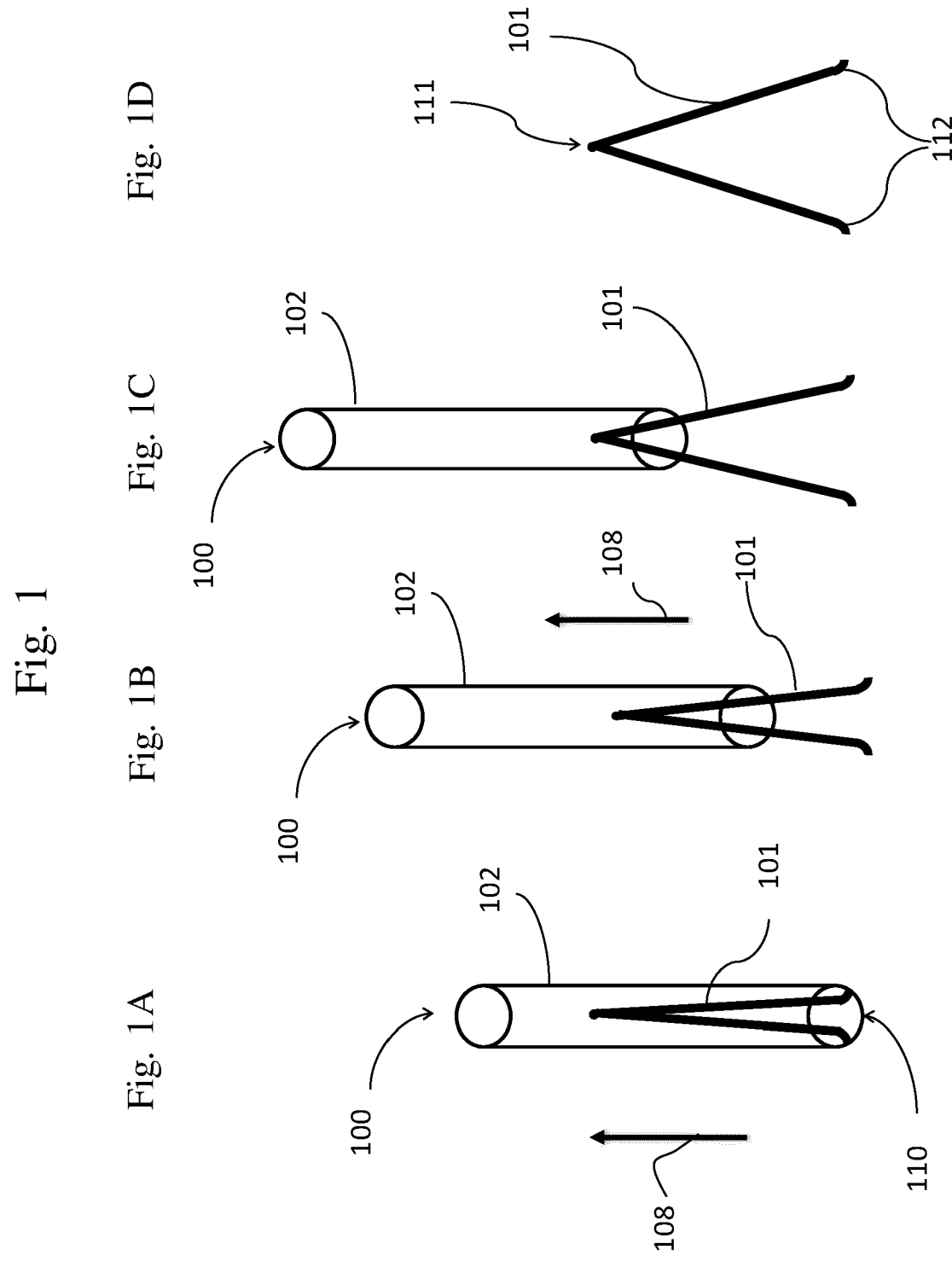
FIG. 1A to 1D are schematic side views of an embodiment of a retracting unit of a medical apparatus according to this invention.

FIG. 1 is a side view of the retracting unit 100 of this invention. The retracting unit 100 has optionally a longitudinal hollow retracting device holder 102 with a distal tip 110. A retracting device 101 is folded and is captured in the tubular retracting device holder 102. The retracting device 101 has a or one proximal end 111 and two distal ends 112. The retracting device 101 is optionally made of material with memory effect and has the ability to spread the two distal ends 112 apart like a spring. The retracting device 101 may be formed from a shape memory alloy, e.g., Nitinol, formed in the expanded stage or state as a triangular shape, that can be compressed in order to be captured in the retracting device holder 102. When the retracting device holder 102 is retracted along the arrow 108, the retracting device 101 is stepwise released and the distal ends 112 gradually spread due to the memory effect of the retracting device 101.

Figures 2, 2A, 2C, 2D, 2E, 2F:
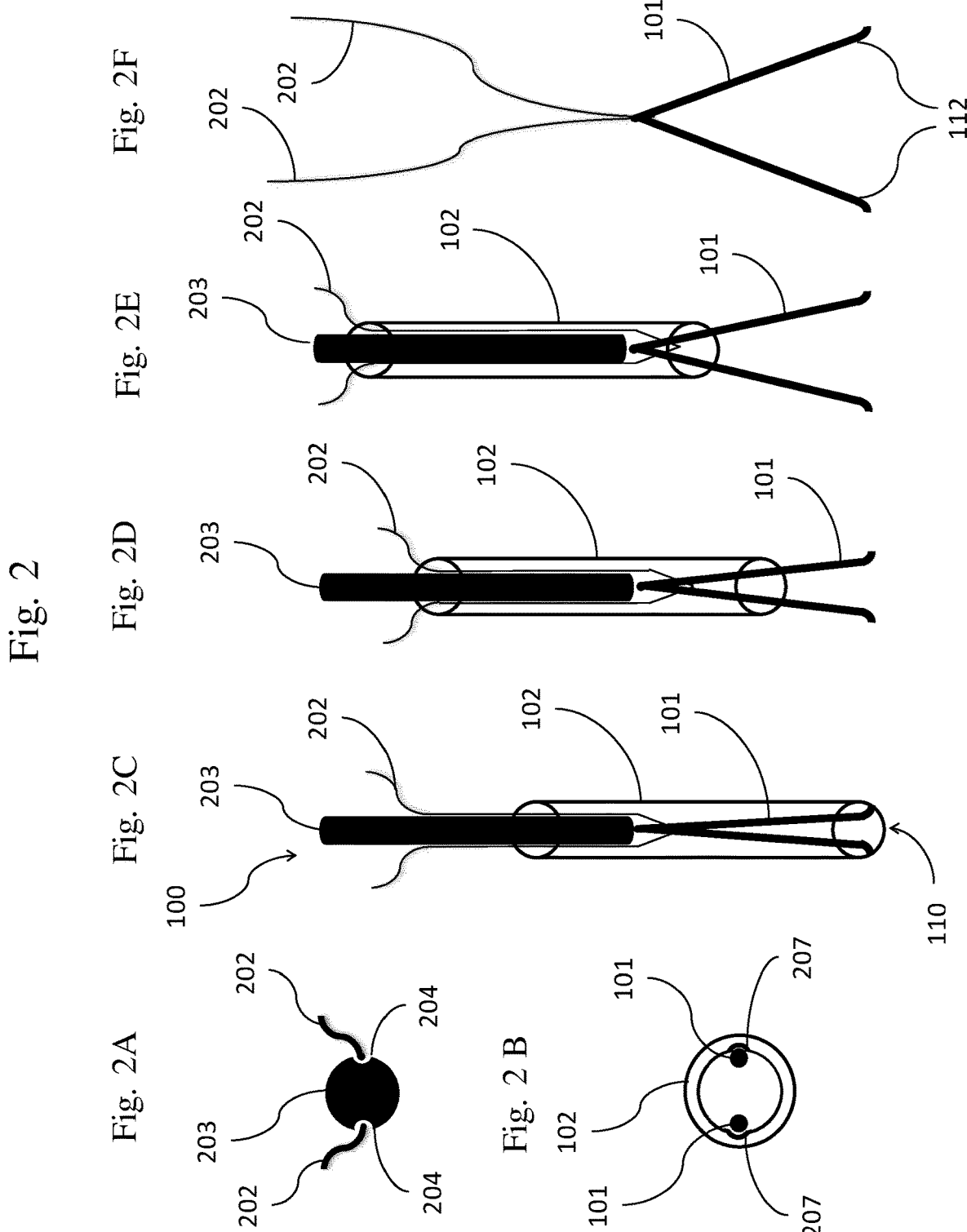

FIG. 2 is a side view of an alternative embodiment of the retracting unit 100 as shown in FIG. 1. The retracting unit 100 has a longitudinal hollow retracting device holder 102 with a distal tip 110. The retracting device 101 is folded and is captured in the tubular retracting device holder 102. In this embodiment, the retracting device holder 102 in cross-section has grooves 207 in which the arms of the retracting device 101 are captured and guided, when the retracting device 101 is moved in a longitudinal direction, in particular in the direction of the distal end of the retracting device holder 102. The retracting device 101 is pushed towards the distal end 110 of the retracting device holder 102 by, e.g., a piston 203 optionally captured in the retracting device holder 102. The retracting device 101 is looped by an optional suture 202, which tethers the retracting device 101. The piston 203 in a cross-section has grooves 204 in which the suture 202 is captured. When pushing the piston 203 in longitudinal direction from FIG. 2C to FIG. 2E, the retracting device 101 is stepwise released (FIG. 2C to FIG. 2F) and the distal ends 112 gradually spread due to the memory effect of the retracting device 101. During the longitudinal pushing towards the distal end 110 of the retracting device holder 102 or pulling away from the distal end 110 of the retracting device holder 102 by the piston 203, the retracting device 101 remains connected to the piston 203 by the tethering suture 202 or a similar acting component. Once the retracting device 101 is fully released, the retracting device holder 102 including the piston 203 may be removed, leaving the retracting device 101 still tethered by the suture 202. Later, the retracting device 101 can be removed from its position (aperture) by pulling on both ends of the suture 202.

Figure 3:
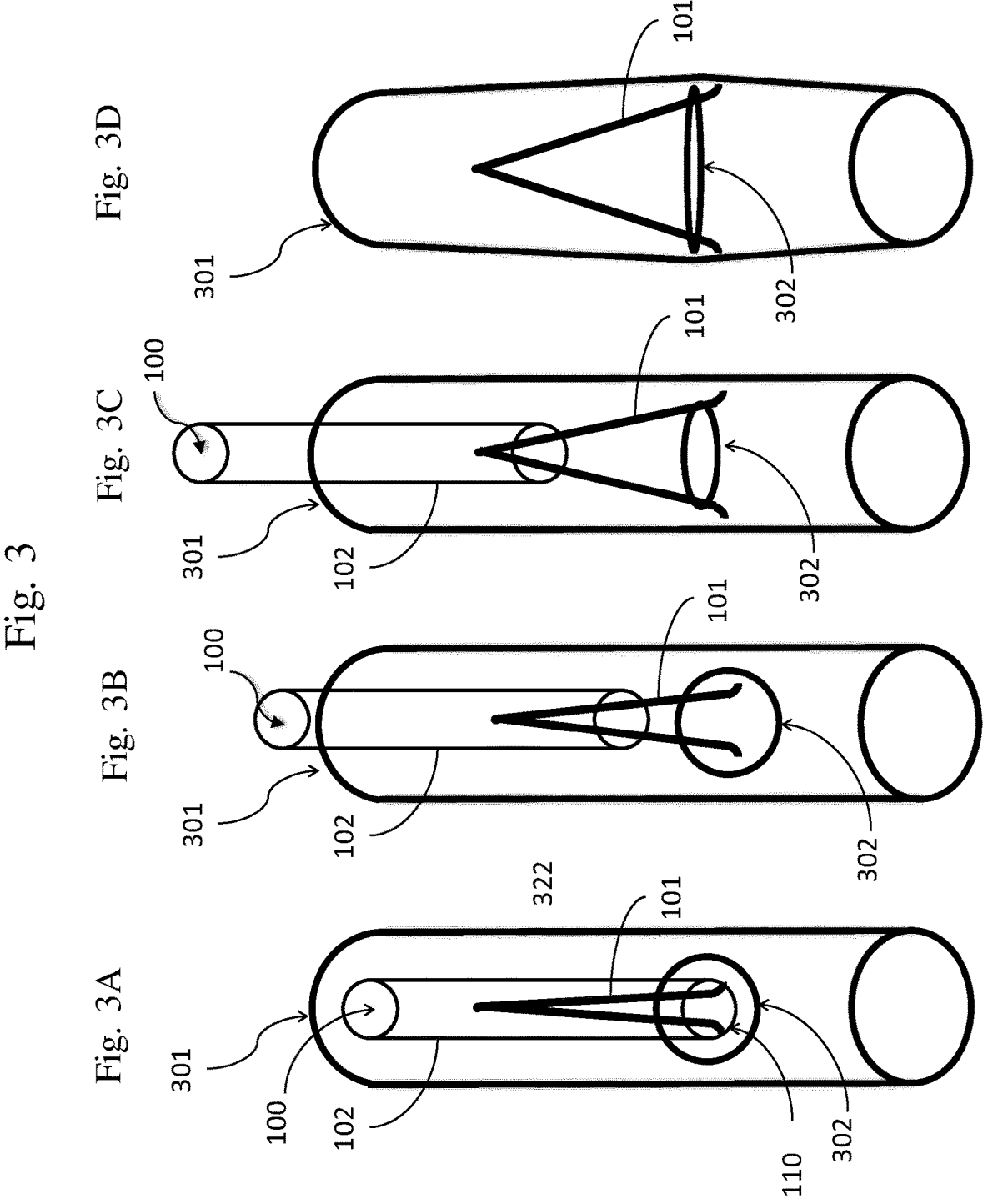
FIG. 3A to 3D are schematic, partially sectioned views of a retracting unit deployed within an aperture.

FIG. 3 is a schematic, partially sectioned view of a retracting unit 100 deployed within a vessel aperture 302.

The retracting unit 100 is developed such that it can be deployed through the wound in the patient's body through a casing which characteristically will extend from outside the patient's body with its distal end within the lumen of the vessel 301 through the aperture 302 to be closed.

The retracting unit 100 and the retracting device 101 vary in dimension according to the size of the aperture 302 and size of a vessel 301 or other body organ in a patient that is to be closed and upon the material composition of the units and devices.

The retracting unit 100 having a retracting device holder 102 and capturing a retracting device 101 is inserted in the aperture 302 of the vessel 301. Once the distal end 110 of the retracting device 101 is deployed below the vessel wall aperture 302, the retracting device holder 102 is stepwise retracted in a direction away from the vessel aperture 302 (from FIG. 3A to FIG. 3D) and the retracting device 101 is released. Due to the memory properties of the retracting device 101 the aperture 302 is gradually spread from FIG. 3B to FIG. 3D in a direction orthogonal to the vessel long axis and becomes a slit opening 302 in FIG. 3D in the vessel wall 301.

Figure 4:
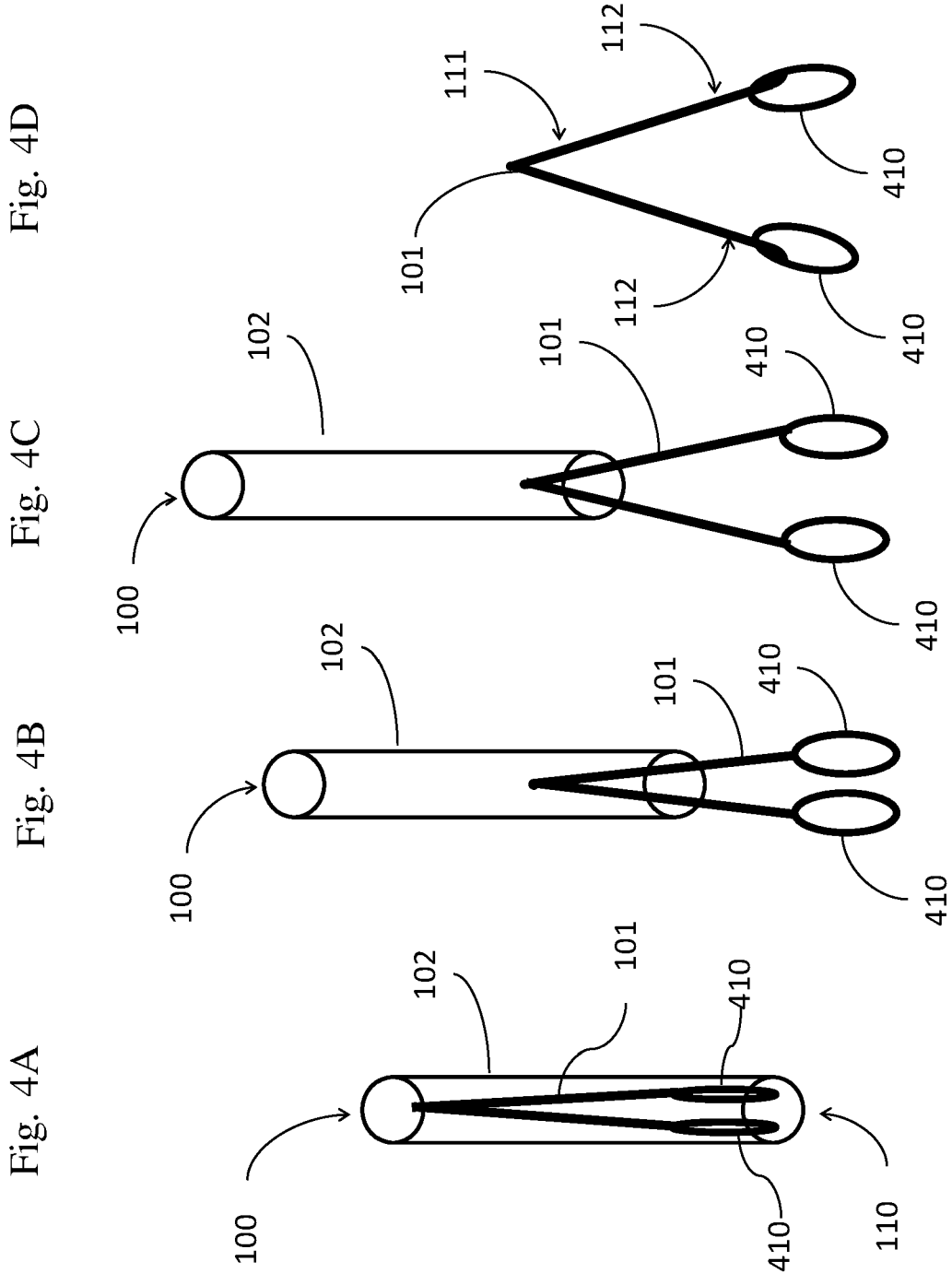
FIG. 4A to 4D are side views of an alternative embodiment of retracting unit.

FIG. 4 is a side view of an alternative embodiment of retracting unit 100 as shown in FIG. 1. The retracting unit 100 has a longitudinal hollow retracting device holder 102 with a distal tip 110. The retracting device 101 is folded and is captured in the tubular retracting device holder 102. The retracting device 101 has a proximal end 111 and two distal ends 112 with an optional engaging device 410 at each of the two distal ends 112. The engaging device 410 is preferably a looped element, preferably a wire loop, that is formed initially in an expanded state and can be folded and captured in the retracting device holder 102. The retracting device 101 is optionally made of material with memory effect like memory alloy, e.g., Nitinol and has the ability to spread the two distal ends 112 and unfold the wire loop 410. When the retracting device holder 102 is retracted along the arrows (from FIG. 4B to FIG. 4D) the retracting device 101 is stepwise released and the two arms 112 of the retracting device 101 spread and the distal engaging members 410 unfold due to the memory effect of the retracting device 101.

Figure 5:
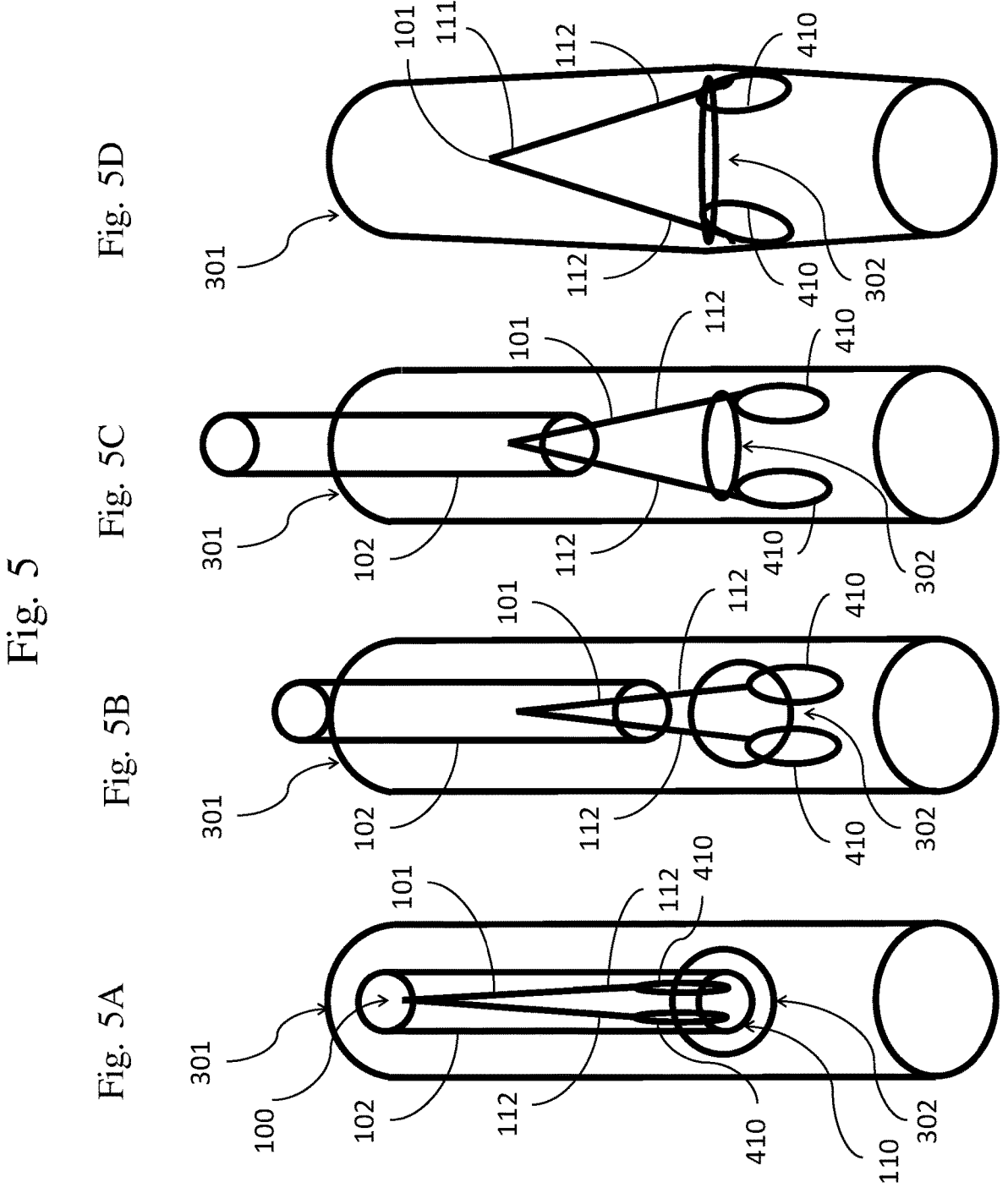
FIG. 5A to 5D are schematic, partially sectioned side views of the retracting unit deployed within the aperture.

FIG. 5 is a schematic, partially sectioned side view of the retracting unit 100 deployed within the aperture 302 of a vessel 301.

The retracting unit 100 is developed such that it can be deployed through the wound in the patient's body through a casing which characteristically will extend from outside the patient's body with its distal end within the lumen of the vessel 301 through the aperture 302 to be closed.

The retracting unit 100 and the retracting device 101 vary in dimension according to the size of the aperture 302 and size of a vessel 301 or other body organ in a patient that is to be closed and upon the material composition of the units and devices.

The retracting unit 100 having a retracting device holder 102 and capturing a retracting device 101 is inserted in the aperture 302 of a vessel 301. The retracting device 101 has a proximal end 111 and two distal ends 112 with an engaging member 410 at each of the two ends 112. The engaging member 410 is preferably a wire loop that can be folded and captured in the retracting device holder 102. Once the distal end 110 of the retracting device holder 102 is deployed below the vessel wall aperture 302, the retracting device holder 102 is stepwise retracted in direction away from vessel aperture 302 (from FIG. 5A to FIG. 5B) releasing the engaging devices 410 (FIG. 5D) that unfold below the vessel aperture 302 and engage the vessel inner wall surrounding the opening. The engaging devices 410 are further released from FIG. 5B to FIG. 5C. Due to the memory properties of the engaging devices 410 the aperture 302 is gradually spread (from FIG. 5B to FIG. 5D) and becomes a slit opening 302 (FIG. 5D) in the vessel wall 301. The unfolded engaging devices 410 prevent a retraction of the engaging devices 410 out of the vessel aperture 302 when in a slit shape.

Figures 6, 6A, 6B:
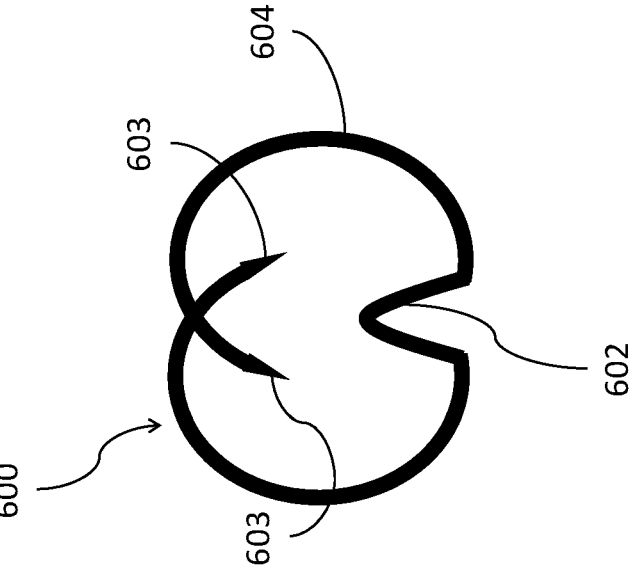
FIGS. 6A and 6B are face views of a closing device of a medical apparatus according to an embodiment of this invention in a preferred expanded round form of a needle and a compressed straight form.

FIG. 6 is a face view of a closing device 600 of this invention in a preferred form of a round needle. The closing device 600 has a proximal end 602 and first and second arms 604 with each optionally having a pointed distal end 603. Both arms 604 are the bending portions of the closing device 600.

The closing device 600 has an expanded substantially closed position (FIG. 6A) with both arms 604 forming each a hemi-circle or semi-circle in optionally or substantially one plane allowing both arms 604 to cross each other and a compressed substantially closed position (FIG. 6B) whereas the arms 604 are substantially linear allowing the closing device 600 to be captured in a retracting device holder 102 (FIG. 5) or closing member 800.

The closing device 600 can be made of various preset memory shape materials, with the material selection depending upon the particular need.

The closing device 600 may be formed of any biocompatible material including, for example, Titanium (and Titanium alloys), Nitinol, stainless steel, polymeric materials (synthetic and/or natural), ceramic, etc. and/or may bioabsorbable material, for example, galvanic corrosion may be utilized. The decomposition rate may be adjusted by way of the composition not forming any macroscopic gas bubbles. The closing device 600 is preferably made of shape memory alloy, e.g., Nitinol and has the ability to form a loop like structure. The size of the closing device 600 depends upon the material composition of the needle and the required size for use. Depending on the application, the closing device 600 can have dimensions and cross-sectional dimensions ranging from 10 micro-millimeters to 10 centimeters. The size will depend on the target closure size and the size of the aperture 302 to be closed.

Figure 8:
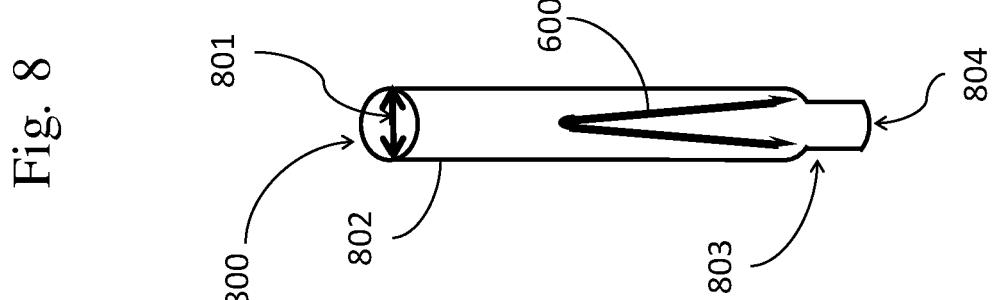
FIG. 8 is a schematic side view in longitudinal direction of a closing member containing the straight folded (being understood as compressed or not deployed) closing device captured in a closing device holder.

Preferably, the expanded looped closing device 600 (FIG. 6A) may be resiliently compressed into its compressed state (FIG. 6B), e.g., by constraining it with the closing member 800 as shown in FIG. 8.

Figures 13, 13A, 13B, 13C, 13D, 13E, 13F, 13G, 13H:
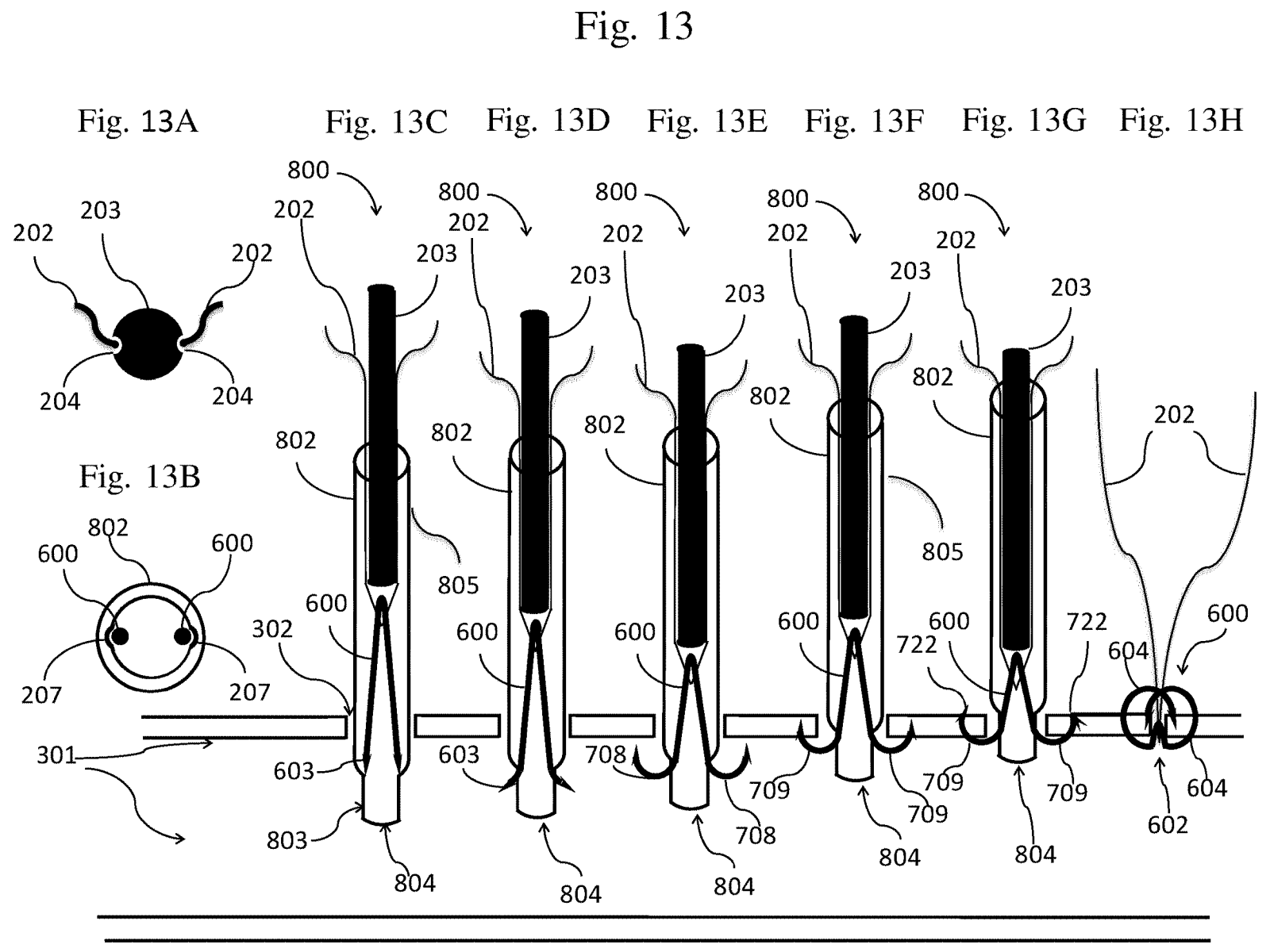

The closing device 600 may be deployed from a contracted state (FIG. 6B) to an expanded state as shown in FIG. 6A. When in a partially expanded state, the closing device 600 can be used like an anchor to locate its position by withdrawing the partially expanded closing device 600 in the aperture 302 to be closed until the hook like formed closing device 600 perforate the wall, and further withdrawing can be detected as an increasing resistance to further withdrawal (as shown in FIG. 13 F).

Figures 7, 7A, 7B, 7C, 7D, 7E, 7F:
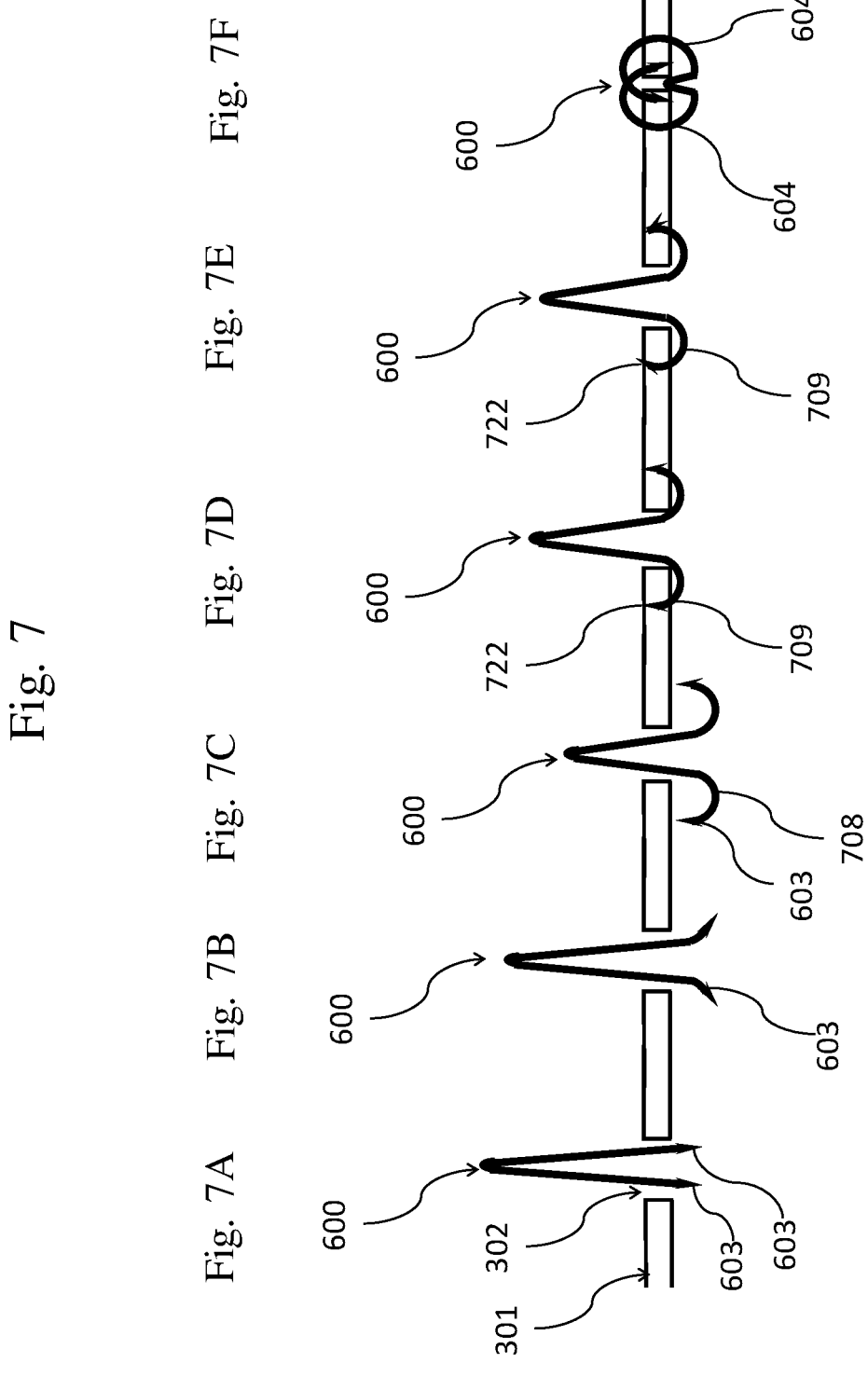
FIG. 7A to 7F are side views of a closing device as shown in FIG. 6 deployed in the aperture, penetrating the tissue and connecting the free edges of the aperture.

The closing device 600 has pointed ends 603 that will engage one side of the aperture wall surrounding the opening 302, penetrate the wall of the aperture 302 and the anchor like bent arms 604 will approximate the perforated tissue wall as shown in FIG. 7. A groove 602 in the expanded closing device 600 (see FIG. 6A) that represents the proximal end 602 of the closing device 600 in FIG. 6B allows for locking the closing device 600 to the closing member 800 as shown infra in FIG. 13.

FIG. 7 is a side view of a closing device 600 as shown in FIG. 6 deployed in the aperture 302, penetrating the tissue 301 and connecting the free edges of the aperture 302.

FIG. 7 shows the subsequent deployment of the closing device 600 from FIG. 6 in an aperture 302 to be closed.

In FIG. 7A the closing device 600 (as shown FIG. 6), is in a compressed straight configuration and advanced in the aperture 302 of the tissue 301.

In FIG. 7B the closing device 600 is partially deployed, the tip of the closing device 603 is bent due to the memo-material effect.

In FIG. 7C with further deployment of the closing device 600 the end of the closing device 603 is bent further into an anchor form 708 with the pointed ends of the closing device 603 engaging one side of the tissue aperture 301 and penetrating (see 709) the wall 301.

The closing device 600 is then withdrawn, and the pointed ends 722 of the anchor like formed closing device 708 perforate the tissue 301. Further deployment of the closing device 600 will cause the closing device 600 to complete each of both bend arms hemi-circle or semi-circle, approximating the tissue aperture ends and closing the aperture 302.

It should be understood, however, that deployment of the closing device 600 optionally requires a closing device holder 802 as shown in the subsequent FIG. 8 to FIG. 12. It should be understood, that more closing devices 600 could be utilized depending upon the embodiment and organization of the closing devices 600.

FIG. 8 is a schematic, sectioned side view of the closing member 800 in longitudinal direction 801 comprising a longitudinal hollow closing device holder 802 with a distal end 804. The closing device holder 802 contains the straight compressed closing device 600. The closing device holder 802 has optionally a lateral channel 803 for the deployment of the closing device 600.

Figure 9:
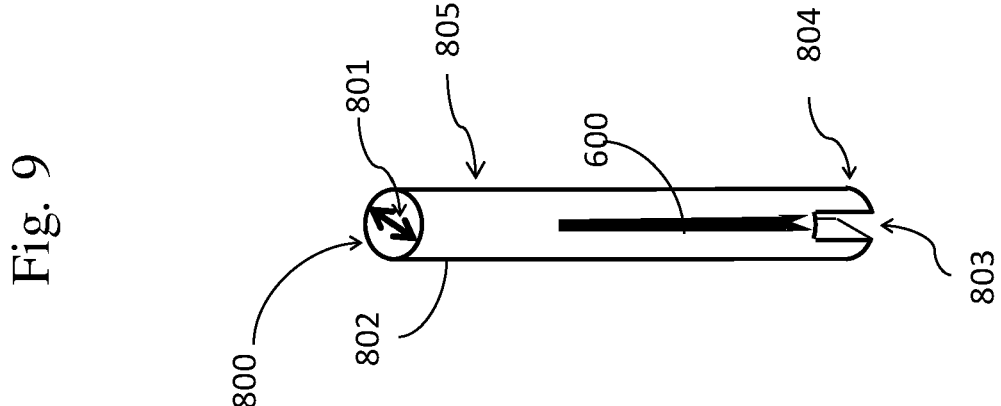
FIG. 9 is a schematic perspective view of the closing member containing the straight folded closing device captured in a closing device holder.

FIG. 9 is a schematic, sectioned perspective side view indicated by the arrow 801 of the closing device holder 802 as shown in FIG. 8, containing the straight folded closing device 600. The closing device holder 802 has optionally a lateral channel 803 for the deployment of the closing device 600. The channel 803 allows the closing device 600 to exit the closing device holder 802 in a bent way, as shown in FIG. 12B to FIG. 12D in the form of an anchor 708 (in FIG. 12C), but preventing the closing device 600 from engaging structures and tissue that might be positioned opposite to the end 804 of the closing device holder 802 like an opposite vessel wall.

Figure 10:
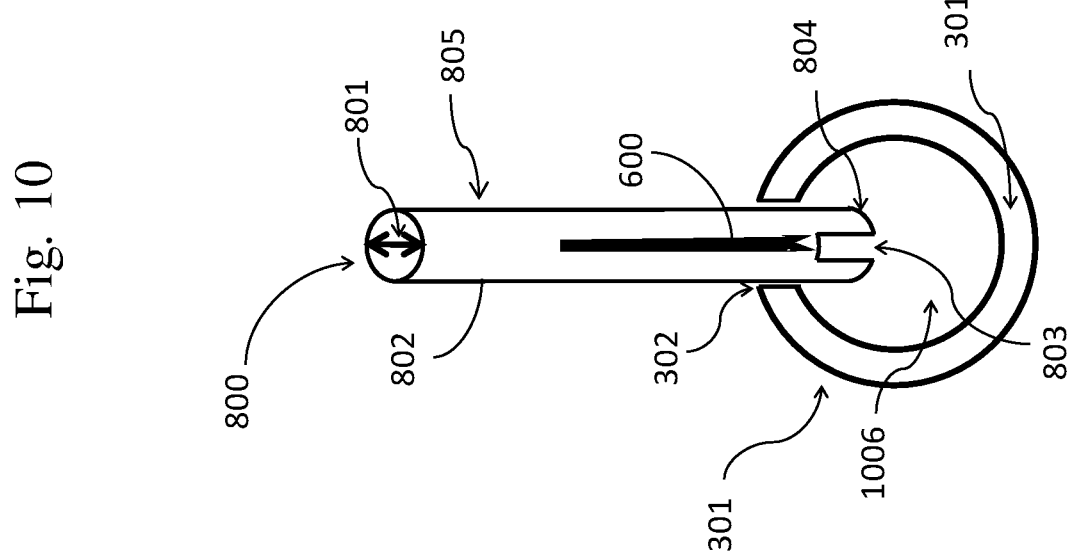
FIG. 10 is a schematic, partially sectioned longitudinal cross-section view of the closing member deployed within the aperture of a vessel.

FIG. 10 is a schematic, partially sectioned perspective view indicated by the arrow 801 of a vessel 301 and the closing device holder 802, as shown in FIG. 8 and FIG. 9, containing the straight folded closing device 600 and being advanced into a vessel lumen 1006 through the aperture 302 in the vessel wall 301. The channel 803 in the distal closing device holder 802 allows the closing device 600 to exit the closing device holder 102 in a bent way as shown in FIG. 12B to FIG. 12D in form of an anchor 708 (in FIG. 12C) preventing the closing device from engaging an opposite vessel wall 301.

Figure 11:
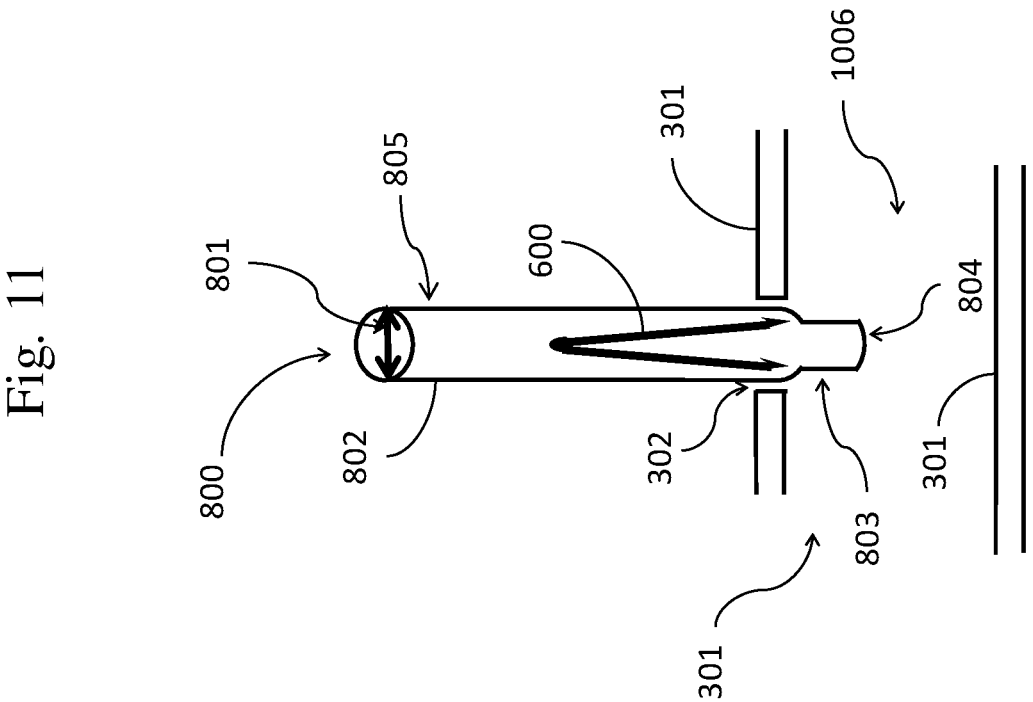
FIG. 11 is a schematic, partially sectioned longitudinal cross-section view of the closing member advanced into the aperture of a vessel.

FIG. 11 is a schematic, partially sectioned perspective view indicated by the arrow 801 of a longitudinal transection of a vessel 301 and the closing device holder 802 as shown in FIG. 8, FIG. 9 and FIG. 10 containing the straight compressed closing device 600 and being deployed in a vessel lumen 1006 through the aperture 302 in the vessel wall 301. The channel 803 in the distal closing device holder 802 allows for the closing device 600 to exit the closing device holder 102 in a bent way as shown in FIG. 12B to FIG. 12D, e.g., in the form of an anchor 708 (in FIG. 12C) preventing the closing device from engaging the opposite vessel wall 301.

Figures 12, 12A, 12B, 12C, 12D, 12E:
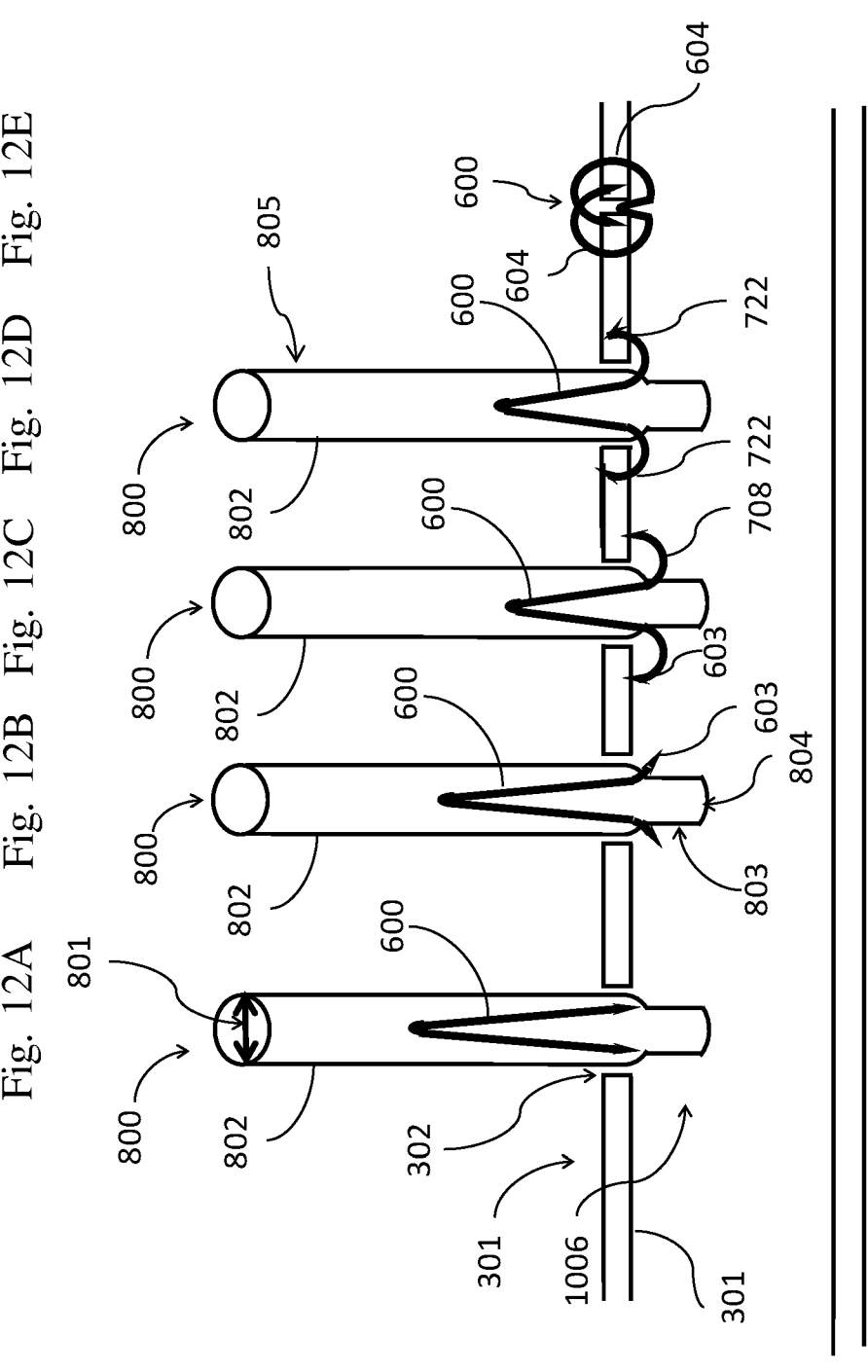
FIG. 12A to 12E are schematic, partially sectioned longitudinal cross-section views of the closing member from FIG. 10 and the closing device from FIG. 6 deployed in the aperture, penetrating the tissue and connecting the free edges of the aperture.

FIG. 12 is a schematic, partially sectioned longitudinal cross-section view as indicated by the arrow 801 of the closing device holder 802 from FIG. 8 and FIG. 9 in the sequence from FIG. 12A to FIG. 12E showing the closing device holder 802 from FIG. 8 deployed in the aperture FIG. 12A.

In FIG. 12B the closing device 600 is pushed outward in the direction of the end 804 of the closing device holder 802 and the tips of the closing device 603 bend and leave the closing device holder 802 in the channel 803.

In FIG. 12C the closing device 600 is pushed further in direction of the end 804 of the closing device holder 802, further leaving the closing device holder 802 through the channel 803 and optionally forming an anchor 708. The tips 603 of the closing device 600 are engaging the vessel wall 301.

In FIG. 12D the closing device holder 802 is further withdrawn out of the aperture 302. The anchor 708 has pointed ends 722 perforating the vessel wall 301. Further withdrawing can be detected as a firm resistance to yet further withdrawal. The closing device holder 802 is then further retracted out of the vessel aperture 302 and the closing device 600 is released. The arms 604 of the closing device 600 bend inward, pulling the ends of the aperture 302 together, closing the aperture 302 and forming a ring structure as shown in FIG. 6.

FIG. 13 is a schematic, partially sectioned longitudinal cross-section view of an alternative closing member 800 deployed in the aperture 302 in the wall of a vessel 301. FIG. 13 shows the sequence FIG. 13C to FIG. 13H of the deployment of the closing device 600 and the closure of the aperture 302 achieved by the closing device 600. In this embodiment, the closing member 800 captures a piston 203.

FIG. 13A shows the piston 203 in cross-section, having grooves 204 in which a holding device 202, preferably a suture, is guided. The holding device 202 is tethering the closing device 600 to connect the piston 203 with the closing device 600.

FIG. 13B shows the closing device holder 802 as shown in FIG. 8 in cross-section, having grooves 207 in which the arms of the closing device 600 are captured and guided, when the closing device 600 is moved in longitudinal direction, in particular in the direction to the distal end 804 of the closing device holder 802. The closing device 600 is pushed towards the end 804 of the closing device holder 802 by the piston 203 as shown in the sequence FIG. 13C to FIG. 13H.

In FIG. 13C the end of the closing member 800 is deployed in the aperture 302 in the wall of the vessel 301. The closing member 800 and the closing device 600 are oriented in the longitudinal direction of the vessel 301 as shown in FIG. 8 by the arrow 801.

In FIG. 13D the piston 203 is pushed towards the distal end 804 of the closing device holder 802 and the tips of the closing device 600 exit from the closing device holder 802 through the channel 803 and bend outwards. The holding device 202 follows the forward movement to the end 804 of the closing device holder 802 while keeping the closing device 600 and the piston 203 tightly connected.

In FIG. 13E the closing device 600 is pushed further by the piston 203 in direction of the distal end 804 of the closing device holder 802, further leaving the closing device holder 802 through the channel 803 and forming an anchor 708. The tips 603 of the closing device 600 engage the vessel wall 301 and penetrate the vessel wall 301.

In FIG. 13F the closing device holder 802 together with the closing device 600 are withdrawn, and the pointed ends 603 of the partially released closing device 600, formed like an anchor 708, perforate (see: 722) the vessel wall 301. Further withdrawing of the anchor-like shaped closing device 600 can be detected as a firm resistance to yet further withdrawal.

Further pushing the piston 203 towards the end 804 of the closing device holder 802 will cause the closing device 600 to complete with each of both arms 604 hemi-circles or semi-circles, approximating the tissue aperture ends and closing the aperture 302 somewhat like a single suture for closing the aperture 302 as shown in FIG. 13H.

Once the closing device 600 is released, the closing device holder 802 including the piston 203 is removed, leaving the unfolded closing device 600 still tethered by the holding device 202. The holding device 202 could then be utilized for localizing or even retracting the closing device 600 if needed. When the result of the closing the aperture 302 is satisfactory, the holding device 202 is removed, e.g., by pulling one arm of the holding device 202.

The following descriptions combine the retracting unit 100 and the closing member 800 in one set or medical apparatus, deployed simultaneously or subsequently. The sequence from FIG. 14 to FIG. 21 shows the closure of an aperture 302 with two closing members 800.

Figure 14:
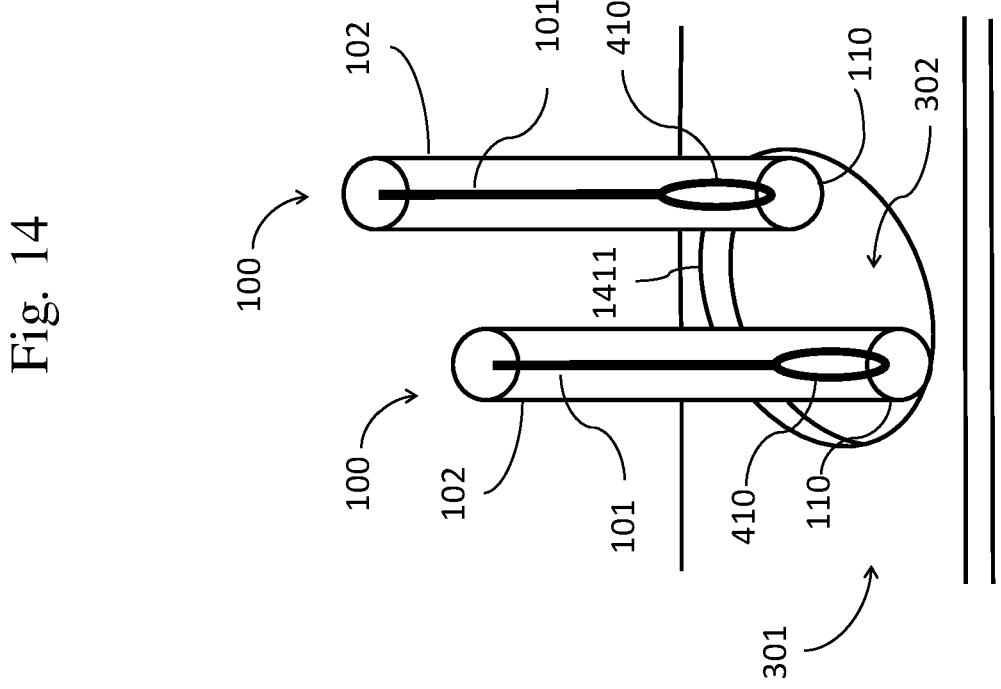
FIG. 14 is a schematic, partially sectioned perspective view of two retracting units advanced into the aperture.

FIG. 14 is a schematic, partially sectioned perspective view of an alternative embodiment of a retracting unit 100 as shown in FIG. 5. The retracting unit 100 has two retracting device holders 102 each of them capturing one retracting device 101 having distally connected an engaging device 410.

The engaging device 410 is preferably a wire loop that can be folded and captured in the retracting device holder 102.

The distal ends 110 of two retracting device holders 102 are deployed in opposite sides of the aperture 302 in a tissue 301.

Figure 15:
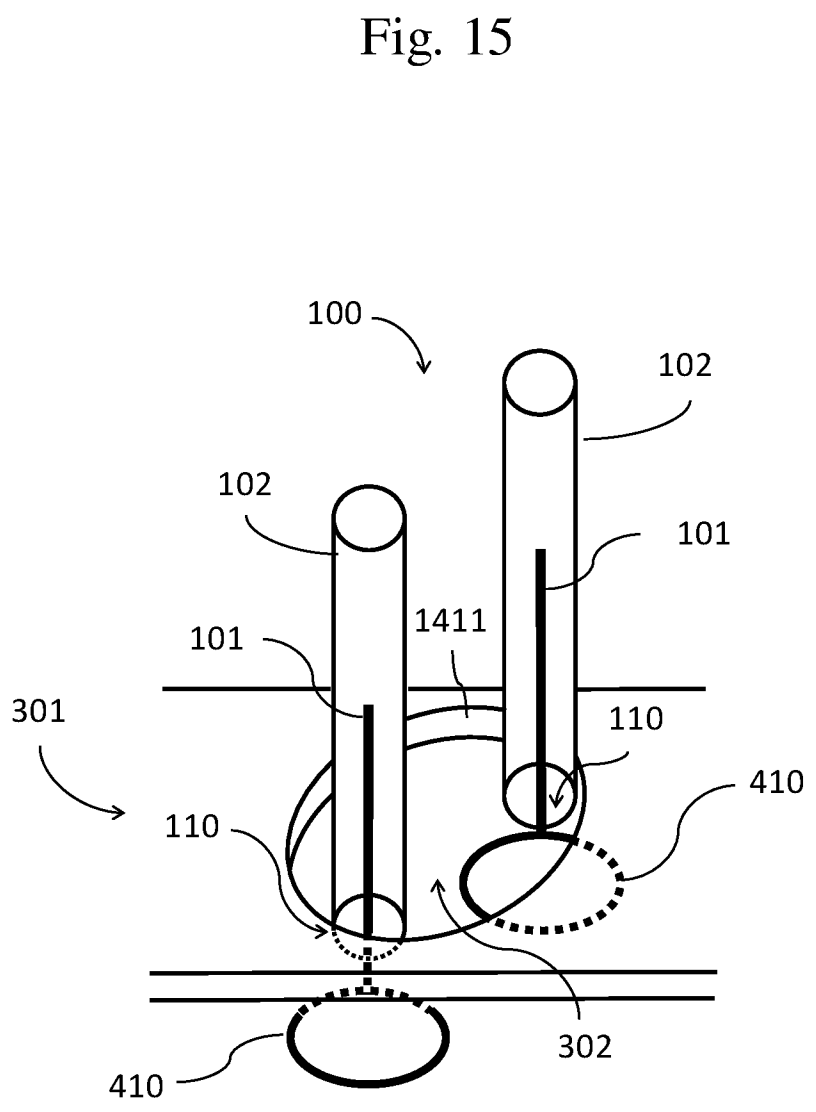

FIG. 15 is a schematic, partially sectioned perspective view of two retracting devices 101 in the aperture opening 302 with the ends 110 positioned on opposite sides of the aperture 302 below the aperture wall 1411. The retracting devices 101 were pushed forward to the distal ends 110. The engaging devices 410 have left the opening at the distal ends 110 of the retracting device holders 102 and the engagement devices 410 have unfolded into a loop.

Figure 16:
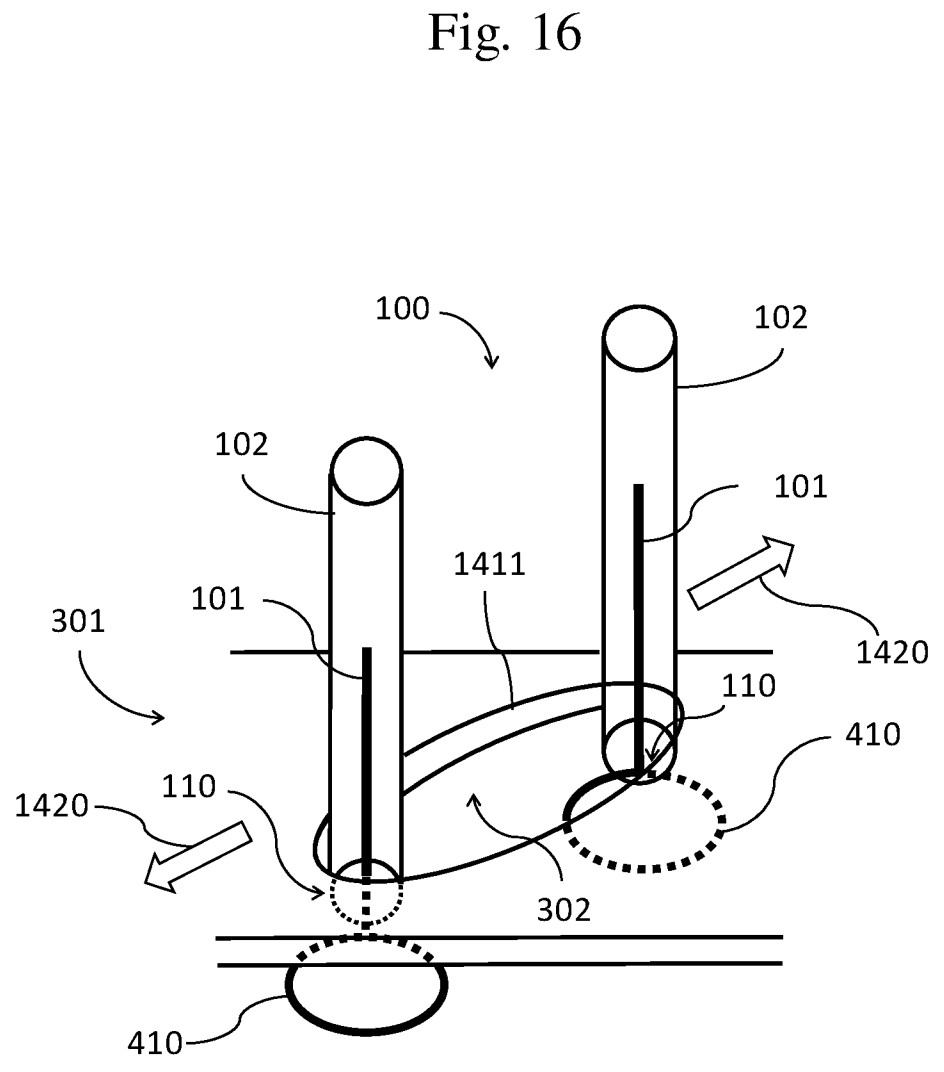

FIG. 16 is a schematic, partially sectioned perspective view of two retracting units 100 in the aperture opening 302 with the distal ends 110 positioned on opposite sides of the aperture 302 below the aperture wall 1411. The two retracting device holders 102 with the engaging devices 410 are moved in opposite direction as indicated by the arrows 1420.

Figure 17:
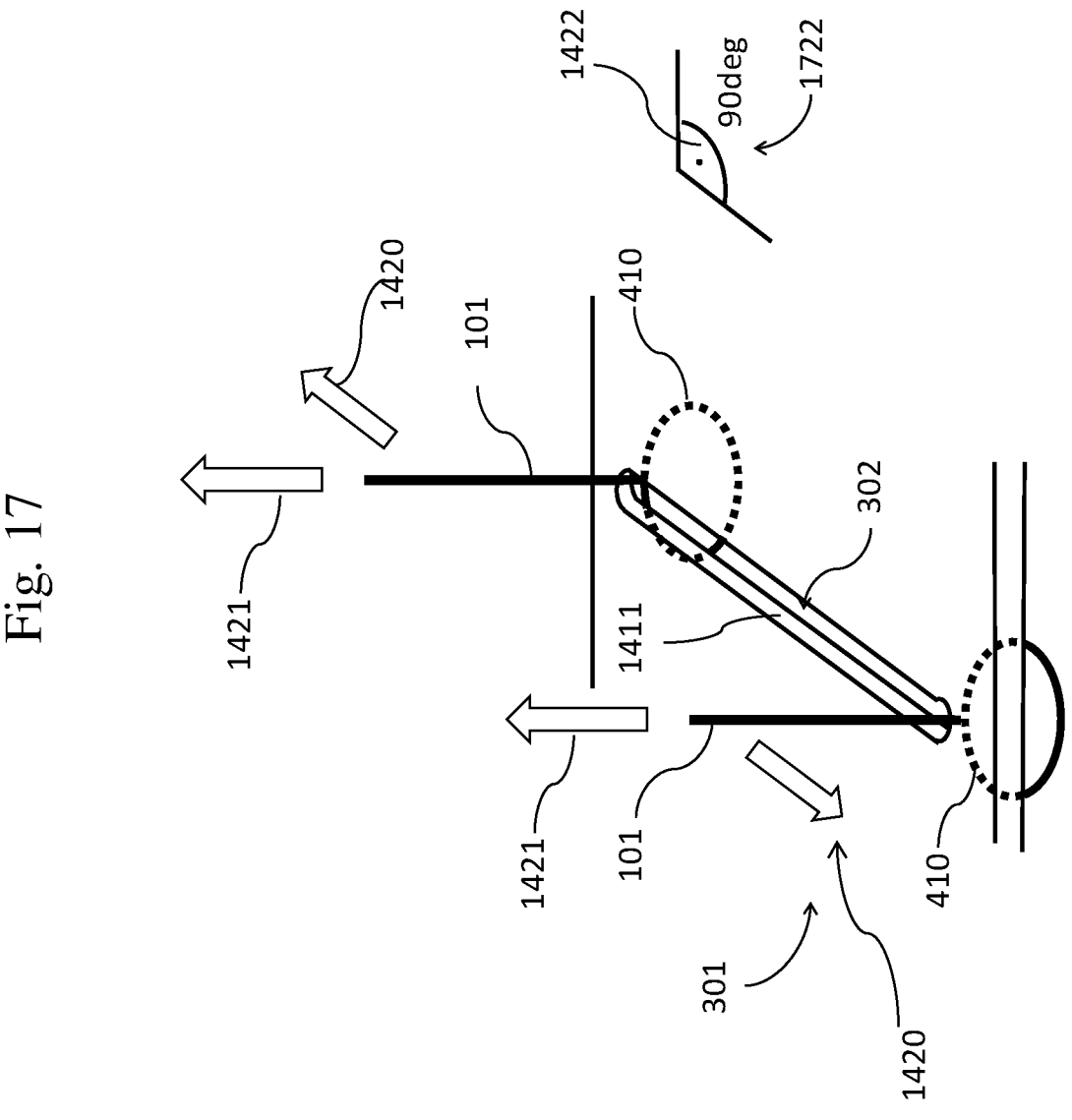
FIG. 17 is a schematic, partially sectioned perspective view of two retracting units deployed within the aperture, the two retracting devices from FIG. 4 advanced and deployed within the vessel, the two retracting devices are retracted until a stop is felt and the aperture is spread until the aperture becomes a straight slit and can be felt to stop.

FIG. 17 is a schematic, partially sectioned perspective view of two retracting devices 101, deployed in the aperture opening 302 with the distal ends 110 positioned on opposite sides of the aperture 302, below the aperture wall 1411. The two retracting devices 101 are moved in opposite direction, as indicated by the arrows 1420, causing the aperture 302 to form a slit. The opposite movement of the retracting devices 101 will come to a stop when the opening of the aperture 302 forms a straight slit, e.g., with the length of the slit being equal to half of the circumference of the aperture 302 as shown in FIG. 15. The engaging devices 410 form a loop with a diameter that is larger than the short axis of the slit opening of the aperture 302 in an angle 1422 of 90 deg to the slit opening. The engagement means 410 would lock an accidental upwards movement 1421 of the retracting units as indicated by the arrows 1420. The upward movement 1421 of the retracting devices 101 is stopped when the engagement device 410 comes into contact and cannot pass through the slit opening of the aperture 302.

Figure 18:
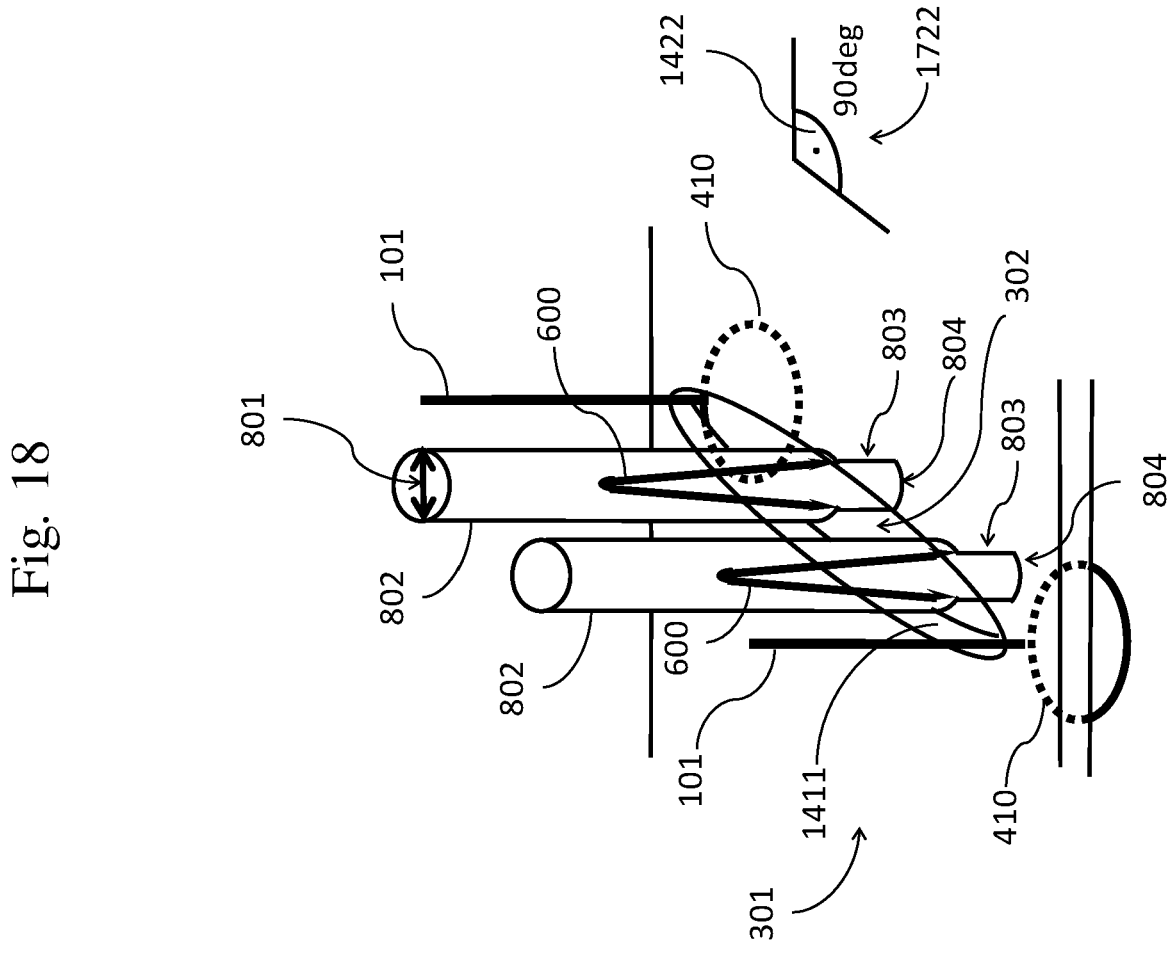
FIG. 18 is a schematic, partially sectioned perspective view of two retracting devices and two closing devices simultaneously or subsequently deployed within the aperture.

FIG. 18 is a schematic, partially sectioned perspective view of two retracting devices 101 and two engaging devices 410 deployed in the aperture opening 302 as shown in FIG. 16 having transformed the aperture into a slit form with simultaneous or sequential deployment of the closing member 800, with the two closing device holders 802 between the aperture shoulders, with the ends 804 and the channels 803 positioned below the opening of the aperture 302. The closing devices 600 are captured and compressed in the closing device holders 802 and orientated in an angle of 90 deg to the aperture opening 302 as indicated by the protractor 1722 and the arrow 801.

Figure 19:
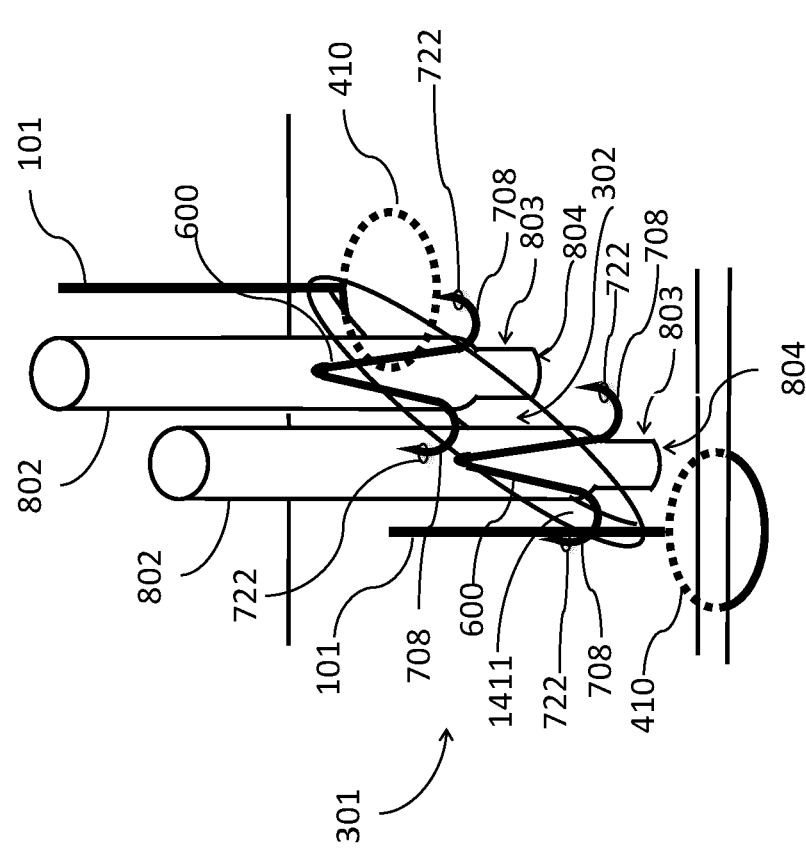
FIG. 19 is a schematic, partially sectioned perspective view of two retracting devices and two closing devices deployed within the aperture, the aperture is retracted and the aperture long edges are approached by the partially deployed closing device from FIG. 6.

FIG. 19 is a schematic, partially sectioned perspective view of two retracting devices 101 with the engaging devices 410 and closing device holders 802 deployed in the aperture opening 302 as shown in FIG. 18. The closing devices 600 are stepwise released in the direction to the closing device holder ends 804 and have left the closing device holders 802 in the channels 803, forming anchors 708 that have engaged the wall of the tissue 301, surrounding the opening 302 and the tips 603 of the closing device 600, and perforated the wall of the tissue 301 as shown at the perforations 722. Further withdrawing can be detected as a firm resistance to further withdrawal. The closing device holders 802 are then further retracted out of the vessel aperture 302, and the closing devices 600 are released.

Figure 20:
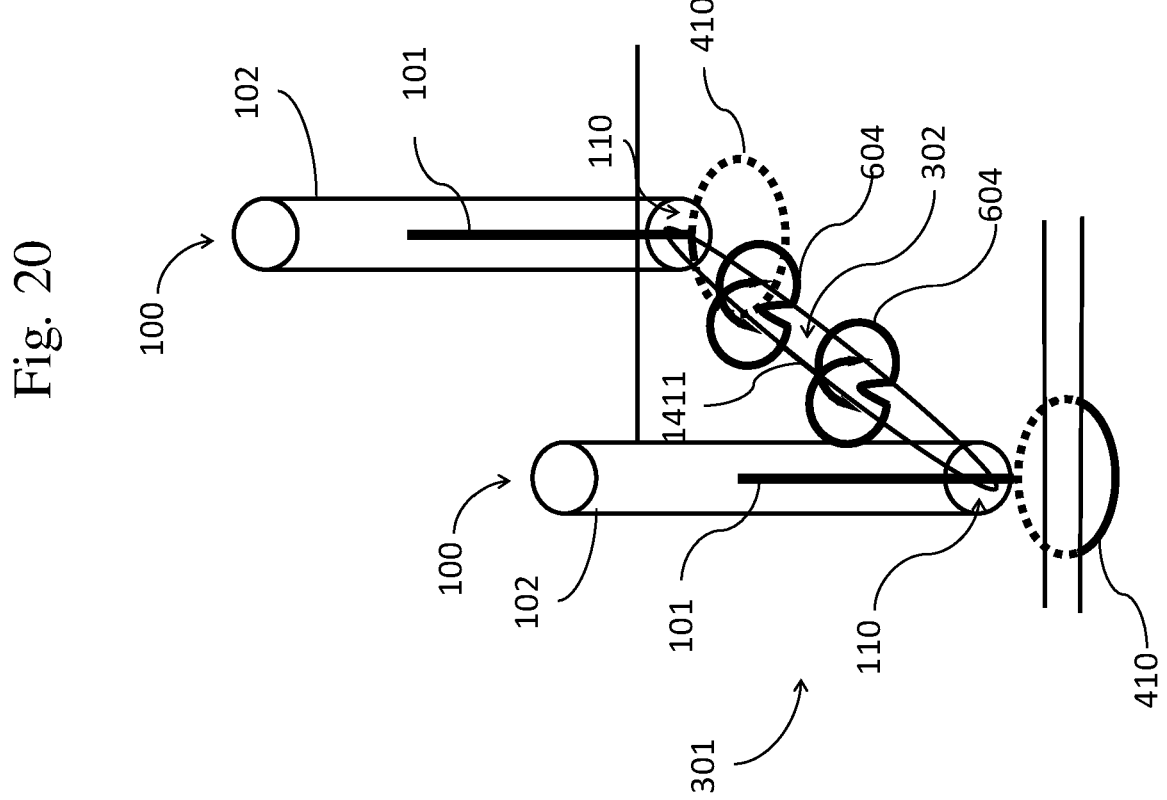
FIG. 20 is a schematic, partially sectioned perspective view of two retracting devices and two closing devices from FIG. 6 fully deployed and connecting the long edges of the aperture, the retracting units are subsequently retracted.

FIG. 20 is a schematic, partially sectioned perspective view of two retracting device holders 102, partially retracted out of the aperture 302, while the engaging devices 410 are still deployed in the aperture 302. The closing device holders 802 as shown in FIG. 19 are removed. The closing devices 600 as shown in FIG. 19 are fully unfolded forming the structure as shown in FIG. 6A. The closing devices 600 do approximate and close the aperture's 302 free edges 1411.

Figure 21:
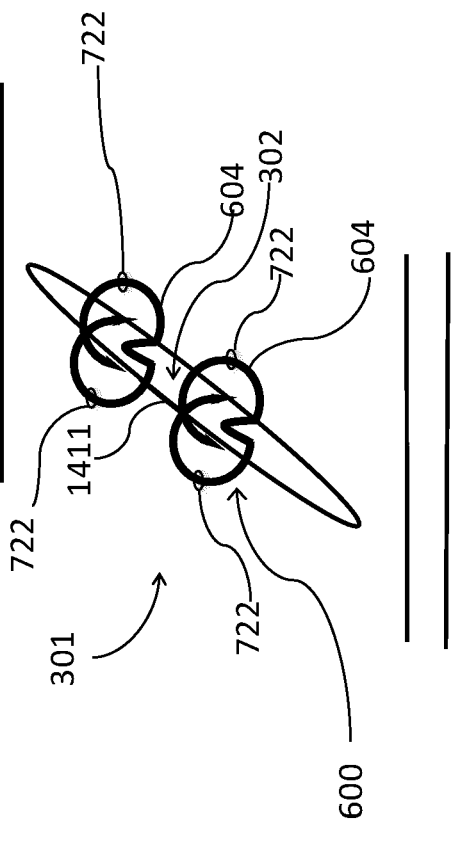
FIG. 21 is a schematic perspective view of the two released closing devices from FIG. 6 closing the aperture in a transverse line.

FIG. 21 is a schematic perspective view of the tissue 301 having a closed aperture 302. The aperture's 302 sides are approximated and closed by the closing device 600 that perforate the tissue as indicated by the perforations 722.

The following descriptions combine the retracting unit 100 and the closing member 800 in one set or medical apparatus, deployed simultaneously in a vessel 301. The sequence from FIG. 22 to FIG. 25 shows the closure of an aperture 302 in a tissue with one closing device 600.

Figure 22:
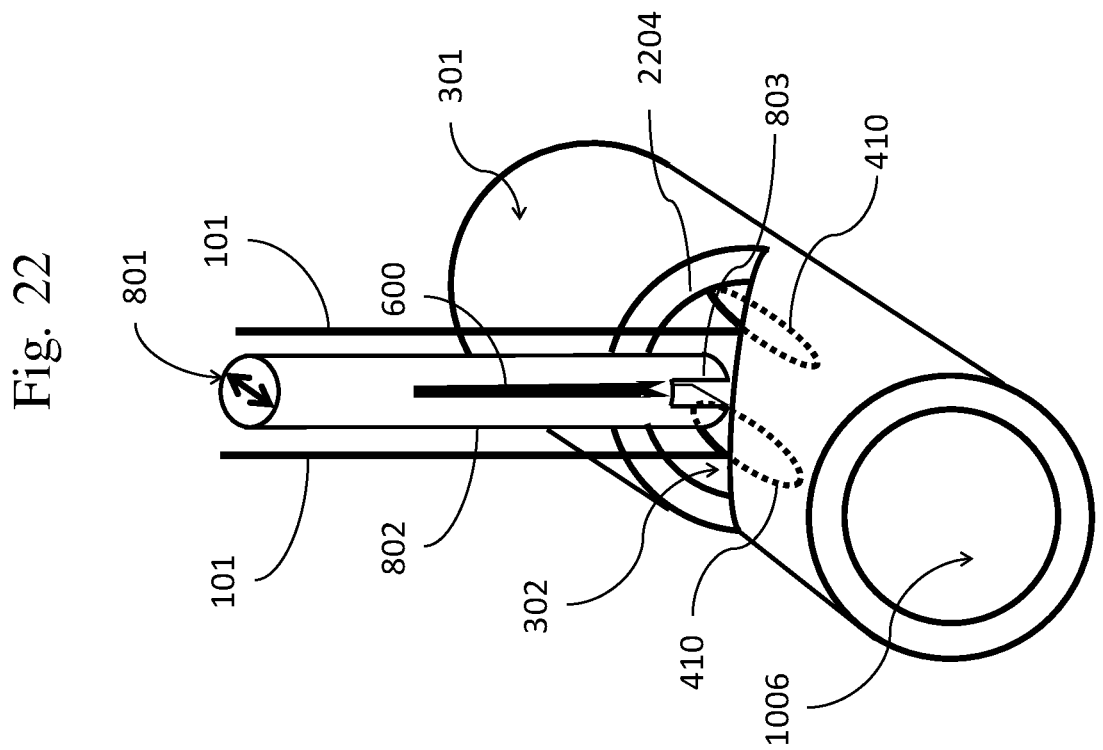
FIG. 22 is a schematic, partially sectioned perspective view of two retracting devices and one closing member simultaneously advanced into the aperture of a vessel.

FIG. 22 is a schematic, partially sectioned perspective view of two retracting devices 101, with the engaging devices 410 and one closing device holder 802 deployed in the aperture 302 in the wall 2204 of a vessel 302 within the vessel lumen 1006. The engaging devices 410 are positioned inside of the vessel lumen 1006 oriented in longitudinal direction of the vessel 301, as indicated by the arrow 801. Simultaneously, the closing device holder 802 is deployed between the retracting devices 101, with the opening of the channel 803 below the aperture wall 2204 inside of the vessel lumen 1006, oriented in longitudinal direction of the vessel 301 as indicated by the arrow 801.

Figure 23:
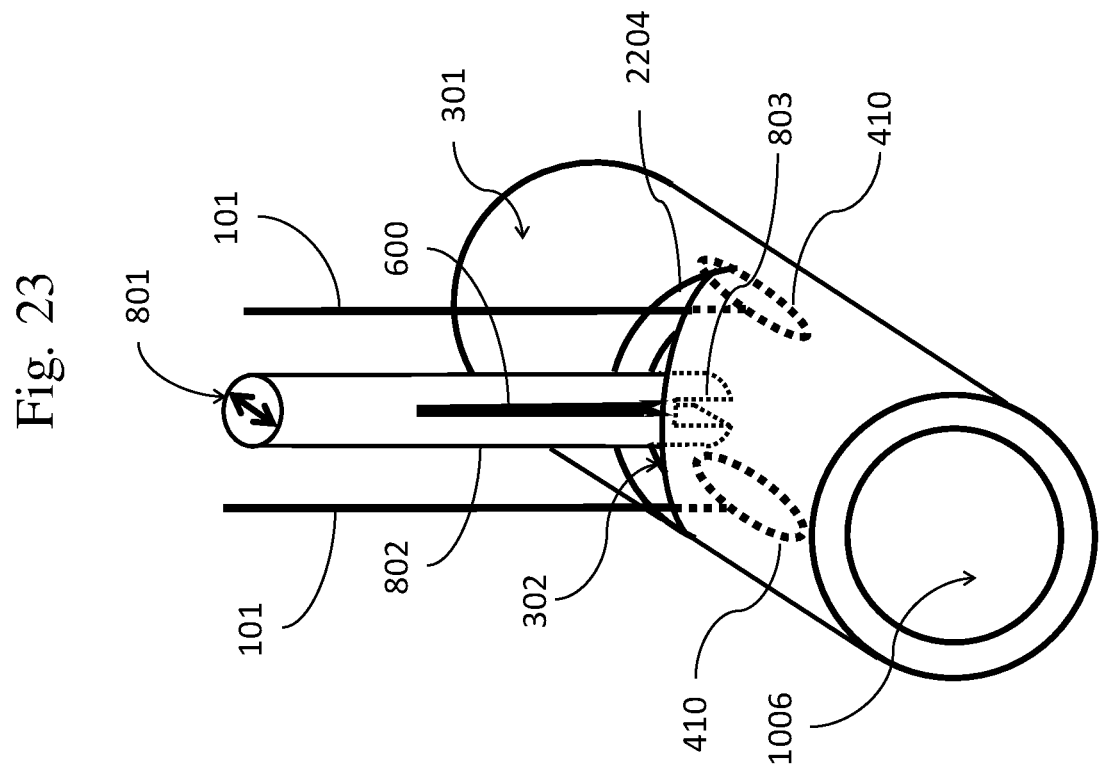
FIG. 23 is a schematic, partially sectioned perspective view of two retracting devices and one closing member deployed within the aperture of a vessel, the aperture is retracted in a direction orthogonal to the vessel long axis.

FIG. 23 is a schematic, partially sectioned perspective view of two retracting devices 101 with the engaging devices 410 and one closing device holder 802 deployed in the aperture 302 in the wall 2204 of a vessel 302. The engaging devices 410 and the channel 803 of the retracting device holder 102 are positioned below the aperture wall 2204 inside of the vessel lumen 1006. The retracting devices 101 and the engaging devices 410 are moved apart in a transverse direction which is orthogonal to the vessel's long axis. The engaging devices 410 press against the inner wall of the vessel 301 in opposite direction. This will retract the opposing sides of the aperture 302 and spread the aperture 302 of the vessel 301 in a direction orthogonal to the long axis of the vessel 301, at the same time approximating the opposing expanded long sides of the aperture 302.

Figure 24:
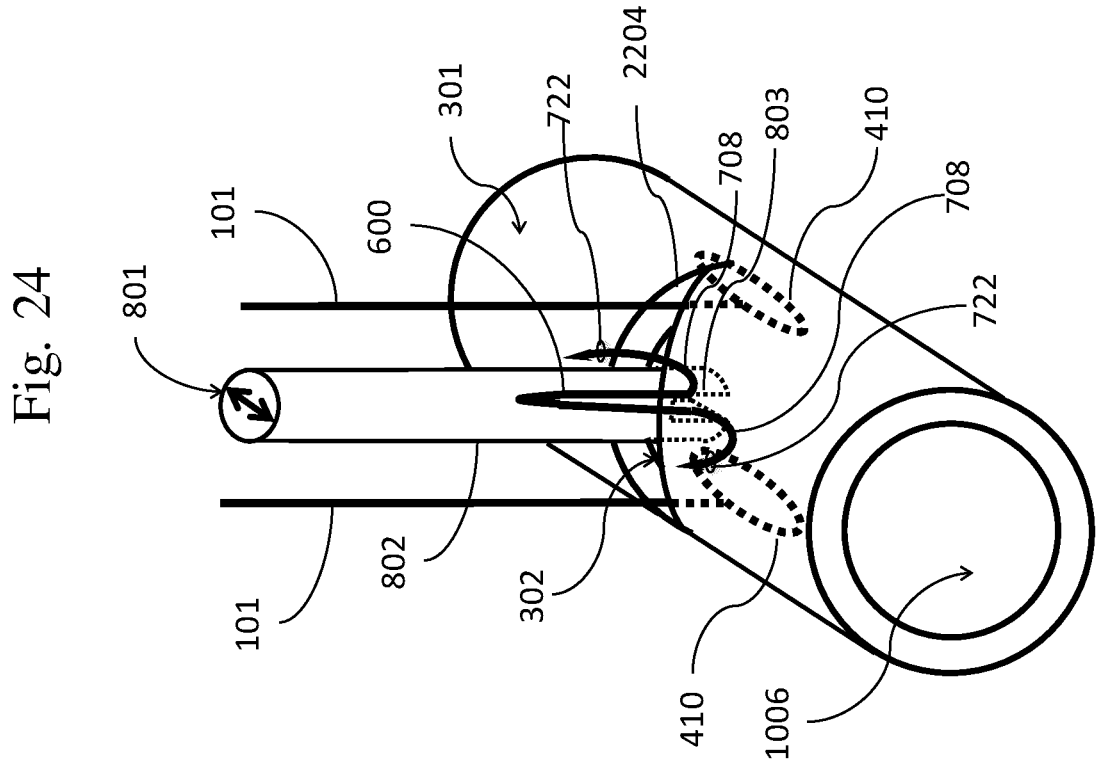
FIG. 24 is a schematic, partially sectioned perspective view of two retracting devices and one closing member further advanced into the aperture of a vessel, the aperture is retracted in a direction orthogonal to the long axis of the vessel and the aperture long edges are approached and penetrated by the partially deployed closing device from FIG. 6.

FIG. 24 is a schematic, partially sectioned perspective view of two retracting devices 101 with the engaging devices 410 and one closing device holder 802 deployed in the aperture 302 in the wall 2204 of a vessel 301. The engaging devices 410 and the channel 803 of the retracting devices 101 are positioned below the aperture wall 2204, inside of the vessel lumen 1006. The retracting devices 101 and the engaging devices 410 have retracted the aperture 302 in a direction orthogonal to the long axis of the vessel 301, causing approximation of the opposing long extended sides of aperture 302. The closing device 600 is partially deployed, has left the closing device holder 802 via the channel 803 and has formed an anchor 708 that has sufficiently grasped the vessel wall 2204 and penetrated the vessel wall 2204 as indicated by the perforation 722. Further withdrawing can be detected as a firm resistance to further withdrawal. The closing device holder 802 is then further retracted out of the vessel aperture 302 and the closing device 600 is released, forming the complete round structure, pulling the aperture wall 2204 and approximating the aperture opposing long extended sides 2204 further together. Eventually the closing device holder 802 is withdrawn and removed and the retracting devices 101 are removed by pulling the engaging devices 410 out of the closed aperture 302, while the flexible loops of the engaging devices 410 collapse and slip through the shoulders of the already closed aperture 302.

Figure 25:
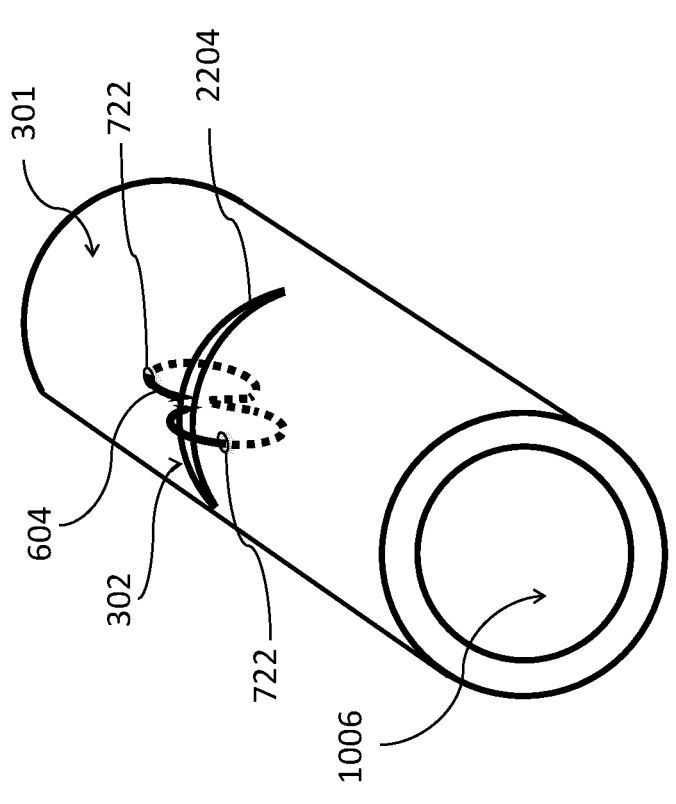
FIG. 25 is a schematic, partially sectioned perspective view of the vessel with one closing device closing the aperture.

FIG. 25 is a schematic, partially sectioned perspective view of a vessel 301 having an aperture 302 that was closed in a straight line, orthogonal to the vessel's long axis by the closing device 600 with perforations 722 of the aperture wall 2204.

Figure 26:
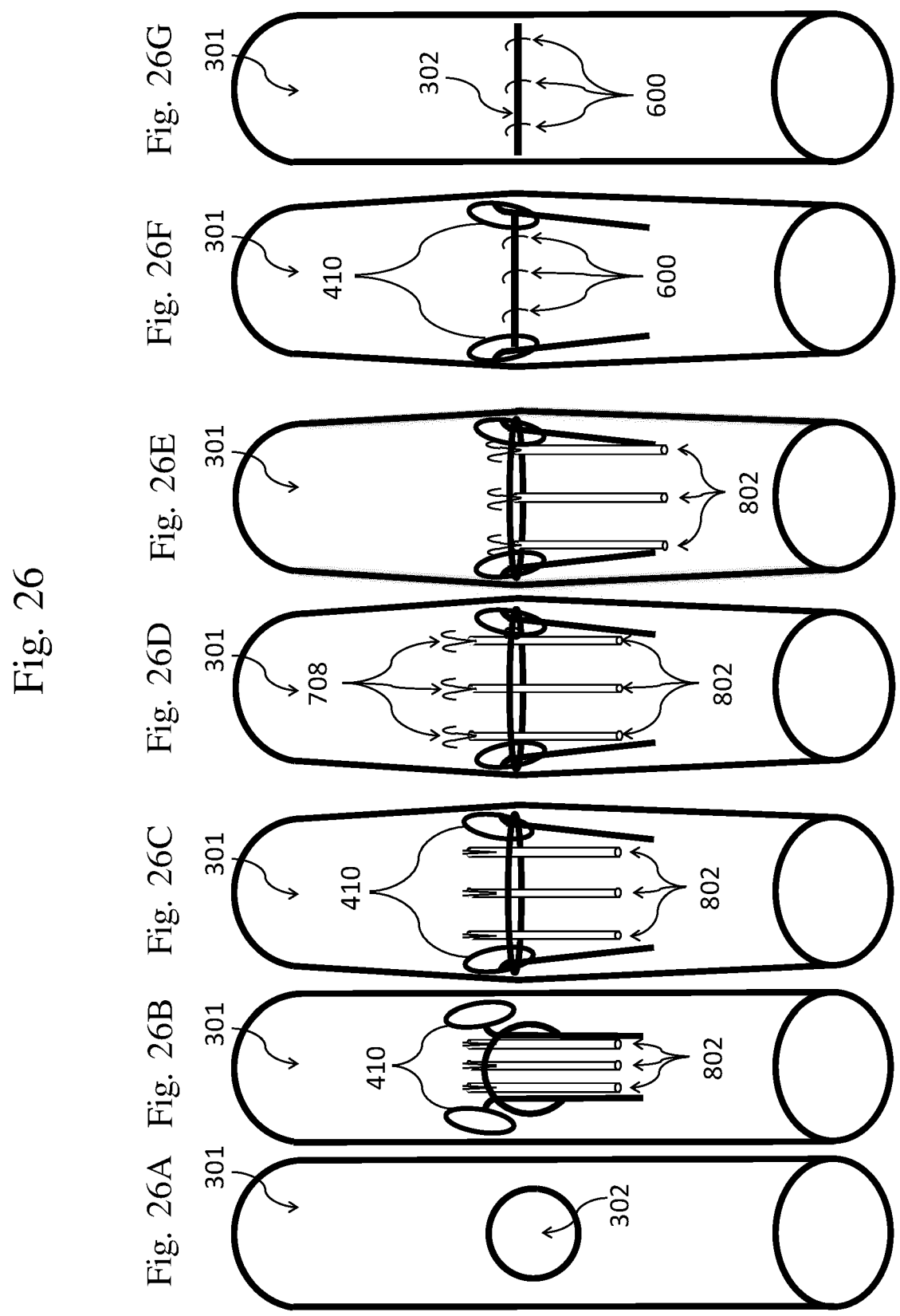
FIG. 26A to FIG. 26G are schematic, partially sectioned perspective views of the entire procedure in seven steps (a-g) of closing a vessel aperture.

FIG. 26 is a schematic, partially sectioned view from the operator's perspective showing the closure of an aperture 302 in a patient vessel.

In FIG. 26B the retracting unit 100 with two arms and the closing member 800 with three closing device holders 802 are deployed in an aperture 302 of a patient's vessel.

In FIG. 26C the engaging devices 410 are moved apart in transverse direction orthogonal to the long axis of the vessel at the opposite sides of the aperture 302, retracting the sides of the aperture 302, which results in an approximation of the upper and lower end of the aperture 302 and in forming a slit opening with two long sides, distal and proximal, and two short sides at the lateral side of the vessel. Simultaneously the closing device holders 802 are moved apart, to be equally distributed along the spread aperture 302.

In FIG. 26D the closing devices 600 are deployed and form an anchor each.

In FIG. 26E the closing device holders 802 are retracted and the closing devices 600 engage, and, upon further retracting the closing device holders 802, perforate the wall of the vessel 301 surrounding the opening 302. Further withdrawing can be detected as a firm resistance against yet further withdrawal. The closing device holders

802 are then further retracted out of the vessel aperture 302 and the closing devices 600 are released.

In FIG. 26F the closing devices 600 are deployed forming round needles that are closing the aperture 302.

In FIG. 26G the engaging devices 410 are retracted. The closing devices 600 close the transverse seam of the aperture 302.

Figure 27:
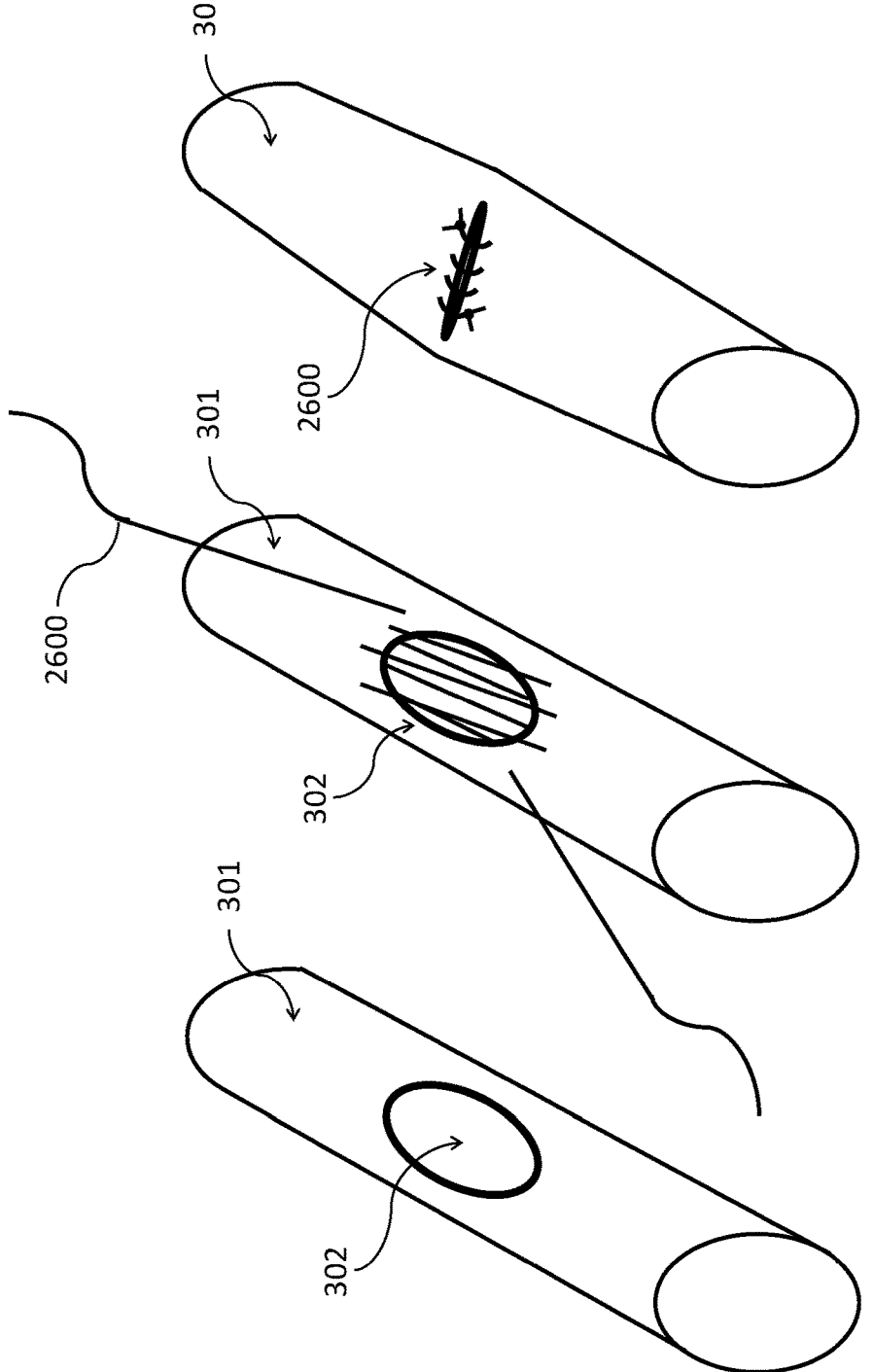
FIG. 27 shows the aperture in the patient's vessel and the closing with a transverse surgical suture.

FIG. 27 is a surgeon view of the aperture 302 of a patient's vessel 301, showing the open surgical closure of the aperture 302 with a suture. The aperture 302 in the patient's vessel 301 is closed in a straight line orthogonal to the vessel's long axis, with a running or interrupted suture 2600 to avoid a stenosis of the patient's vessel. This principle of closing an aperture in a patient vessel is of particular importance and is realized in this invention as shown in FIG. 10-FIG. 12 and FIG. 22-FIG. 26 which illustrate an exemplary method of operating the medical apparatus.

Figure 28:
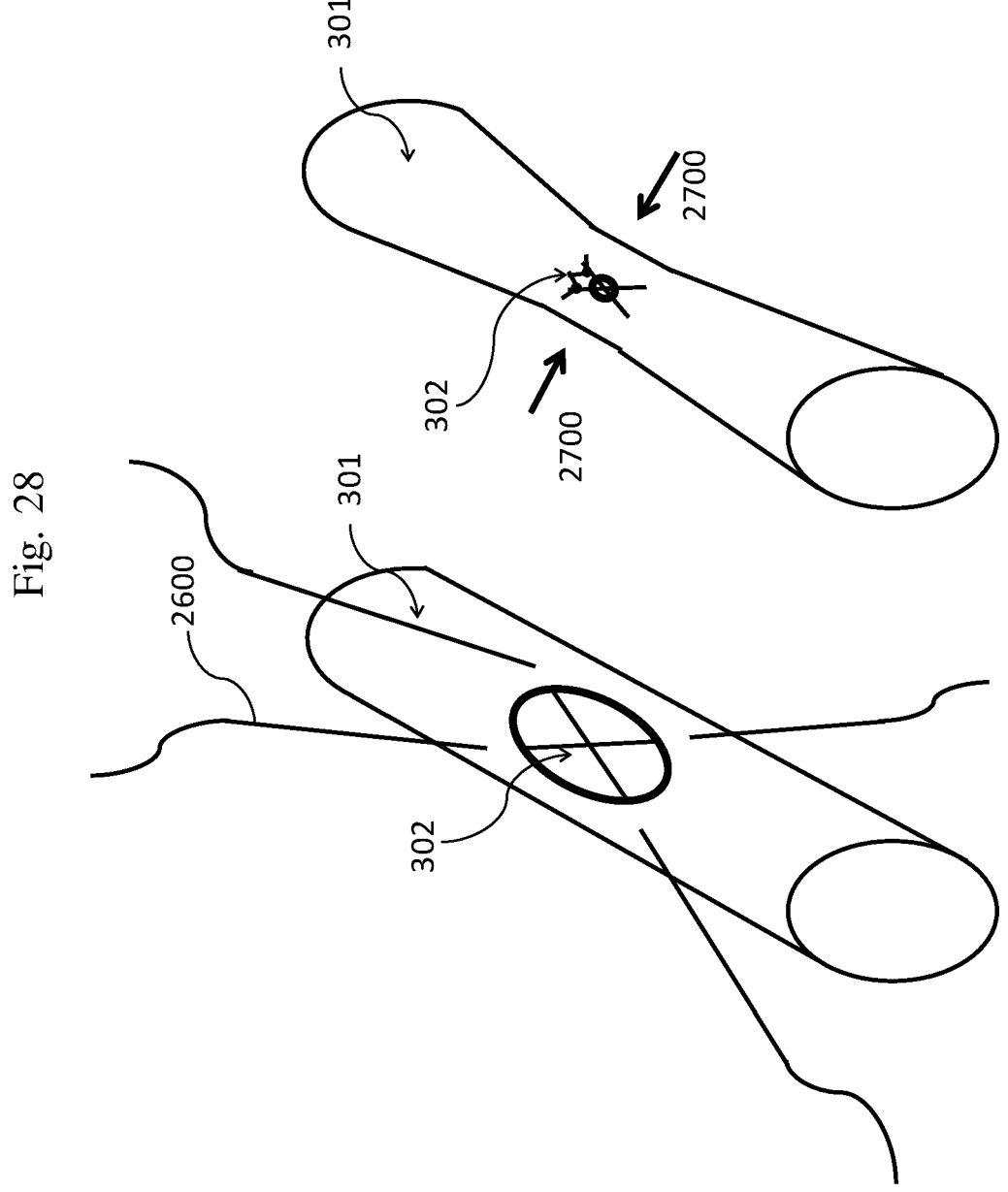
FIG. 28 shows the aperture in the patient's vessel and the closing with a cross surgical procedure.

FIG. 28 is a surgeon view of the aperture 302 of a patient's vessel 301 showing the open surgical closure of the aperture 302 with a suture 2600. The aperture 302 in a patient's vessel 301 is closed with a cross-suture or equally a purse-string suture (not shown) that approximates the lateral sides of the aperture 302. The approximation of the lateral sides of the aperture 302 is causing narrowing of the vessel lumen as indicated by the arrows 2700.

Figure 29:
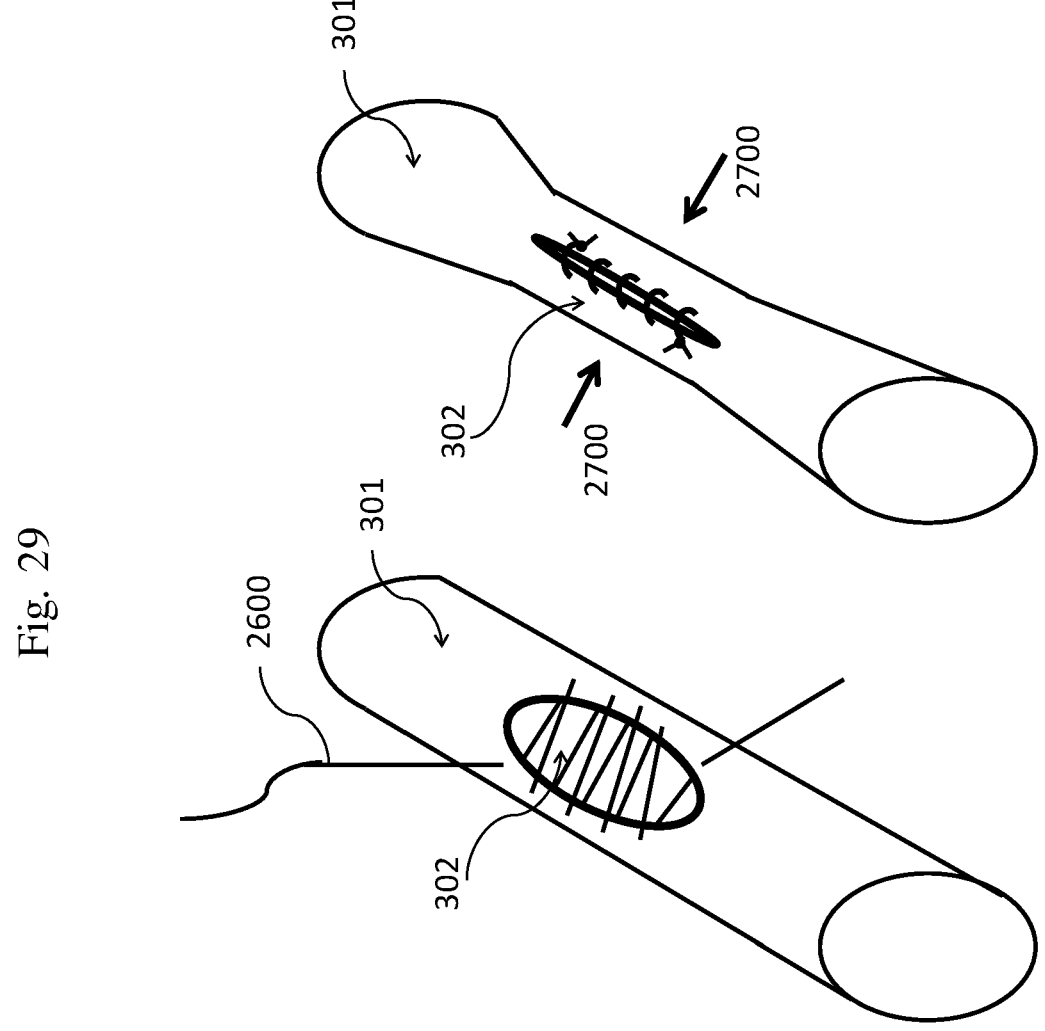
FIG. 29 shows the aperture in the patient's vessel and the closing with a longitudinal surgical procedure.

FIG. 29 is a surgeon view of the aperture 302 of a patient's vessel 301 showing the open surgical closure of the aperture 302 with a suture 2600. The aperture 302 in a patient's vessel 301 is closed with a longitudinal suture. The approximation of the lateral sides of the aperture 302, is causing narrowing of the vessel lumen, as indicated by the arrows 2700.

Only a transverse closure orthogonal to the vessel long axis like in FIG. 27, FIG. 10-FIG. 12 and FIG. 12-FIG. 26, will approximate the proximal and distal ends of the aperture 302 and at the same time spreading the transverse lateral ends of the aperture 302 avoiding narrowing of the vessel diameter and lumen.

Figures 30, 30A:
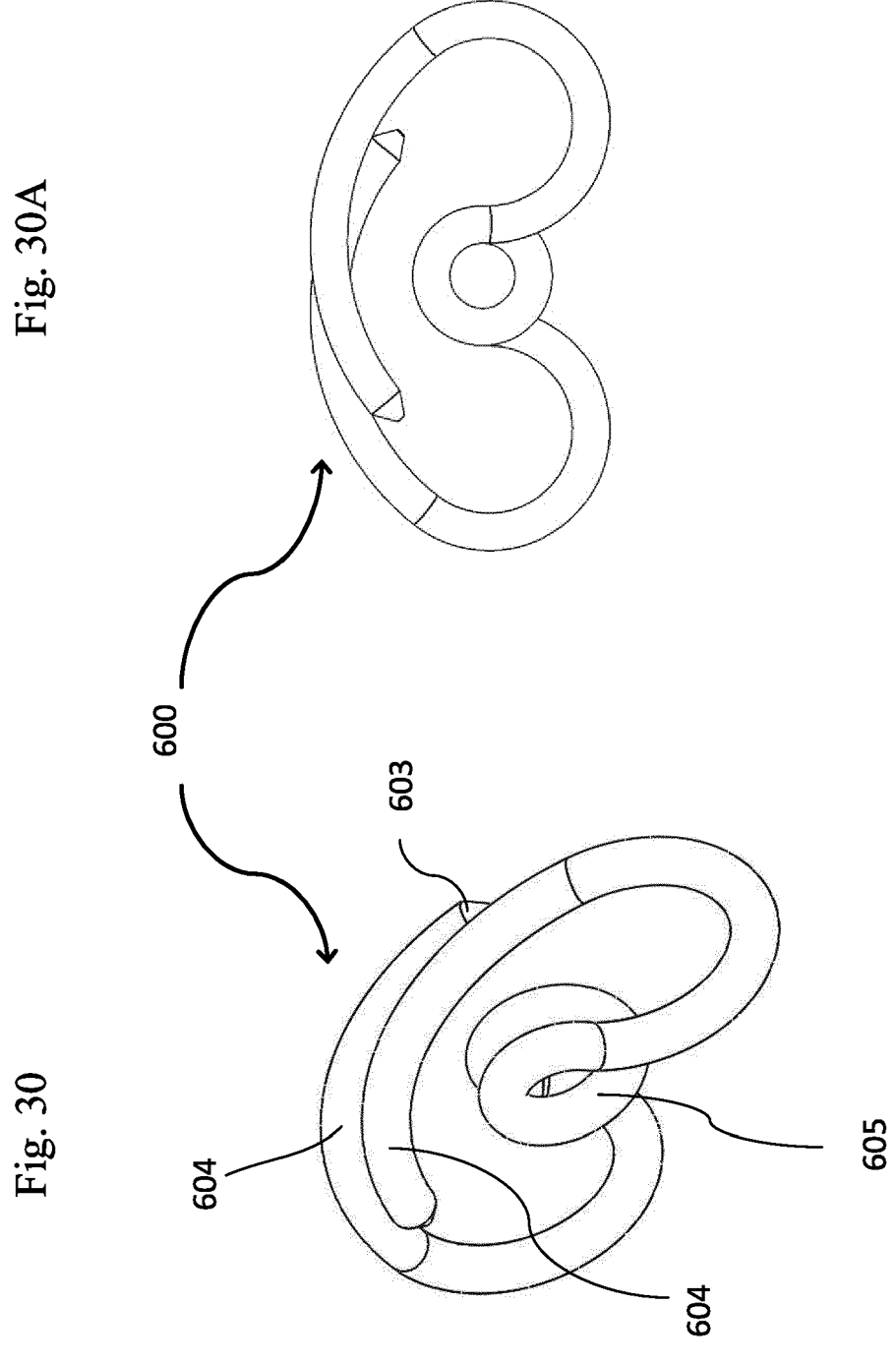
FIG. 30 shows a closing device in an embodiment in a perspective view.
FIG. 30A shows the closing device of FIG. 30 in a front view.

FIG. 30 shows a closing device 600 in an embodiment in a perspective view. It comprises two arms 604, each of which carries an optionally pointed end 603. The arms originate from a curled or curved section 605.

FIG. 30A shows the closing device 600 of FIG. 30 in a front view.

Figures 31, 31A:
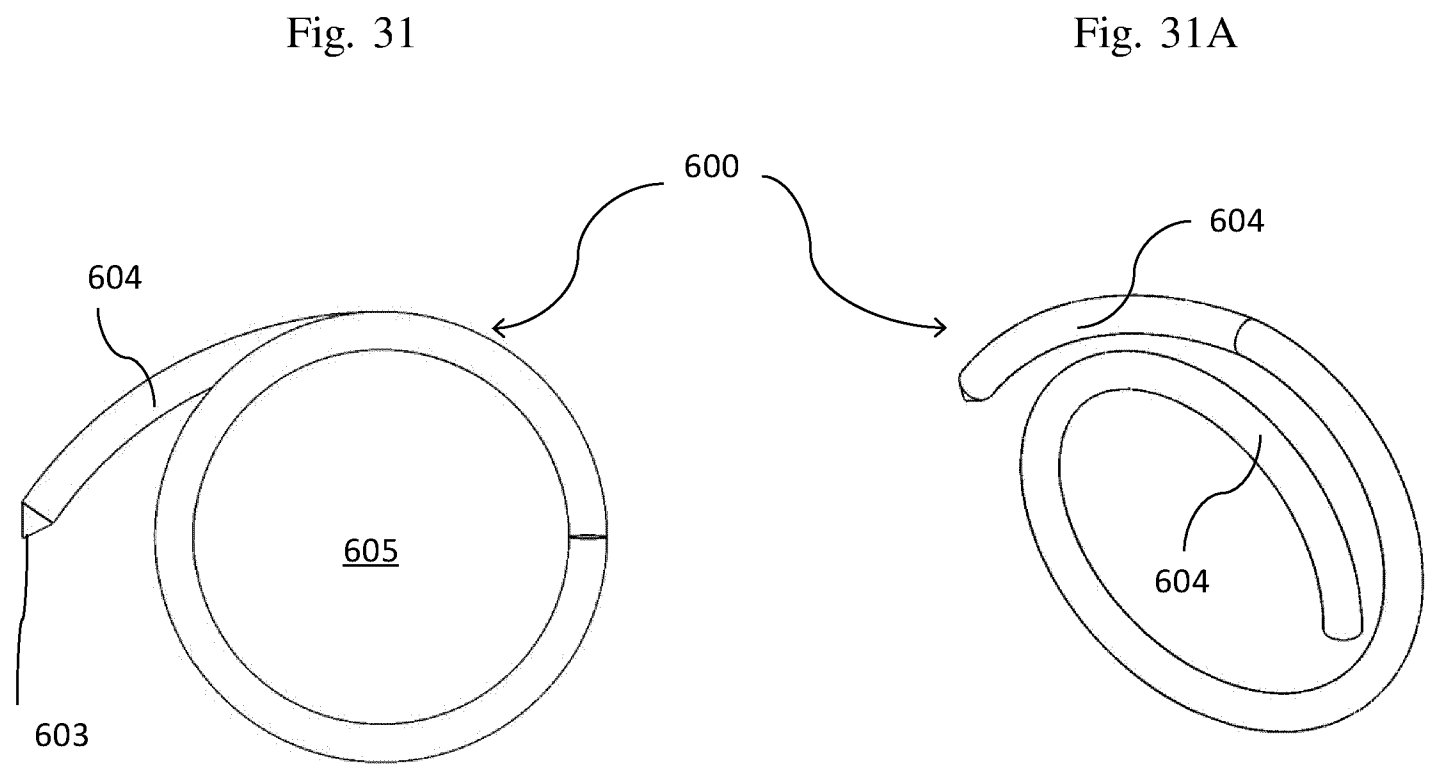

FIG. 31 shows a closing device 600 in yet an embodiment in a front view. It comprises two arms 604, each of which carries an optionally pointed end 603. No curled or curved section is provided.

FIG. 31A shows the closing device 600 of FIG. 31 in a perspective view.

Figures 32, 32A:
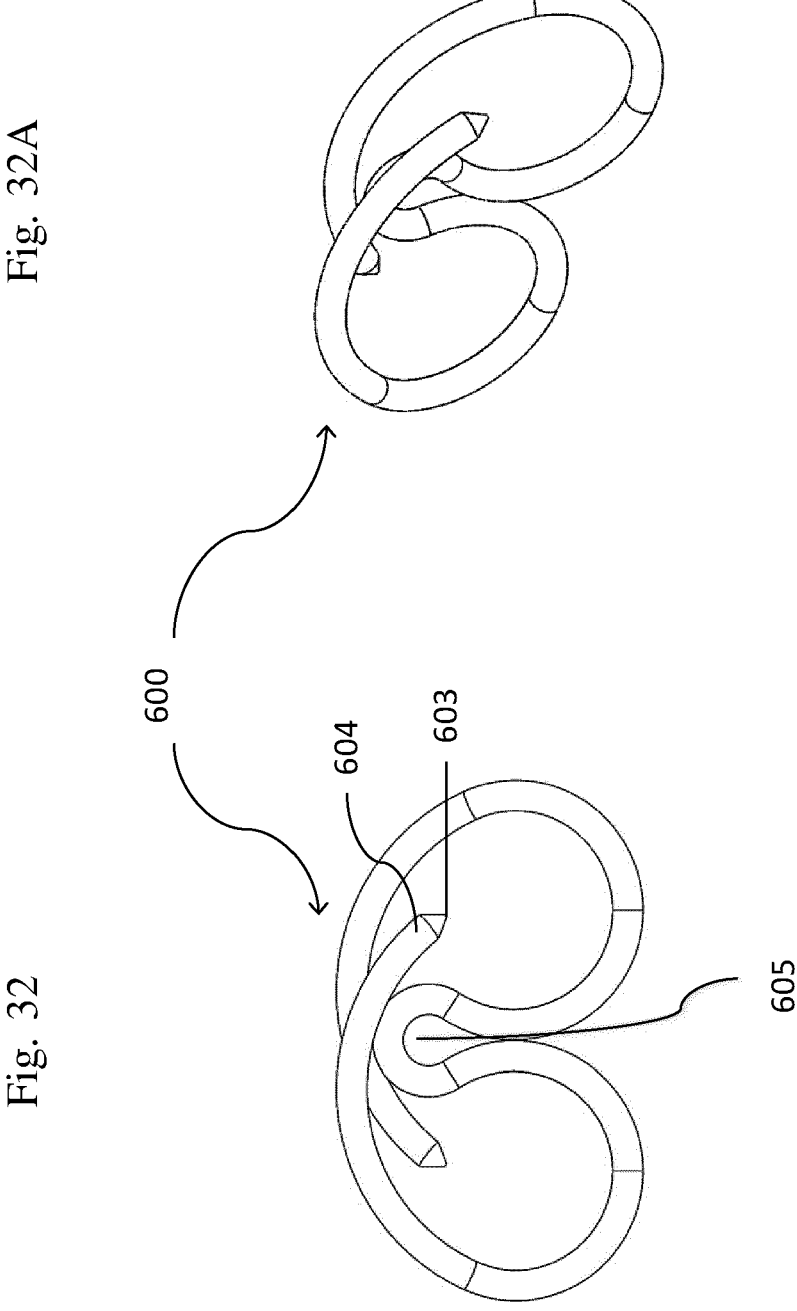
FIG. 32 shows a closing device in a further embodiment in a front view.
FIG. 32A shows the closing device of FIG. 32 in a perspective view.

FIG. 32 shows a closing device 600 in an embodiment in a front view. It comprises two arms 604, each of which carries an optionally pointed end 603. In contrast to the embodiment of FIG. 30, the curled or curved section 605 is not closed, meaning that there is no spiral section.

FIG. 32A shows the closing device 600 of FIG. 32 in a perspective view.

Figure 33:
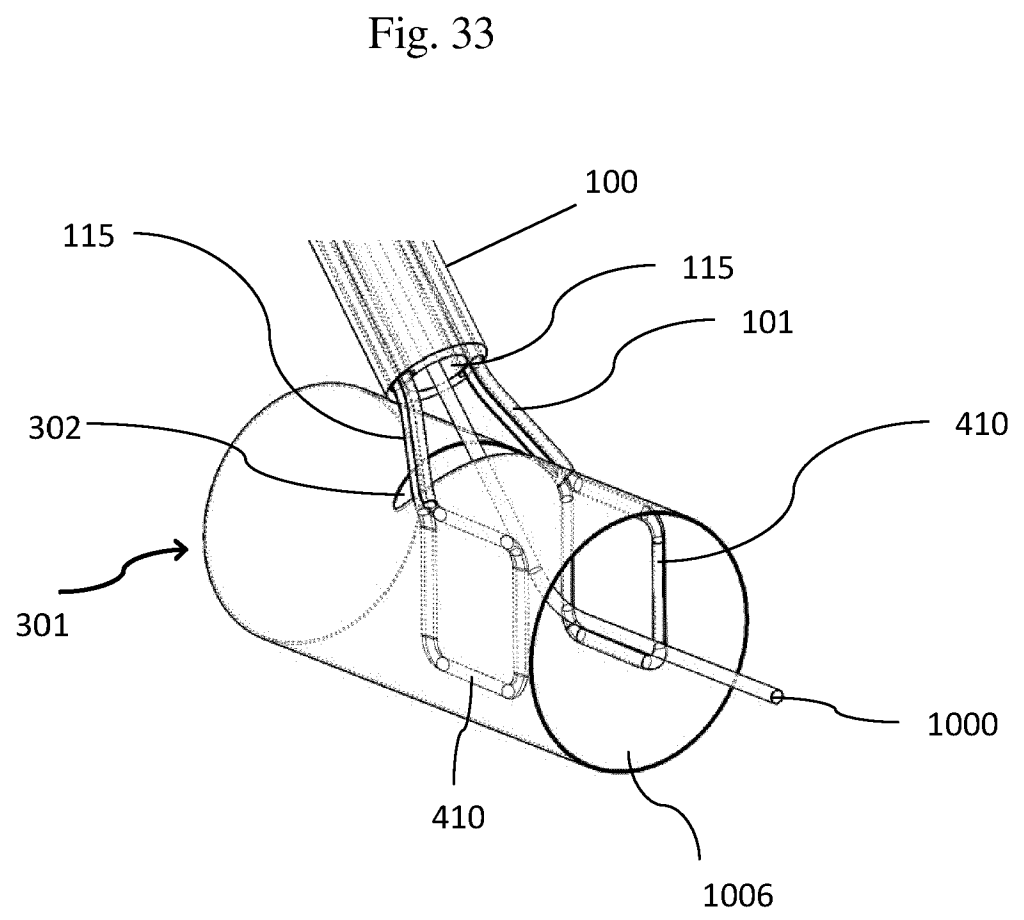

FIG. 33 shows parts of the medical apparatus according to the present invention in a perspective view. A guide wire 1000 is introduced into the lumen 1006 of the vessel 301. The guide wire 1000 is run through a central opening of the medical apparatus running denoted as guide wire lumen 115.

Two engaging devices 410 retract the aperture 302 into a slit.

Figure 35:
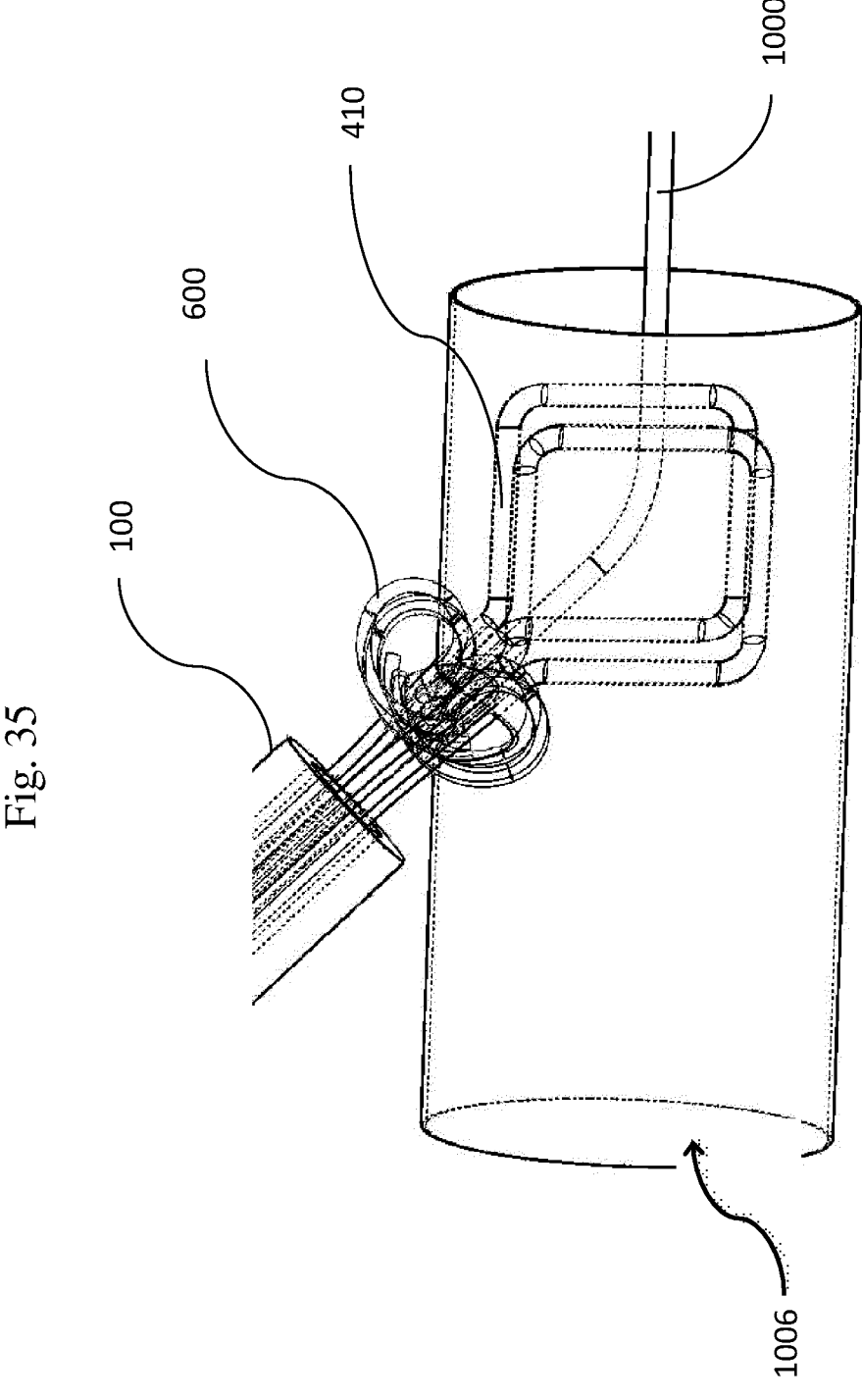
FIG. 35 shows parts of another embodiment of the medical apparatus from its side.

No retracting unit is shown in FIG. 33. If a retracting unit were shown, it could be arranged such that it can be advanced through the guide wire lumen 115, as is shown in FIG. 35 with respect to another embodiment of the medical apparatus.

Although not shown in the figures, the medical apparatus, and, in particular, the engaging device 410 or the retracting device 101 may comprise a section that hinders the guide wire 1000 to interfere with the closing device. The section may be a wire construct guiding the guide wire out of range of the closing device 600.

Figure 33A:
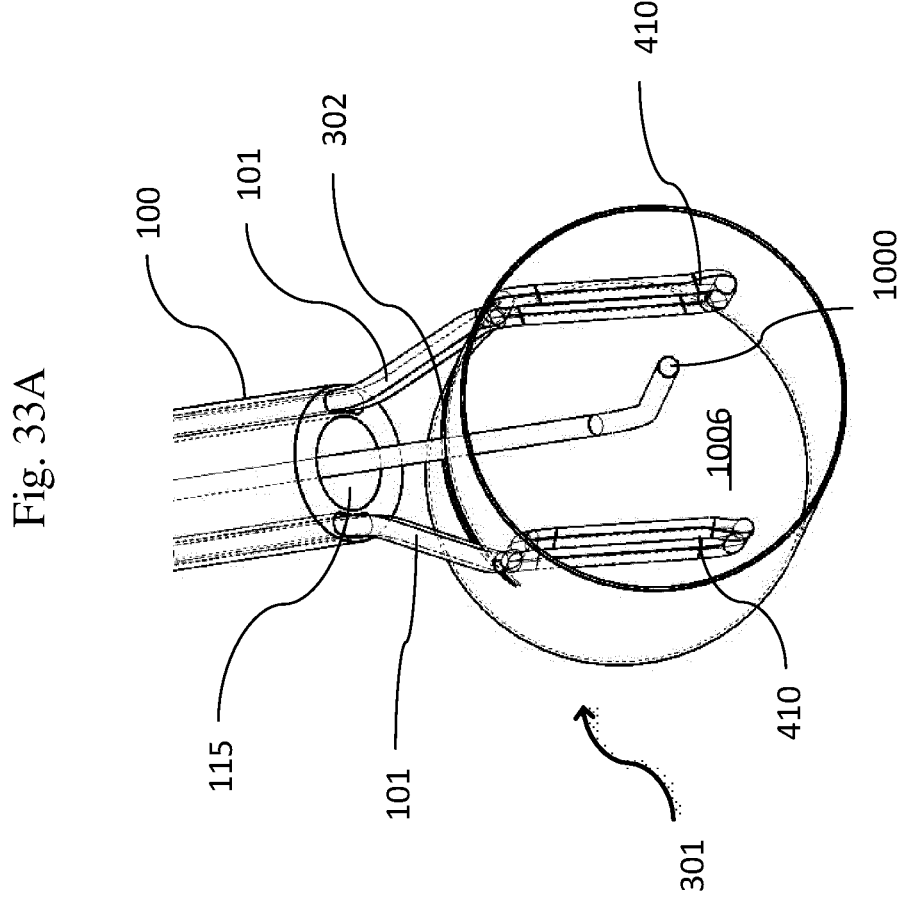
FIG. 33A shows the medical apparatus of FIG. 33 substantially from its front.

FIG. 33A shows the medical apparatus of FIG. 33 from its front.

Figure 34:
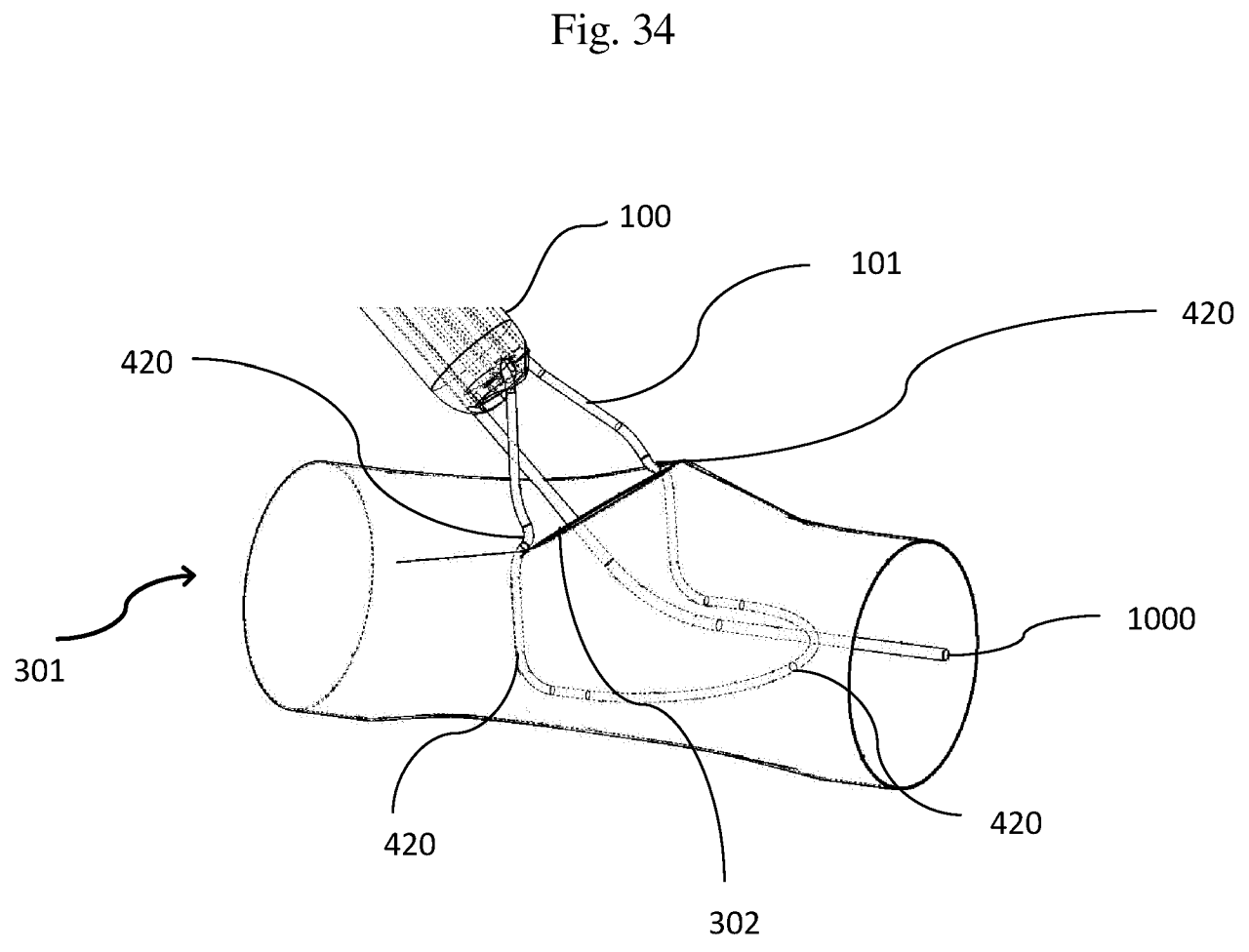

FIG. 34 shows in a perspective view parts of another embodiment of the medical apparatus. The engaging device 410 is built from a single wire. As can be seen from FIG. 34, the retracting device 101, or any other part of the medical apparatus that is inserted into the vessel lumen in use, may in any embodiment comprise a step or a curve 420 that may interact with the wall of the aperture 302 or the vessel 301 such that it gives tactile feedback to the surgeon upon pulling the medical apparatus again out of the vessel 301. If and when the surgeon feels the tactile feedback, he or she knows that the medical apparatus is ideally placed with respect to the aperture 302 in order to close it by releasing closing devices 600.

FIG. 35 shows parts of yet another embodiment of the medical apparatus from its side. FIG. 35 shows substantially what is also revealed in FIG. 33 or FIG. 33A. However, it also shows in a highly schematic manner two closing devices 600 closing the aperture 302. The engaging devices 410 have still to be folded again and withdrawn from the vessel lumen 1006.

Figure 36:
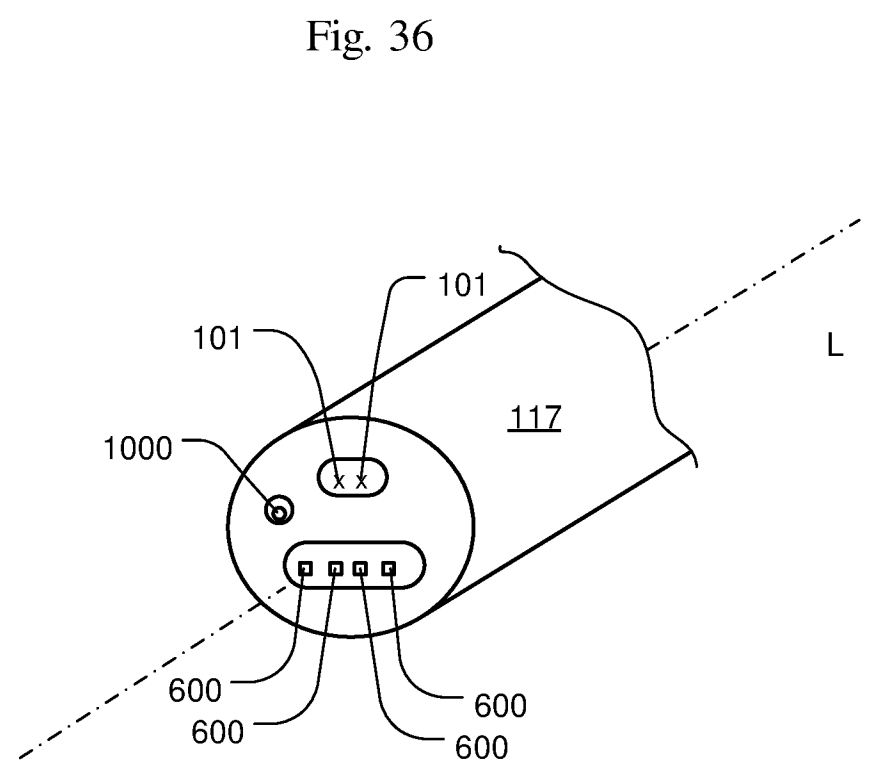

FIG. 36 shows a highly simplified view onto the front-end surface of the medical apparatus having a longitudinal axis L and a casing 117, in yet another embodiment. As can be seen, the end of the medical apparatus has several openings. One houses the guide wire 1000, one houses two retracting devices 101, one houses four closing devices 600.

It goes without saying that the number of openings, retracting devices 101 and closing devices 600 is not limit to the number shown in FIG. 36. Also, the guide wire 1000 may run through an opening used exclusively for the guide wire 1000. However, it could also share its opening with the retracting device or devices 101 and/or the closing devices 600.

FIG. 37A-F show two additional exemplary embodiments of closing devices 600 in different views.

Figures 37A, 37B, 37C, 37D, 37E, 37F:
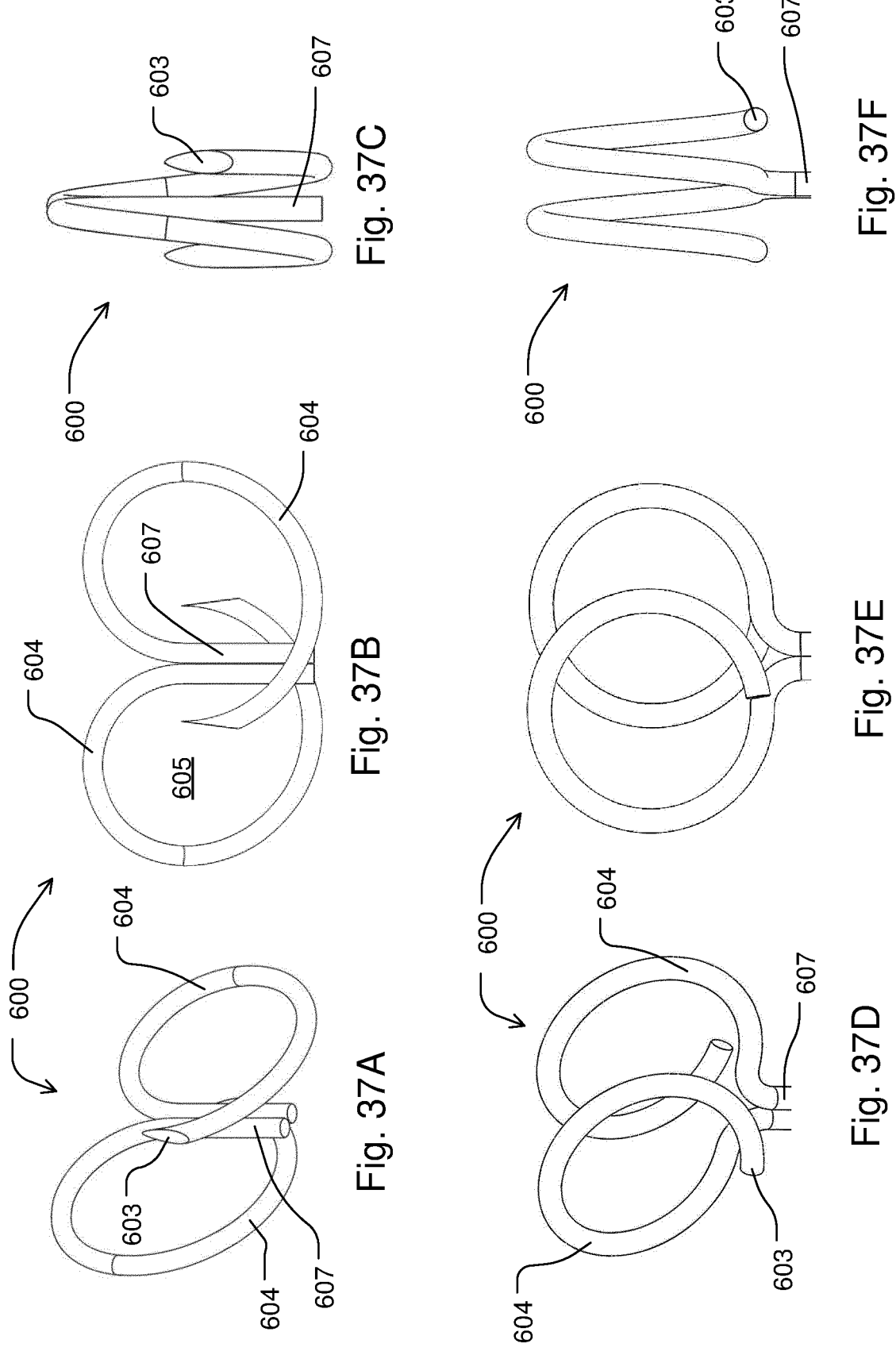
FIG. 37A-F show two additional exemplary embodiments of closing devices used in embodiments of the present invention in different views.

FIG. 37A-C show one of these additional embodiments in different views. FIG. 37A shows a perspective view, FIG. 37B a front view and FIG. 37C a side view. Two arms 604 of the wire-shaped closing device 600 are optionally fitted together in an optionally non-curved section 607. The fitting can be realized by soldering, gluing, friction welding or in another way. Alternatively, the two arms 607 are integral with each other, i. e., not joined to each other.

Also, the non-curved section 607 (non-curved in a fully employed state of the closing device 600) is part of some embodiments only and, hence, not binding.

The curved sections 605 are almost ring-shaped when eyed from the front (FIG. 37B) and show no turning point, in contrast to the curved sections 605 of the embodiment of FIG. 37D-F as will be discussed with more detail infra. Hence, the left arm 604 always turns, or is always bent, to the left (see FIG. 37B), the right arm 604 always turns or bends to the right.

The end profiles or sections of the arms 604 of the embodiment of FIG. 37A-C are optionally chamfered as pointed ends 603, so that they can easily penetrate the walls of the vessel.

The closing device 600 is preferably manufactured from a memory material like Nitinol. In this case, the ring-shape is autonomously assumed or taken by the closing device 600 once released or when it is located in the vessel, starting from an originally more or less straight shape the closing device 600 assumes or takes when it is positioned inside the closing device holder 802.

In FIGS. 37D-F yet another embodiment of a closing device 600 is shown in different views analog to the views of FIG. 37A-C.

In contrast to the embodiments of FIG. 37A-C a first section of each of the arms 604 that is close or next to the straight or non-curved section 607 of the arms 604 are bent away from the non-curved section 607 or from the other arm 604 in a first bending direction. The bending angle may be between 60° and 120°, preferably between 80° and 100°, most preferably 90° (degrees) in a first bending direction.

A second section following the first section may be bent by optionally almost 360 degrees. It may be bent into a second bending direction, the second direction being opposite to the first direction (first to the left, then to the right, or vice versa). The end profiles may be cut straight or almost straight as shown in FIG. 37D to 37F. Alternatively, they may be chamfered as in FIG. 37A-C. Again, the non-curved section 607 (non-curved in a fully employed state of the closing device 600) is part of some embodiments only.

It is noted that in the embodiment of FIG. 37D-37F both arms 604 may each have a first (or just one first) bending to the left and a second (or just one second) bending to the right.

Also, it is noted that in the embodiment of FIG. 37D-37F the end 603 of a first one of the arms 604 points away from the second one of the arms 604, whereas the end 603 of the second arm 604 points away from the first arm 604.

As can be seen from FIG. 37D-37F, the design of the closing device 600 of this embodiment allows the left arm 604 to capture tissue of the left side of the access site. It may pull that tissue towards the right arm 604. Similarly, the right arm 604 is arranged to capture tissue of the right side of the access site. It may pull that tissue towards the left arm 604.

This design has shown to provide a closer and, hence, more reliable closure of the vessel aperture 302. It appears that due to the tighter closure achieved one may advantageously achieve the set goal of closing the vessel aperture 302 by a smaller number of closing devices 600 and/or by using smaller closing devices 600.

The straight or non-curved section 607, which is optional, may serve for holding and/or pushing the closing device 600 until it is finally released. Also, the section 607 may be used for interconnecting the two arms 604 with each other, e. g., in a welding process.

If manufactured from a shape memory material, the arms 604 may start pulling the tissue of the opposing sides of the vessel aperture 302 once unsheathed.

Figure 38:
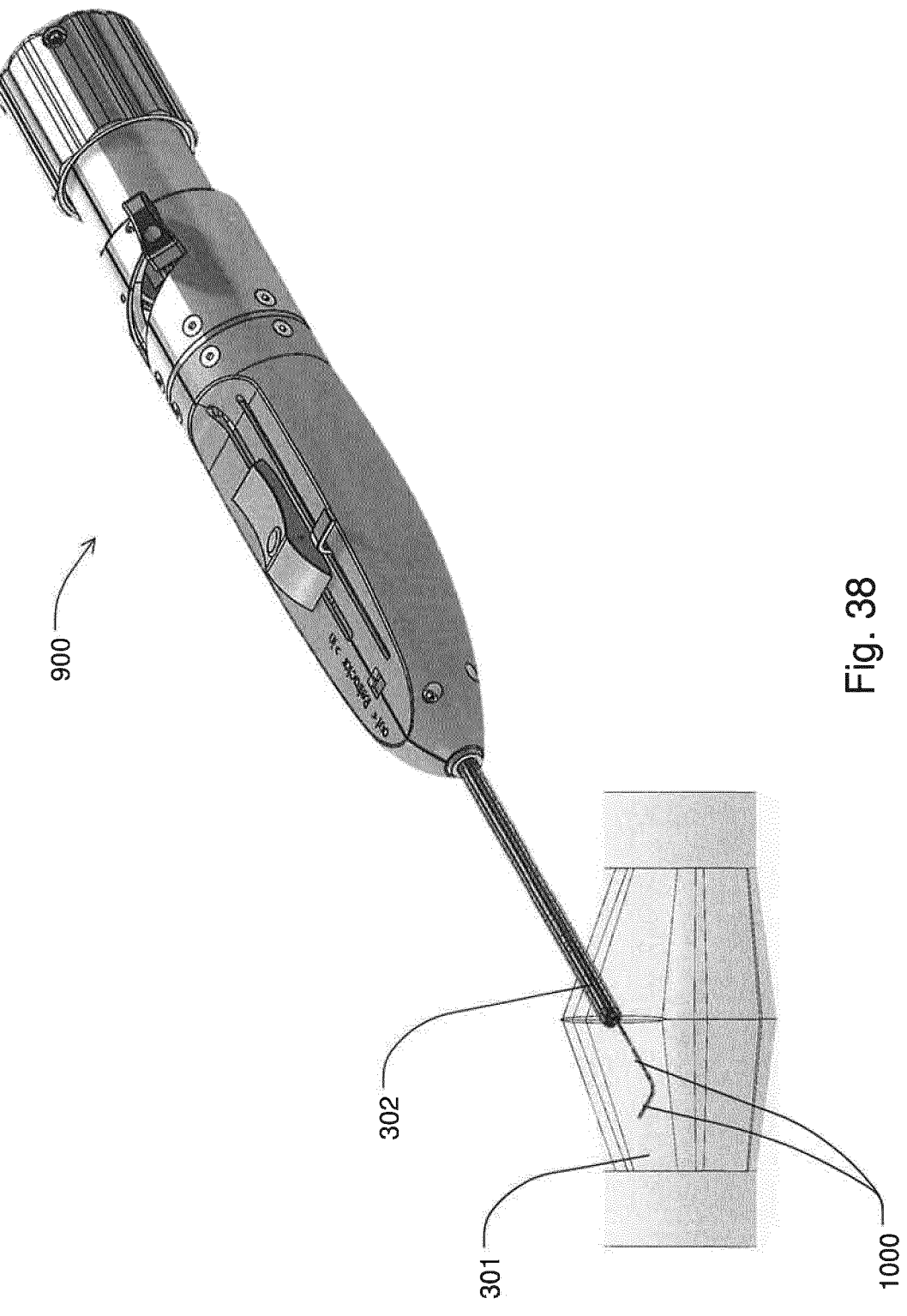
FIG. 38 shows a handle member that is part of embodiments of the medical apparatus according to the present invention with a guide wire advanced into a blood vessel.

FIG. 38 shows a handle member 900 of the medical apparatus and a guide wire 1000 advanced into a blood vessel 301 (e. g., a vein) through an aperture 302 of the blood vessel 301. The design and use of the handle member 900 and at least some of its mechanisms for pushing and advancing components such as the guide wire 1000, the retracting device 101 and more are described below.

Figure 39:
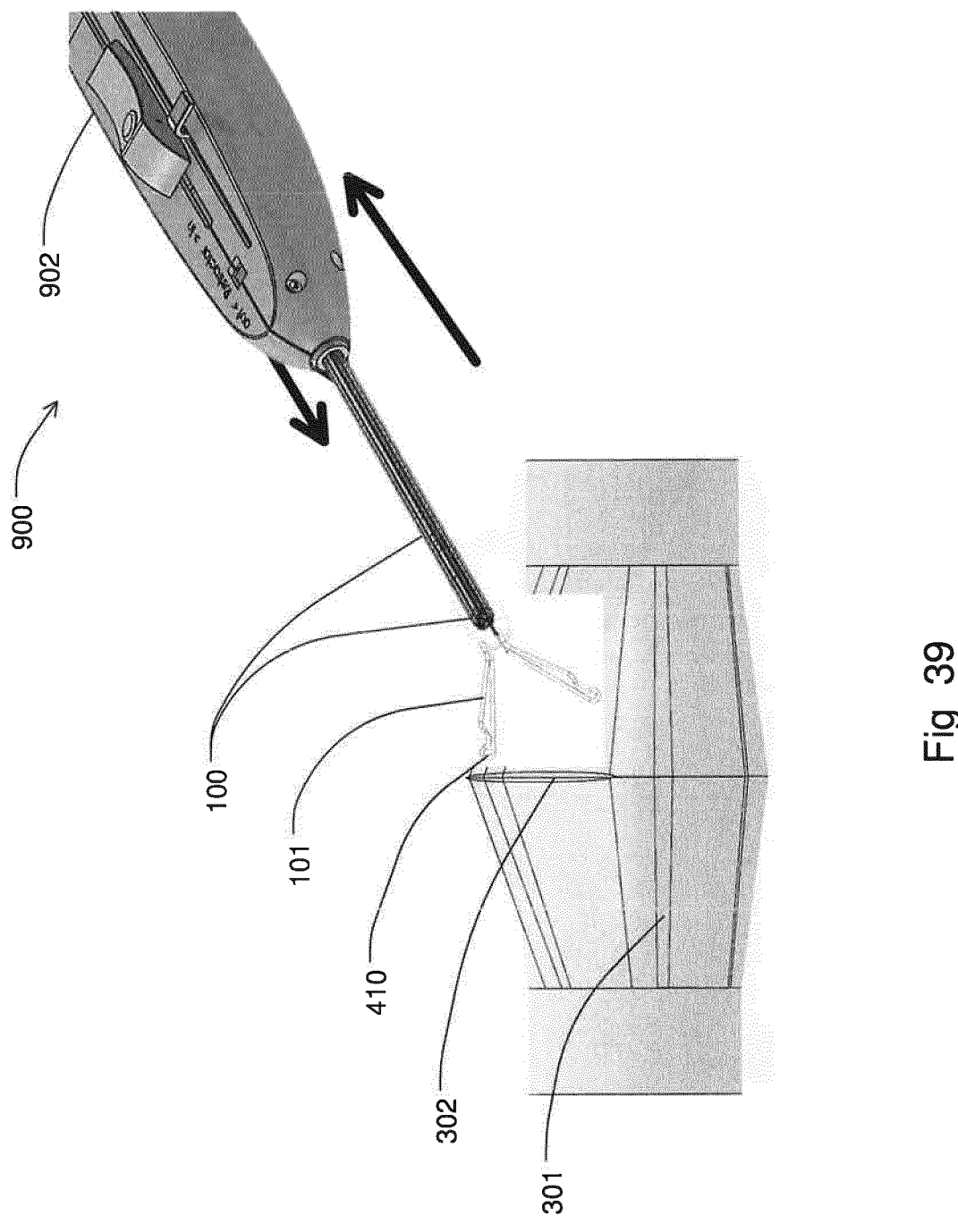
FIG. 39 shows an embodiment of the retracting device which is activated by the handle member.

FIG. 39 shows an embodiment of the retracting device 101 and engaging device 410 which is activated by the handle member 900.

In this embodiment, in order to activate or advance the retracting device 101, in a first step an optional first slider 902 is pushed by the user in the direction marked by the corresponding arrow (towards the vessel 301).

Likewise, together with this first slider 902 an optional second slider 904 is also moved by the user as also denoted by another corresponding arrow (again towards the vessel 301). The function of the second slider 904 is explained below.

In its end position or in another position, the first slider 902 may optionally be locked in place. At the end of this first step the retracting device 101 is not yet expanded within the vessel 301, and it is not yet engaged with the access site. However, the tips of the retracting device 101 have parted from each other.

In a second step, the handle member 900 is pulled back by the user as indicated by the arrow shown next to the handle member 900 and pointing away from the vessel 301 until the user can feel that the retracting device 101 is completely engaged with its engaging device 410 at the access site. At this state, the opposing edges of the slit opening 302 lie close together due to the arms of the retracting device 101.

Figure 45:
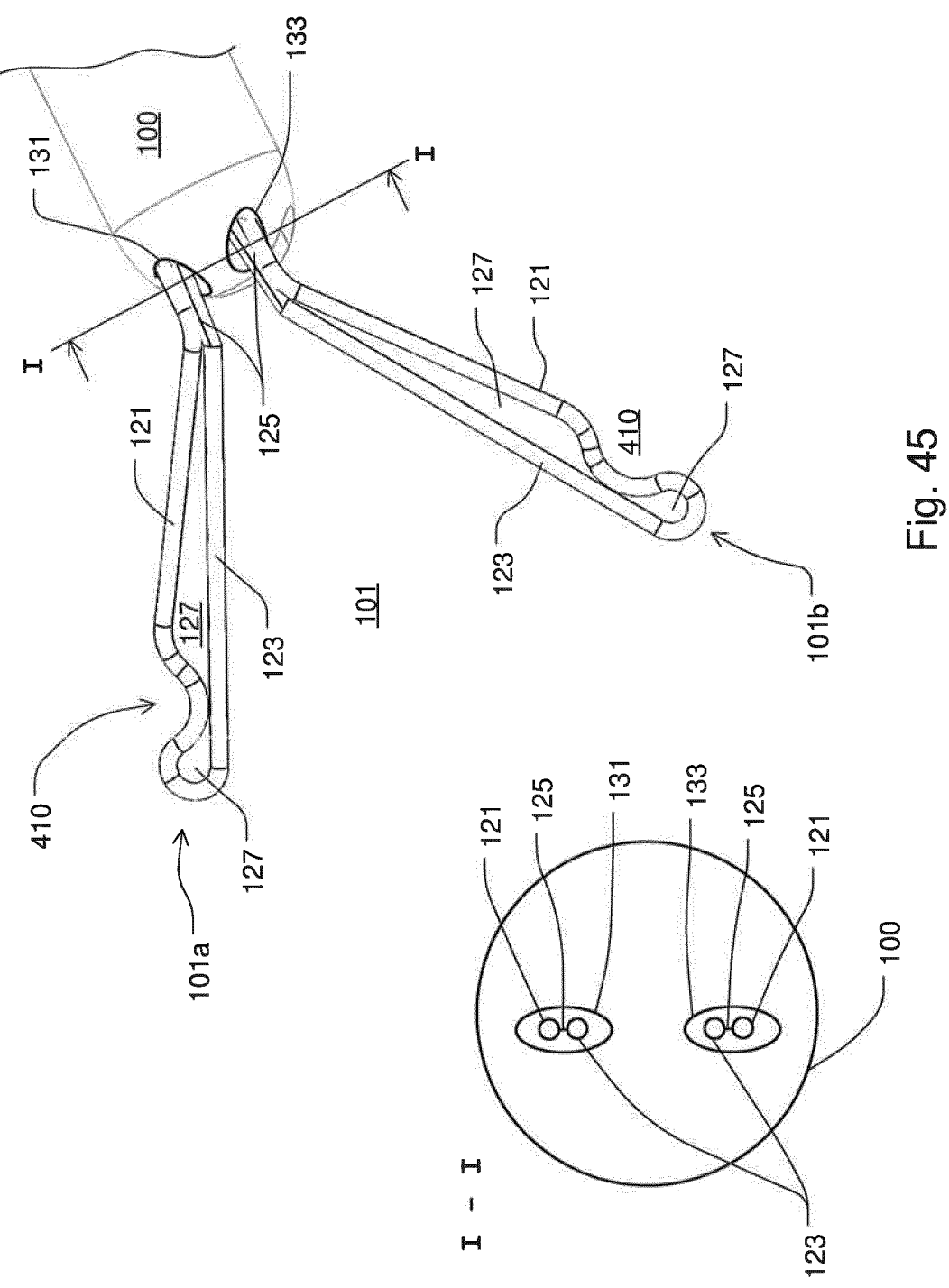
FIG. 45 shows the design of the retracting device and the engaging device in an exemplary embodiment.

The optional design of the retracting device 101 and the engaging device 410 shown in this figure is further discussed with respect to FIG. 45.

Figures 40, 40A, 40B, 40C:
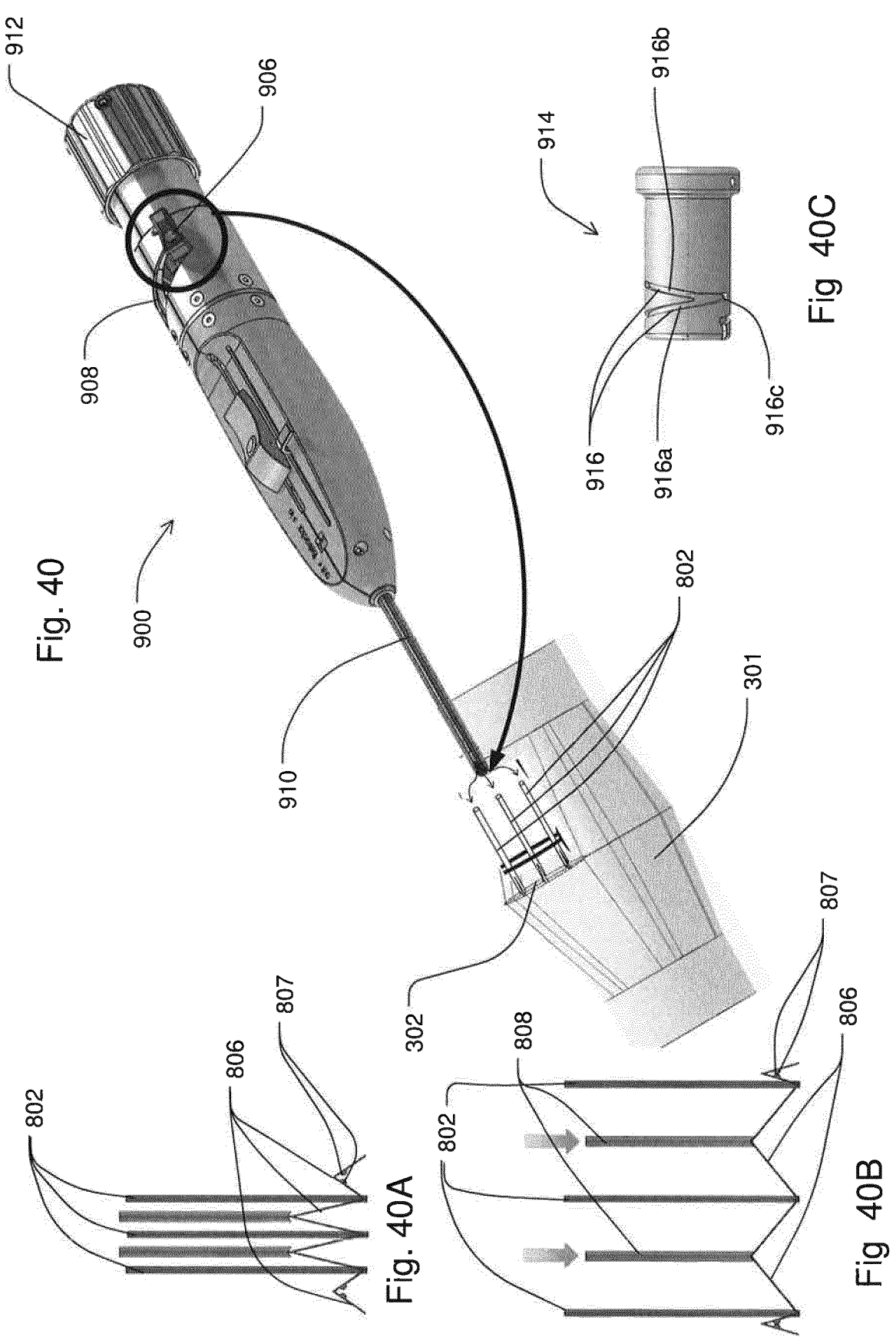
FIG. 40 shows three, optionally parallel, closing device holders pushed to the aperture by the handle member.
FIG. 40A shows a delivery support for the three parallel closing device holders of FIG. 40.
FIG. 40B shows the delivery support of FIG. 40A in an expanded state.
FIG. 40C shows a sleeve with a guide slot as an insert or part of the handle member.

FIG. 40 shows (optionally three) closing device holders 802 pushed towards the aperture 302 by a mechanism comprised by the handle member 900. The closing device holders 802 may be parallel to each other, fully or only in parts thereof.

Pushing the closing device holders 802 out of the closing member 800 and/or the handle member 900 may be activated by an optional switch 906 or another feature of the handle member 900. The switch 906 is arranged to be movable within an opening 908 of the casing of the handle member 900.

In this first step, the switch 906 is optionally pushed to a first stop that can be provided by the left end of the opening 908 (see the position the switch 906 has taken in FIG. 40).

In this first step, by operating the switch 906, the closing device holders 802 are spread to full width which means that they are located—optionally more or less equidistantly—along the aperture 302. In FIG. 40 this is indicated by the three small arrows between the closing device holders 802 and the single lumen or multilumen extrusion or opening 910. The closing devices 600 are still inside the closing device holders 802.

It is noted that the closing device holders 802 can remain parallel throughout the closure of the vessel aperture 302, or they can be arranged to deviate from each other. For example, they may be arranged such that neighboring closing device holders 802 may move away from each other, at least in part, when they are deployed. For example, they may be arranged such that the gaps, spaces or distances between their tips become wider when advanced towards the vessel aperture 302.

FIG. 40A shows an optional delivery support 806 for the three or more parallel closing device holders 802. In the not yet expanded state of FIG. 40A, which can be the state assumed by the closing device holders 802 at the end of the first step as described with respect to FIG. 40, the closing device holders 802 are separated by small distances from each other. Their separation may be triggered by the design of the delivery support 806. The delivery support 806 may comprise a wire net or structure or consist thereof. The delivery support 806 may be a foldable and/or unfoldable element.

Optionally, at the outer or lateral sides of the closing member, of the closing device holders 802 or of the delivery support 806 bumpers 807 may optionally be comprised. These bumpers 807 are spacers as shown in FIG. 40B in an expanded or unfolded state of the delivery support 806.

FIG. 40B shows the delivery support 806 of FIG. 40A in an expanded or unfolded state. The delivery support 806 has been unfolded by pushing it downwards as indicated by the arrows at the top of the pusher tubes 808. The activation spreads the closing device holders 802 and distributes them along the slit opening 302. In order to keep a small distance between the lateral closing device holders 802 and the outer edges of the slit opening 302, the bumpers 807 may act as spacers and maintain this small distance during closure of the vessel aperture 302.

FIG. 40C shows a sleeve 914 with a—optionally U- or V-shaped—guide slot 916 (guidance groove). The sleeve 914 is part of the handle member 900. In the guide slot 916 a pin or another protrusion of the knob 912 that is preferably arranged at the rear of the handle member 900 (see FIG. 41), or another element connected to the knob 912 can be moved, e.g., as it is known from so-called tongue-and-groove systems.

The guide slot 916 comprises a first slot section 916a and a second slot section 916b each being connected with each other by another section, called a turning point 916c. In this turning point 916c a pin, when being moved along the guide slot 916 from the first slot section 916a thereof to the second slot section 916b thereof, or vice versa, is first moved in the clockwise direction along the guide slot 916 and around the longitudinal axis of the sleeve 914 and, once having reached the turning point 916c, anti-clockwise, or vice versa. It is noted that the pin can be part of the knob 912 while the guide slot 916 is part of the sleeve 914, or vice versa.

Hence, when turning the knob 912 in a first direction (clockwise, for example), the pin will move along the first slot section 916a and eventually enter the turning point 916c of the guide slot 916 where the knob 912 will stop turning. The turning point 916c can, hence, be understood as a stop.

For further advancing the sleeve 914 relative to the knob 912 (or vice versa), the knob 912 has to be turned in the second direction (anti-clockwise, for example). An elastic element, a spring or the like can make sure that the pin will enter smoothly into the second slot section 916b once it has reached the turning point 916c and is about to leave the latter.

Providing a guide slot 916 as discussed supra may allow the user (surgeon) to have tactile feedback indicating that a predetermined feed of the sleeve or the pin has been achieved, in particular if the guide slot 916 is U- or V-shaped. Further feed can only be achieved by reversing the direction in which the knob is turned. This feature is, hence, a safety measure. Also, it may enhance precision upon advancing elements such as the closing devices 600.

Figure 41:
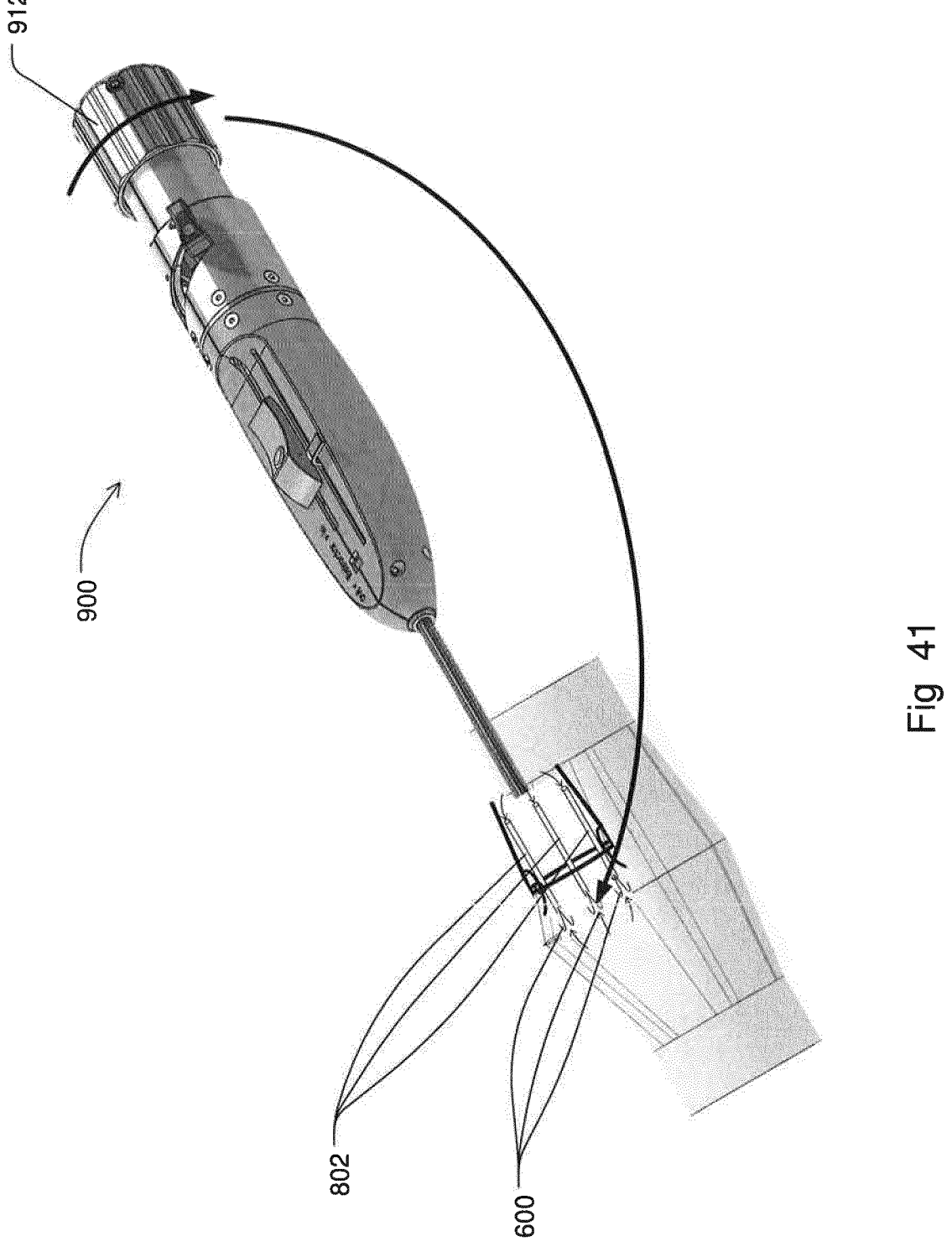
FIG. 41 shows three closing devices comprised in the closing device holders and pushed forward by a mechanism of the handle member.

FIG. 41 shows three closing devices 600 pushed forward within the closing device holder 802 by a mechanism of the handle member 900. In this particular embodiment, this mechanism is activated or operated by turning the knob 912 at the rear end of the handle member 900 in order to advance and to at least partly release the closing devices 600 for closing the aperture 302. It is referred to in the above discussion of the optional V-shaped guiding slot 912.

Figure 42:
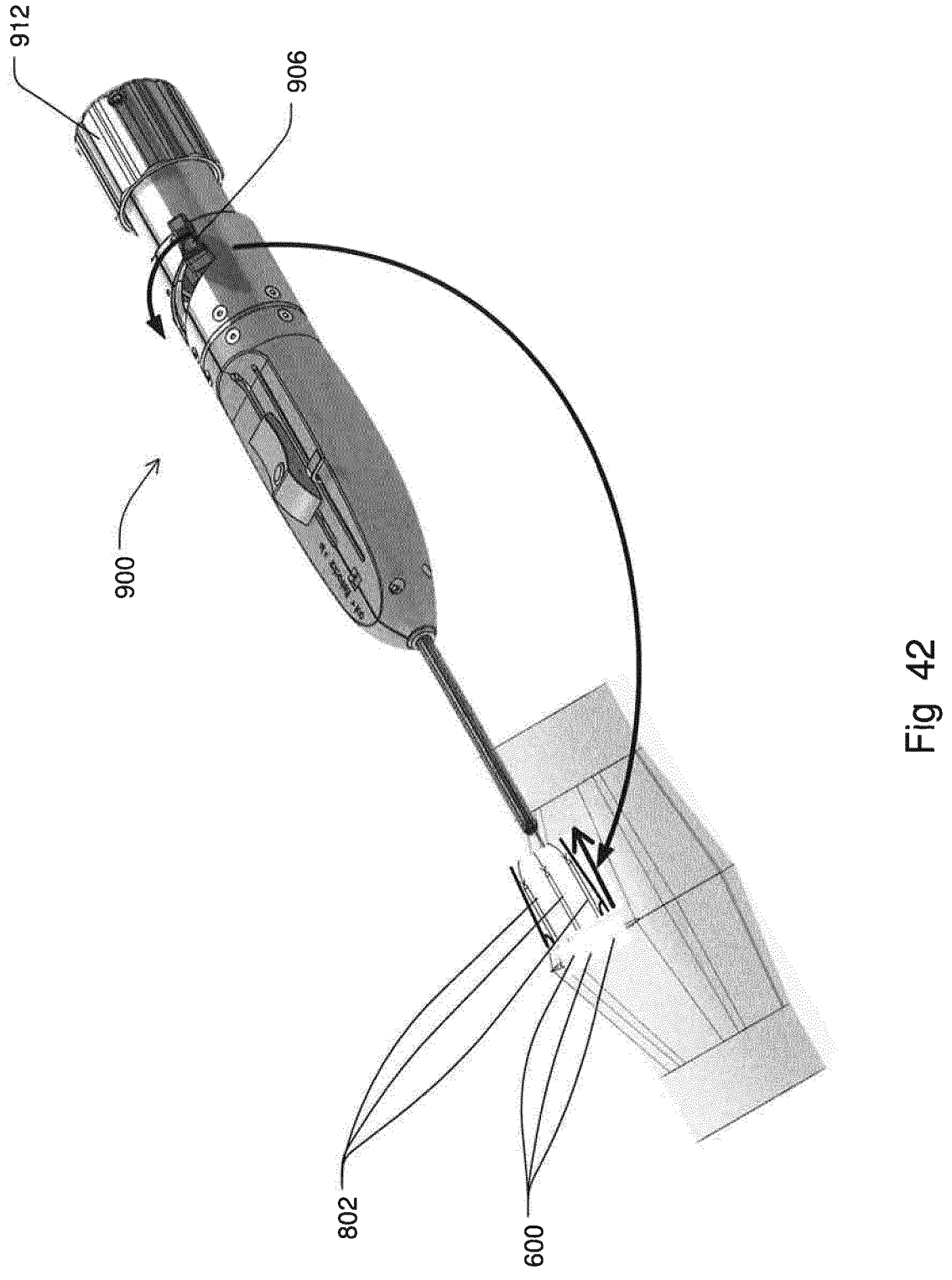
FIG. 42 shows the three closing device holders of FIG. 41 being pulled back by a mechanism of the handle member.

FIG. 42 shows how the three closing device holders 802 are pulled back by a mechanism of the handle member 900.

In particular, turning the switch 906 in the opposite direction than discussed with respect to FIG. 40 (thus, to the right in FIG. 42) will pull the closing device holders 802 backwards as indicated by the arrowing directing to the rear end of the handle member 900.

By the end of this step, the closing devices 600 have closed the aperture 302 by piercing the edges of the aperture 302 upon taking on their final shape. The final shape of the closing devices 600 can be predetermined upon manufacture of the closing devices 600, e. g., by using a shape memory material like Nitinol.

Figure 43:
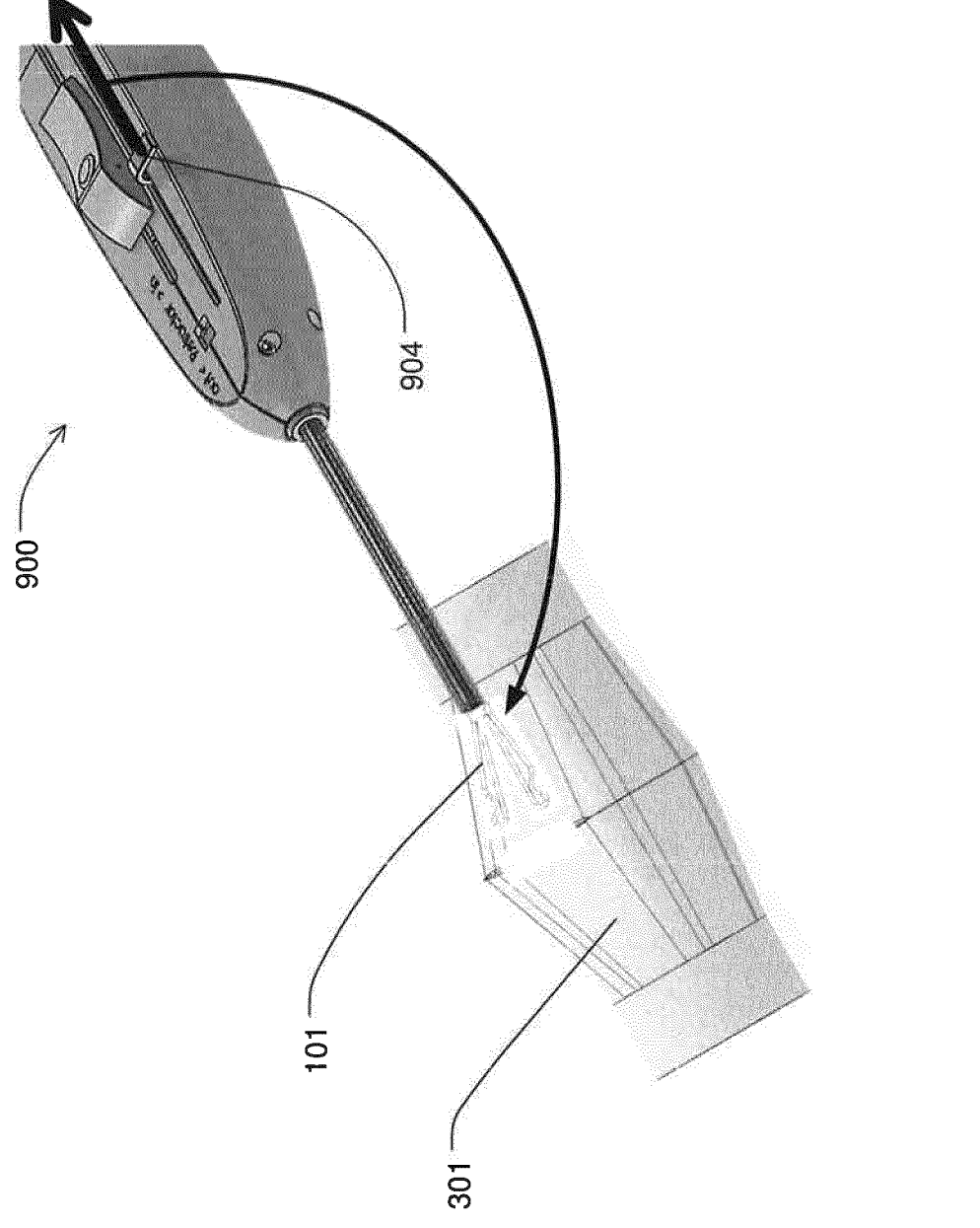
FIG. 43 shows the release of the retracting device from the access site by a mechanism of the handle member.

FIG. 43 shows the release of the retracting device 101 from the tissue of the aperture 302 due to a mechanism of the handle member 900. This mechanism is optionally activated or triggered by pulling back the second slider 904. This step makes it possible to decouple the two parts of the retracting device 101 in order to pull them back and out of the vessel 301.

Figure 44:
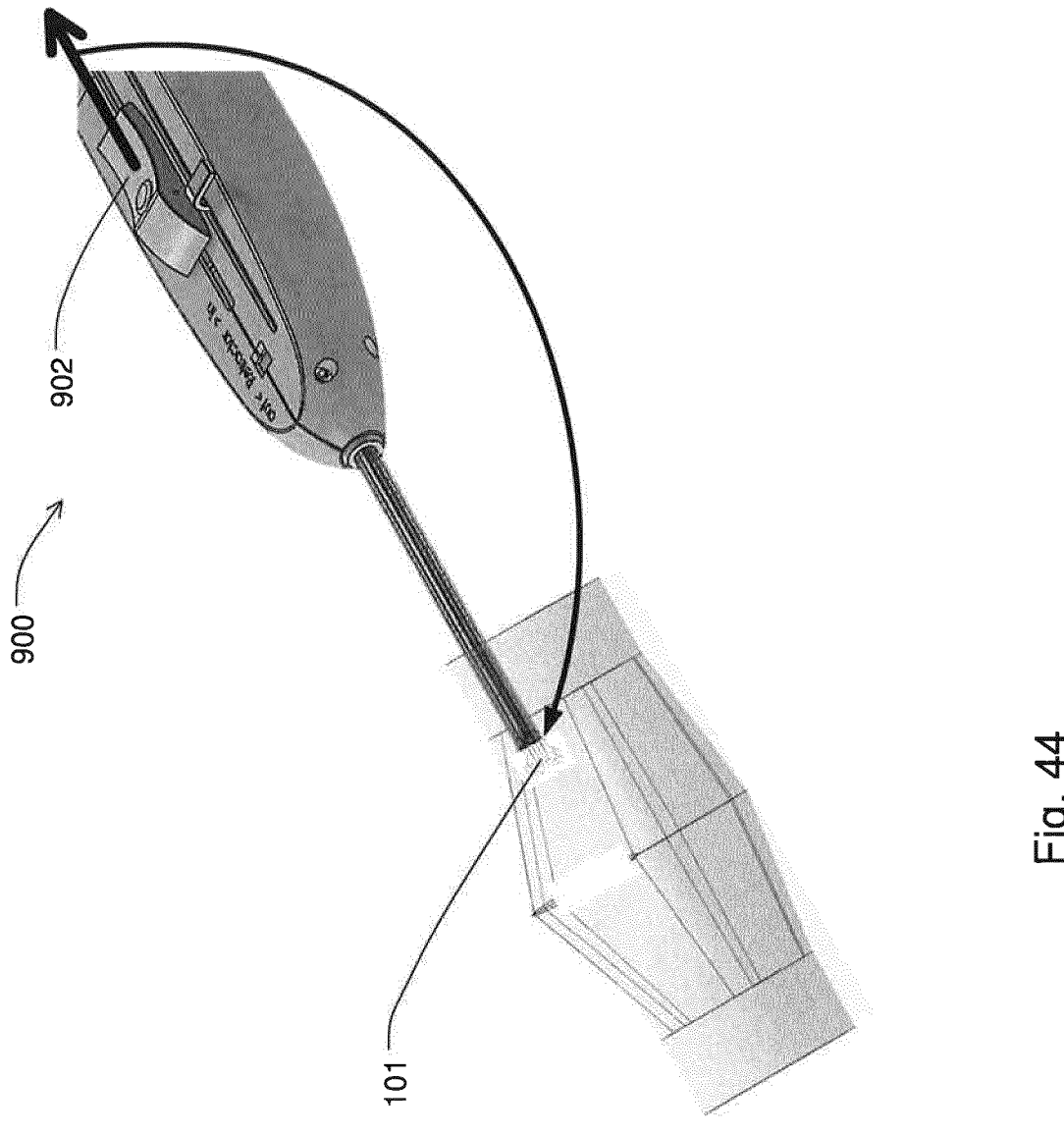
FIG. 44 shows a mechanism of the handle member for full remove or removal of the retracting device and the medical apparatus from the access site.

FIG. 44 shows a mechanism of the handle member 900 for fully removing the retracting device 101. In this final step, the first slider 902 is pulled back to the rear side of the handle member 900. Following this step, the complete handle member 900 system can be removed.

FIG. 45 shows the optional design of the retracting device 101 and the engaging device 410 shown in, e. g., FIG. 39, in an enlarged illustration. Also, a cut along I-I is shown in FIG. 45.

In the exemplary embodiment of FIG. 45, the retracting device 101 of the retracting unit 100 comprises a multitude (here: two) of arms, here arm 101a and arm 101b.

Arm 101a of the engaging device 101 comprises two legs 121 and 123. Leg 121 is called the outer leg, leg 123 is called the inner leg, as in the retracting position of the retracing device 101 leg 121 is more lateral than the more medial leg 123 (see FIG. 45).

Legs 121 and 123 may be welded to each other in or by a welding section 125.

Distal to the welding section 125 the legs 121, 123 may part from each other so that they surround or circumscribe one or two middle openings 127 which may be trough-openings.

The inner leg 121 may be straight or substantially straight. The outer leg 123, however, may be bent such that to its outer side (lateral, see FIG. 45) an indentation, a bulge or a dent is provided.

The indentation, bulge or dent forms the engaging device 410 already described supra. It may be used for releasably engaging with the tissue. For example, the engaging device 410 may provide a tactile feedback to the surgeon upon withdrawing the medical apparatus slightly from the vessel aperture 302 in order to position it appropriately with regard to the vessel 301 or its aperture 302.

Due to the particular shape of the engaging device 410, the arm 101a has the shape of a splint.

What has been said for arm 101a can hold true for arm 101b as well.

As can be seen from FIG. 45, the arms 101a and 101b exit through separate openings 131 and 133, respectively, from the retracting unit 100, although the arms 101a and 101b could exit through a common opening as well.

As can be seen from the cut along line I-I also shown in FIG. 45, at least one of the openings 131 is designed to have a width that is smaller than the length of a cross section of the arms 101a and 101b (e. g., in a cross section through the welding section 125). To this end, the particular shape of the opening 131 or its opening area, or of a void inside the retracting unit 100 following the opening 131 and ending at the opening 131 is longer (in an up-down direction in FIG. 45) than broad (in a left-right direction in FIG. 45).

Such a shape can, for example, be achieved by choosing an oval shape for the opening 131 (or such a cross section of the void behind it comprising the retracting device 101 or parts thereof before they are released during use), e. g. like the one shown in FIG. 45.

Such a shape may prevent an undesired twisting or turning (along its longitudinal axis) of the arms 101a, 101b during use and in particular when pulling back the entire medical apparatus for bringing it into the desired position for releasing the closing devices 600. Preventing the arms 101a, 101b from twisting or turning may contribute to maximally retracting the vessel aperture 302.

Of course, any other solution that may avoid twisting may additionally, or alternatively, be provided. For example, a pin, a protrusion or the like arranged to prevent twisting or turning may be arranged.

Figures 46C, 46D, 46E:
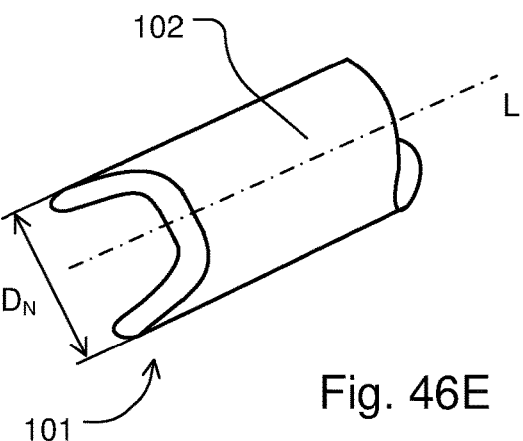

FIG. 46 is a schematic view of an additional exemplary embodiment of the retracting unit 100. In the sequence from FIG. 46A to FIG. 46C different steps and views for positioning the retracting device 101 at the aperture 302 are shown and will be explained in detail below. FIG. 46D shows an alternative design for a deploying device 103. FIG. 46A is an embodiment of the retracting unit 100, comprising the retracting device holder 102 with the retracting device 101, the deploying device 103 being configured for sliding within the retracting device holder 102 towards or up to the aperture 302.

The retracting unit 100 can be inserted from outside 303 of a patient's body through the patient's skin 304 up to the aperture 302 of the vessel 301 inside 305 of the patient's body. As shown in FIGS. 46A and 46B the proximal end section of the retracting device holder 102 is optionally located outside 303. After positioning the retracting unit 100 with the retracting device 101 at the aperture 302 as shown in FIG. 46B, the proximal end section of the retracting device holder 102 can be captured and fixed manually, so that the deploying device 103 can be pulled back as indicated by the arrow.

The deploying device 103 is releasably positioned inside the retracting device holder 102 in this embodiment. The longitudinal axis L of the retracting device holder 102 and the longitudinal axis L of the deploying device 103 are coaxial, preferably, as in FIG. 46A, identical. At least one cross-sectional shape of the retracting device holder 102 and of the deploying device 103 is preferably circular or almost circular. However, as can be seen in FIG. 46A, some sections, e. g., a distal end section of the retracting device holder 102, may be different, as shown in more detail in FIG. 46B, revealing that the retracting device 101 comprises a first arm 135 and a second arm 137 forming the distal end section of the retracting device holder 102. The distal end 112 of these arms 135, 137 are optionally spherical shaped. A cross sections of at least one of the arms 135, 137 may optionally be circular or round.

The configuration shown in FIG. 46A of the retracting unit 100 is preferably used for moving the retracting device holder 102 with its distal end section 101 close to or into the aperture 302. The outer diameter $D_R$ of the retracting unit 100 corresponds with the outer diameter of the retracting device holder 102 and/or with the width of the retracting device 101, at least in sections thereof.

The distal end section and/or another section of the deploying device 103 is preferably conically shaped. Also, it may be configured to protrude out of the retracting device 101 or the retracting device holder 102 at a front end thereof as is shown in FIG. 46A. This shape of its tip may facilitate pushing the retracting unit 100 forward through the tissue of the patient. Also, in this way the tip may serve as a pathfinder.

The first arm 135 and the second arm 137 of the retracting device 101 optionally fit closely to the outer surface of the retracting device holder 102 as shown in FIG. 46A.

The arrow in FIG. 46B indicates a step following the positioning of the distal end section of the retracting device 101 close to the aperture 302. If positioned correctly, the distal ends 112 of the two arms 135, 137 should have been positioned inside the aperture 302 so that the arms 135, 137 will retract or spread the aperture 302 upon pulling back the deploying device 103, as indicated in FIG. 46B the result of which step is shown in FIG. 46C. As stated supra, the step of pulling back the deploying device holder 103 is indicated by the arrow parallel to it.

After having completely pulled out the deploying device 103 from the retracting device 101 and possibly also from the lumen of the retracting device holder 101, resulting in having separate elements 102, 103 as shown in FIG. 46C, the cross-section of the retracting device holder 102 may change from its first shape, e. g., circular to a second shape, e. g., oval. This change of the cross-section back into the second shape may be triggered or effected or brought about by the particular material, set-up or the like of the retracting device holder 102. For example, it may have a shape-memory, a shape memory alloy, be made up from a weave, and the like.

The change of shape may be due an elastic deformation of the retracting device holder 102 or sections thereof taking place when the deploying device 103 is being retracted from the lumen of the retracting device holder 102.

The process of changing its cross-section shape from the first shape (e. g., circular) to the second shape (e. g., oval) can optionally begin immediately after or while pulling back the deploying device 103 from the retracting device holder 102.

Preferably the length $D_N$ of the oval shape corresponds to the, more or less, complete retracting and/or spreading distance of the aperture 302 in order to close with clamps the aperture 302 in a following step. For this purpose, the cross-sectional shape of the closing device holder 802 is preferably similar to the second, e. g., oval, shape the retracting device holder 102 assumes once it has been separated from the retracting device holder 102, a state that is shown in FIG. 46C. This following step will be described in detail with respect to FIG. 47 below.

FIG. 46D shows an optional design of the distal end section of the retracting device holder 102. Two grooves 139, which are open to the distal end and parallel to the longitudinal axis L, are located at the distal end section in order to receive the first arm 135 and the second arm 137 of the retracting device 101. The grooves 139 are positioned opposite to each other which means with an angle of 180 degrees related to the circumference of the retracting device holder 102. These grooves 139 can advantageously incorporate the two arms 135, 137 for easily pushing the retracting unit 100, comprising the retracting device holder 102 and the retracting device 101, forward through the tissue up to the aperture 302.

FIG. 46E shows parts of a further exemplary embodiment of the retracting device 101. The arms 135, 137 are truncated compared to the embodiment shown in FIG. 47B. The arms 135, 137 are integral parts of the distal end section of the retracting device holder 102.

In some embodiments there are no arms at all. The distal end section of the retracting device holder 102 may, for example, comprise a shape with two notches and two tooth-like peaks. The peaks can act as retractors when the cross-sectional shape of the retracting device holder 102 is elastically or otherwise adapted to the oval cross-sectional shape of the closing device holder 802.

FIG. 47 is a schematic perspective view of an additional exemplary embodiment of the closing device holder 802 and the retracting device 101.

Figures 47A, 47B, 47C:
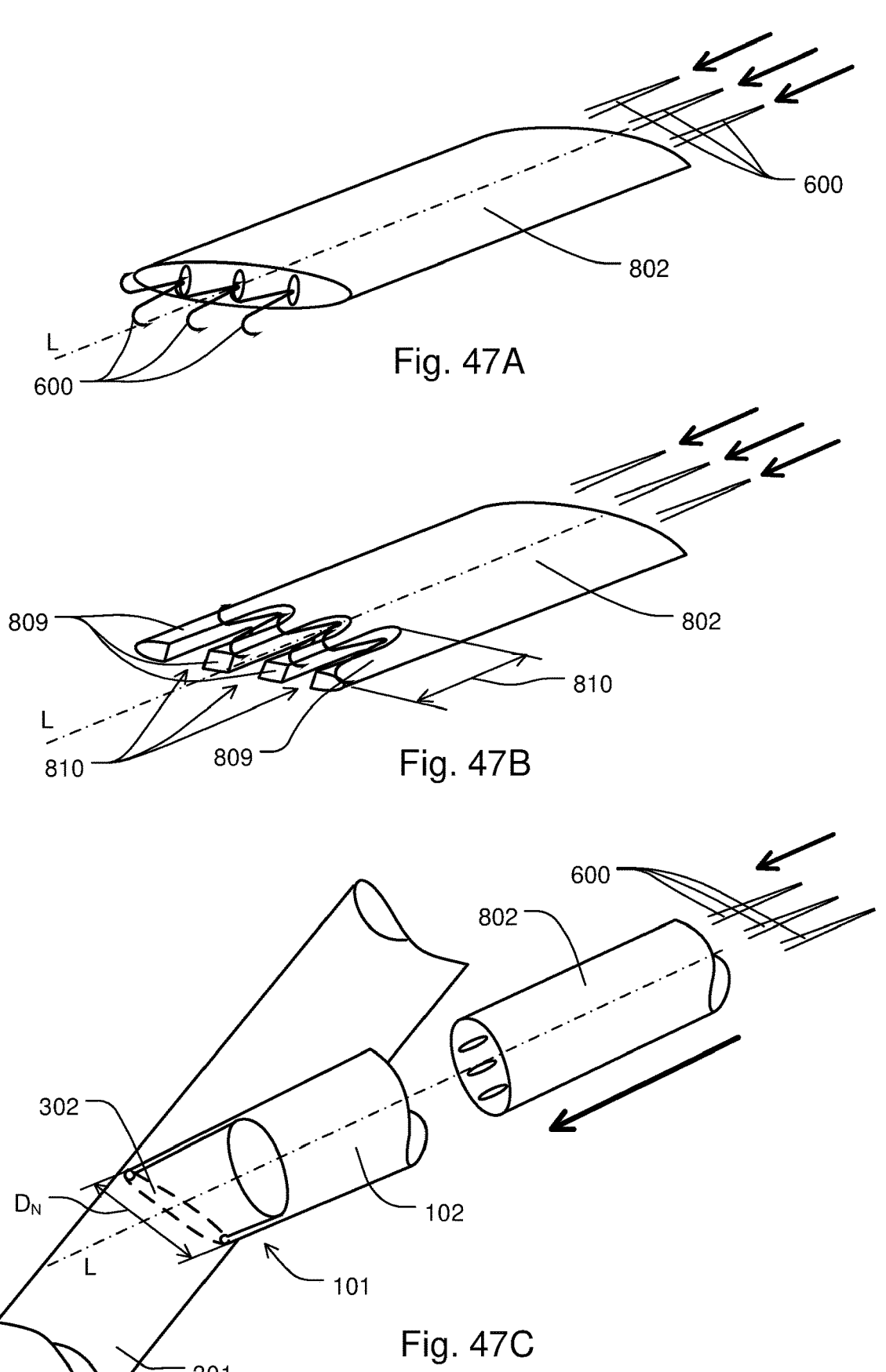
FIG. 47A to 47C show additional exemplary embodiments of closing device holders for the retracting device shown in FIG. 46C.

FIG. 47A shows an additional exemplary embodiment of the closing device holder 802. The optional oval cross-sectional shape of the closing device holder 802 is designed to fit into the oval cross-sectional shape of the retracting device 101 shown in FIG. 46C and/or FIG. 47C. This means that this exemplary embodiment of the closing device holder 802 can be inserted and/or pushed into the inner retracting device 101 only after pulling out the retracting device holder 102 from the retracting device 101, as shown in FIG. 46C. This feature is advantageous for a user of the medical apparatus because the first step which includes the sliding out of the retracting unit 100, shown in FIG. 46A, up to the aperture 302, is not possible with the closing device holder 802 instead of the retracting device holder 102. A mix-up is excluded for safety reasons.

The closing device holder 802 shown in FIG. 47A is an exemplary embodiment with three parallel guides for closing devices 600. The design of the closing devices 600 with two arms bending sidewise at the exit of the distal end of the closing device holder 802 is optional, other designs are possible.

FIG. 47B shows another exemplary embodiment of the closing device holder 802. The design of the distal end of the closing device holder 802 can be configured individually, depending on the need in each case for applying (the) closing devices 600 accordingly on the aperture 302.

The exemplary embodiment of the closing device holder 802 shown in FIG. 47B comprises several bars 809 with grooves 810 arranged between them. At the base of the grooves 810 are located openings for releasing closing devices 600. While closing apertures 302 of a vessel 301 by means of the closing devices 600 as it is shown in FIG. 47C (in which the elliptical shape of the cross section is not as narrow at its smallest diameter than the shape shown in FIG. 47 A), the bars 809 act as spacers for avoiding contact between the openings for releasing closing devices 600 and the wall of the vessel opposite to the aperture 302. Therefore, due to the bars 809, the closing devices 600 might not damage the vessel at its side opposite to the aperture 302. The length 810 of the bars 809 can be chosen in relation to the type or size of the vessel 301 to be treated using the medical apparatus.

FIG. 47C shows the medical apparatus comprising the additional exemplary embodiments of the closing device holder 802, shown in FIG. 47A, and the retracting device 101, shown in FIG. 46C, in order for closing an aperture 302 of a vessel 301.

Figure 48A:
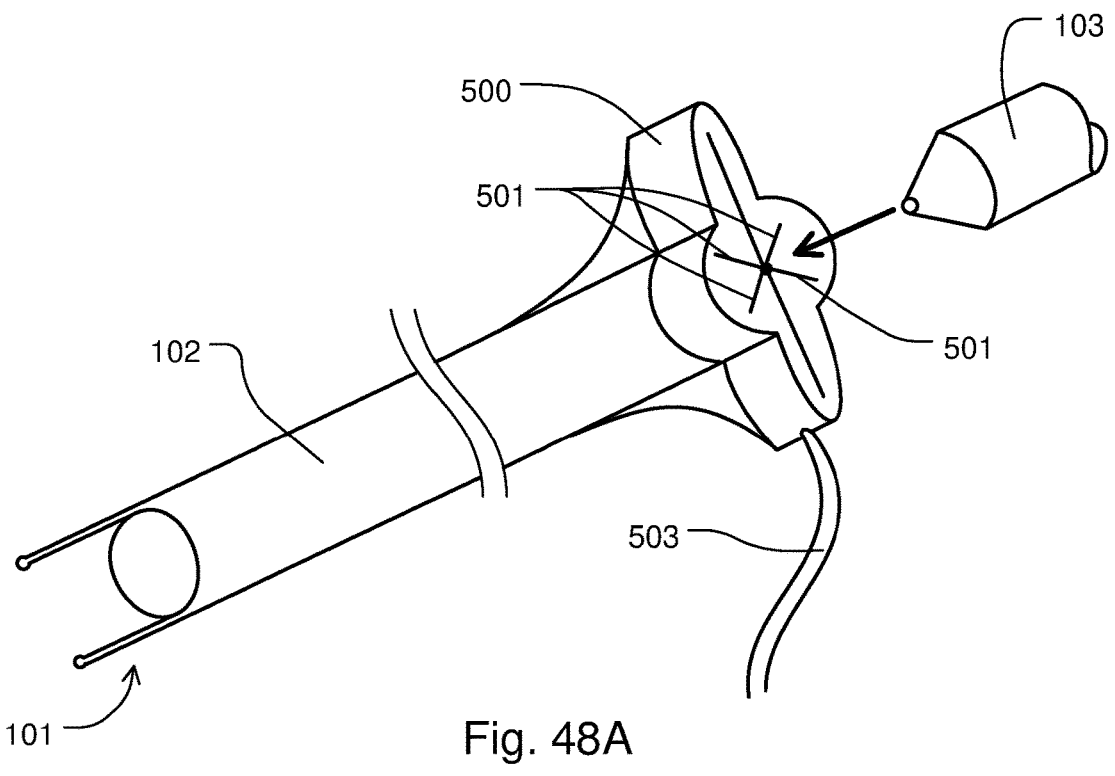
FIG. 48A, 48B show a connector with openings for the retracting device holder and the closing device holder.
Figure 48B:
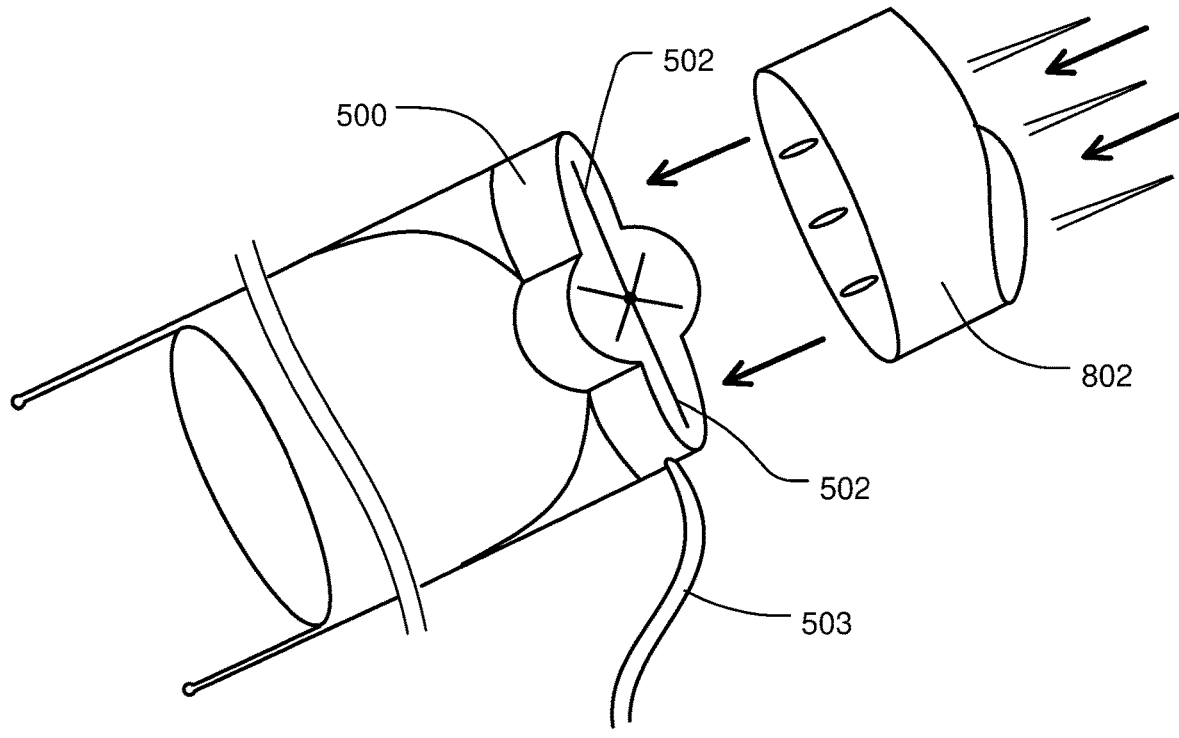

FIG. 48A, 48B show a connector 500 with openings 501, 502 to be consecutively penetrated first by the deploying device 103 and then by the closing device holder 802.

The connector 500 preferably is or comprises a hemostasis valve, for avoiding blood leakage once the medical apparatus or a part of the medical apparatus has been introduced into the body of a patient.

The connector 500 is preferably positioned at the proximal end of the retracting device holder 102.

The connector 500 is preferably designed integrally with the retracting device holder 102 and/or preferably attached to the retracting device holder 102 in a non-releasable manner.

The one or more materials of the connector 500 and the retracting device holder 102, or parts of them, can be the same, or different from each other. Exemplarily, the materials can be or comprise plastic.

The connector 500 is preferably an introducer sheath, e. g., for introducing the deploying device 103 and/or the closing device holder 802 into the retracting device holder 102.

The connector 500 can comprise one or more openings, preferably at its proximal end, sealing lips 501, 502 and/or the like. The openings and/or sealing lips 501, 502 can be designed as a passive valve for avoiding leakage of fluids, preferable of blood.

The opening(s) and/or sealing lips 501, 502 are preferably designed to be penetrated by the deploying device 103 and/or the closing device holder 802. A sealing function can preferably be maintained after the deploying device 103 and/or the closing device holder 802 has been retracted from the opening. In other words, the openings or sealing lips 501, 502 are preferably to provide a sealing function in a state when neither the deploying device 103 nor the closing device holder 802 has penetrated the sealing lips 501, 502 or advanced through the opening, as well as in a state after the deploying device 103 or the closing device holder 802 has been introduced.

Preferably the sealing lips 501, 502, (or) at least parts of them, fit closely to parts of the outer surfaces of the deploying device 103 and/or the closing device holder 802, once these have been introduced into the inner lumen of the retracting device holder 102, for sealing the proximal end of the retracting device holder 102 against blood leakage.

The opening (or parts of it) of the connector 500 or its opening area can have a first shape, e. g., a circular shape, for receiving the, preferably circular shaped, deploying device 103. The sealing lips 501 may be designed to form a seal with the outer surface of devices having the first, particularly circularly shaped, cross section. The openings and/or sealing lips 501 can be designed as slits or from slits. Preferably, at least four to six slits, which can be star-shaped, are part of the circular shape. The angle between the slits is preferably 45, 60 or 90 degrees.

At the same time, the opening (or parts of it) of the connector 500 or its opening area can have a second shape, e. g., an oval shape, for receiving the, preferably oval shaped, closing device holder 802. The oval shape opening may be covered or closed by sealing lips 502 designed to form a seal with the outer surface of oval shaped devices. The openings and/or sealing lips 502 can be designed as slits. Preferably at least one slit, which can be oriented to the length of the oval shape, is part of the circular shape.

Hence, the connector 500 may allow both a device having a round cross section and a device having an oval cross section to be introduced into the connector 500 and/or into the retracting device holder 102. Also, its lips 501, 502, or membranes, may provide a seal with the outer surface of the device irrespective of whether the device's cross section is round or oval.

The connector 500 preferably comprises a port for connecting a flush line 503. The flush line 503 can be an integral part of the connector 500. The flush line 503 can be used for de-gassing the connector 500 and/or for administering drugs and/or fluids to the patient. The flush line 503 can be designated as a sheath flush line 503.

Figures 49, 49A:
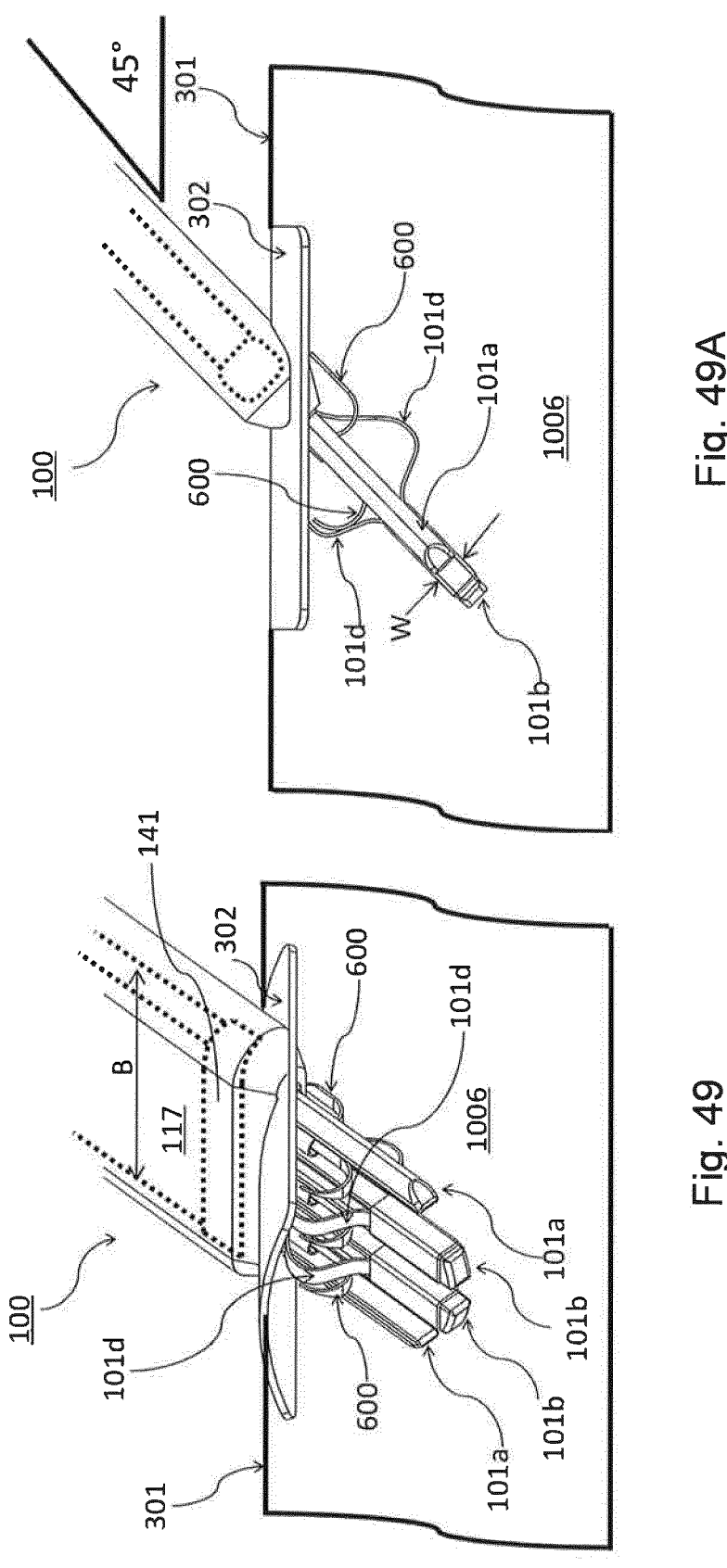
FIG. 49 shows parts of the medical apparatus according to another embodiment of the present invention in a perspective view.
FIG. 49A shows the medical apparatus of FIG. 49 substantially from its side.

FIG. 49 shows parts of the medical apparatus according to the present invention in another embodiment in a perspective view. Parts of the medical apparatus are introduced into the lumen 1006 of the vessel 301 through the aperture 302.

A number of arms 101*a*, 101*b* (four in this exemplary embodiment, a higher or smaller number of arms could be provided in other embodiments) are provided to act as retraction unit 100 or as part thereof. Upon advancing the arms 101*a*, 101*b* into the aperture 302 they retract the aperture 302 into a slit as is indicated in FIG. 49. In FIG. 49, the arms 101*a*, 101*b* are shown in their advanced position in which they extend out of the casing 117 of the retracting unit 100.

In the present embodiment, some or all of the arms 101*a*, 101*b* are provided in a line or in a common plane, or in contact with or crossed by a common plane. This way, they may allow the aperture 302 to expand into a slit shape while the arms 101*a*, 101*b* themselves may still be easy to be retracted from the slit as the retraction unit 100 still is quite flat or knife-shaped.

In some particular embodiments, the lengths of the arms 101*a*, 101*b* are different from each other. Hence, two or more different lengths can be provided for the arms. As can be seen in FIG. 49, the outer arms 101*a* are shorter than the inner arms 101*b* which are arranged between the outer one (or they are extended or protruded from the retracting unit 100 or a common sheath or casing 117 thereof by a greater length than the outer ones), giving the group or the collective of arms a tapered or triangular shape in a plan view. It is noted that in an alternative embodiment, the longest or the most advanced arm among the arms 101*a*, 101*b* is not one of the inner arms 100*b* but could also, e.g., be any other one, e.g. one of the outer ones.

Hence, in some embodiments, the retraction unit 100 may comprise or consist of a number of arms. Some of the arms may differ in lengths or by the extent to which they may be advanced from the inner of the retraction unit 100 to an outside thereof.

Also, in certain embodiments, all or some of the arms 101*a*, 101*b* of the retraction unit 100 may be arranged to be advanced into an advanced position and retracted from the advanced position again without being bent. For example, the arms can be straight or longitudinal components which either cannot be bent during use or will always run in parallel to each other (or both). Hence, in some embodiments there is no form the arms would assume (due to shape memory features, for example) other than the form the arms have while not being advanced.

FIG. 49 also features some optional protectors 101*d* each of which is connected to an arm 101*a* or 101*b*, wherein one protector 101*d* or more protectors 101*d* can be connected to a particular, single arm 101*a* or 101*b*. For example, one arm 101*a*, 101*b* may be connected to one protector 101*d* on its upper face, another protector 101*d* on its lower face as is the case in the example of FIG. 49 (please refer to FIG. 49A for reference).

Some or all of the protectors 101*d* may comprise or consist of materials with shape memory characteristics. This way, or by means of any other mechanism suitable, they may assume a shape when the respective protector 101*d*—or an arm connected to it—is advanced and moved out of, e. g., the casing 117 of the retracting unit 100, that shape being different from the shape the protector 101*d* assumes while still being present within the inner of the casing 117. An optional constriction 141, clamp or bottle neck may assist in allowing or forcing the protector 101*d* to change between what is called an unfolded position or shape herein (shown in FIG. 49 and FIG. 49A) and a folded position or shape it assumes while still comprised within the casing 117 (that position or shape not being shown in FIG. 49).

The protectors 101d may be arranged to unfold in a direction that is preferably perpendicular (or also perpendicular) to the longitudinal axis of the retracting unit 100 or of the respective arm 101a, 101b.

The protectors 101d may be arranged to unfold in a direction that is preferably perpendicular (or also perpendicular) to the direction of the largest extension of the retracting unit 100 or of the respective arm 101a, 101b in a breadth B of the retraction unit 100 or its casing 117.

As can be seen from FIG. 49, the breadth B of the casing 117 (in a left-right-direction in FIG. 49) is larger than the width W (see FIG. 49A) thereof, rendering the casing not round but rather flat, rectangular, elliptical or the like in cross section.

FIG. 49A shows the medical apparatus of FIG. 49 from its side while closing the aperture 302 by means of the three closing devices 600 shown in FIG. 49. From FIG. 49A the extent of the width W of the casing 117 can be derived.

In FIG. 49A, the retracting unit 100 is shown to be partly introduced into the aperture 302 by an exemplary angle of 45°.

The design of FIG. 49, which reveals a number of features all independent from each other, may allow for closing even large bores, both venous and arterial, effectively. Hemostasis may be achieved without leakage using only 3 or slightly more closing devices 600.

Figure 50A:
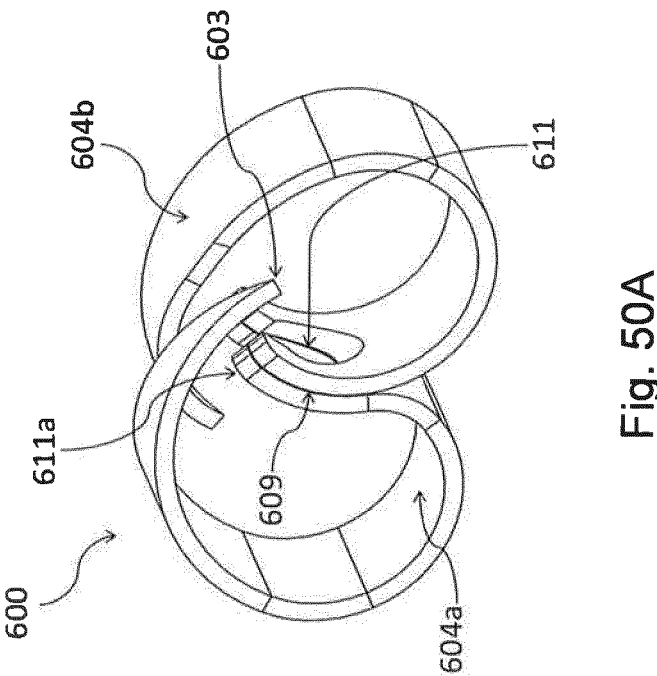
FIG. 50A shows the closing device of FIG. 50 in another perspective view.
Figure 50:
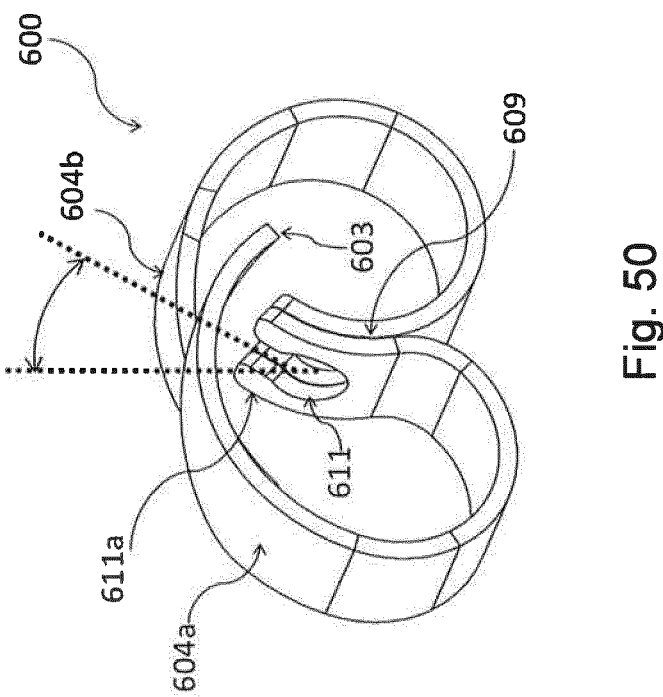
FIG. 50 shows a closing device in an embodiment in a perspective view.

The closing device 600 shown in FIG. 49 and FIG. 49A may be the one shown in FIGS. 50 and 50A. Alternatively, it may be any other closing device or any stapler known or described herein.

FIG. 50 shows a closing device 600 in yet another embodiment in a perspective view (from the right side). It comprises two arms 604a and 604b, each of which carries an optionally pointed end 603. The closing device 600 is shown in the curled position, a position the closing device 600 assumes while keeping the margins of the slit together (i.e., after having been released from the medical apparatus).

The arms 604a and 604b may either originate from a common curled or curved material or they may be attached one to the other in an attaching area 609 where they may be glued, welded or attached in any other way to each other.

As can be seen from FIG. 50 (please also refer to FIG. 50A), the shape of the closing device 600 is not symmetrical.

In the particular example of FIG. 50, the asymmetry of the closing device 600 is achieved by having inclined the optional attaching area 609 to the right. This asymmetry may be helpful when releasing the closing device 600 from the medical apparatus, e.g. using an optional pusher such as the pusher tube 808 as disclosed herein. The asymmetry, as well as the inclination of the attaching area 609 may be helpful in transmitting the force applied by the pusher when using the medical apparatus as shown in FIG. 49A (see the angle there). Also, the inclination may be helpful when inserting the medical apparatus or the retracting unit 100 into the tissue or the aperture 302: The medical apparatus may be inserted in, e. g., a 45° angle against the tissue surface (of advantage to the surgeon). The tips of the arms 604a and 604b may, however, still be perpendicular to the vessel wall upon entering the wall tissue.

Hence, the attaching area 609 may be inclined to a line perpendicular to the line of maximum breadth (in a left-right-direction in FIG. 50) by an angle between 20° and 60°, preferably between 30° to 50°.

As an optional feature, the attaching area 609 may comprise a through-opening 611. The through-opening 611 may have a closed circumference, or, as in FIG. 50, it may be open toward the circumference by means of an extension 611a of it. The extension may be narrower than the radius of the through-opening 611 itself. Hence, the extension may turn the overall-shape of the through-opening 611 into a key-hole-shape. The extension may be a bottle neck, in one plane, to the main area of the through-opening 611.

The wire of the arms 604a and 604b is preferably made from a flat wire or comprise a flat wire. A flat wire has, in contrast to a round wire, no round cross section. Its cross section is elliptical, rectangular or deviates in another way from a round design. Flat wire allows for higher grip force without surpassing for example nitinol's irreversible strain threshold. Also, it appears that the closing device 600 is able to hold a vessel wall with a relevant amount of perivascular tissue and cinch together to create hemostasis and full closure.

FIG. 50A shows the closing device 600 of FIG. 50 in another perspective view (from the left side).

Figures 51, 51A, 51B:
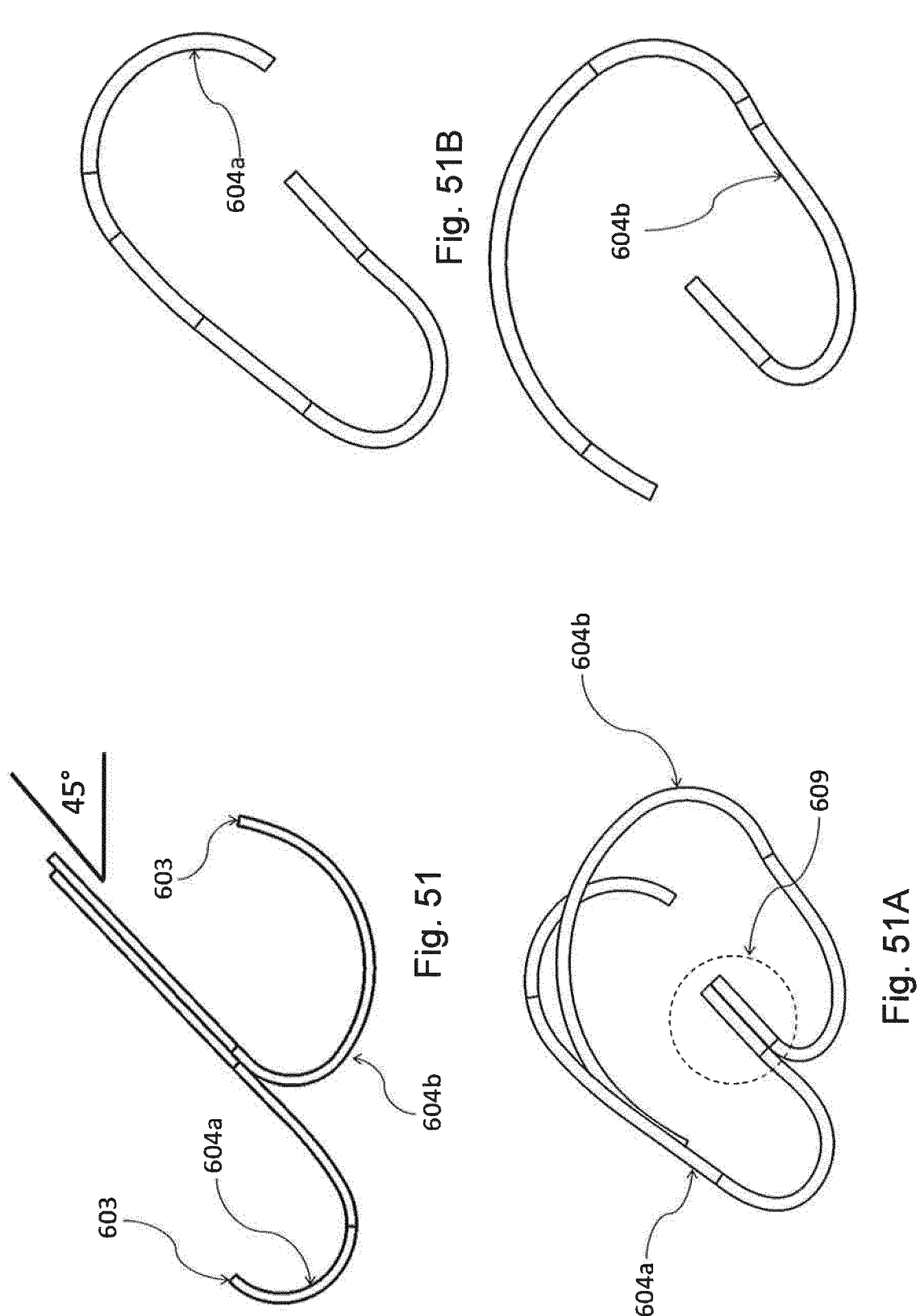
FIG. 51 shows a closing device according to the present invention in a first state.
FIG. 51A shows the closing device of FIG. 51 in a second state.
FIG. 51B shows the arms of the closing device of FIG. 51 detached from each other.

FIG. 51 shows a closing device 600 in a first state. The closing device 600 is according to an embodiment of the invention. It may be comprised by the medical apparatus according to the present invention. Also, it may be used in the method according to the present invention.

The closing device 600 comprises two arms 604a, 604b or consists thereof.

The closing device 600 is designed such that the tips 603 or distal ends of the arms 604a, 604b may, in one state where the closing device 600 is not fully deployed yet (as in FIG. 51) end in a plane that is inclined to the longitudinal direction of the proximal, and yet neighboring ends of the arms 604a, 604b as is shown in FIG. 51. The angle of that inclination may be between 20° and 60°, preferably it is about 45°.

FIG. 51A shows the closing device of FIG. 51 in a second state which may be the state the closing device 600 finally assumes for closing the aperture 302.

As can be seen in FIG. 51A, an attachment area 609 is provided at which the proximal ends or other parts of the arms 604a, 604b are attached to each other.

FIG. 51B shows the arms of the closing device of FIG. 51 detached from each other.

As can be seen from FIG. 51B, the asymmetry of the closing device 600 is the result of using two arms 604a, 604b of different shape when manufacturing the closing device 600.

The closing device 600 of FIGS. 51 to 51B may have each and every feature of any other closing device disclosed herein, in particular the features disclosed with respect to FIGS. 50 and 50A.

It will be appreciated by those skilled in the art that although the description is made to preferred embodiments, the disclosure and description in many respects, is only illustrative and not restrictive, susceptible to various modifications and alternative forms. Changes may be made in details, particularly in matters of shape, size, material and arrangement of parts without exceeding the scope of the invention. It should be understood, however, that the invention is not to be limited to the particular forms or methods disclosed, but to the contrary, the invention is to cover all modifications, equivalents and alternatives.

Accordingly, the scope of the invention is defined in the claims.

LIST OF REFERENCE NUMERALS 100 retracting unit
101 retracting device 101a arm
101b arm
101d protector
102 retracting device holder
103 deploying device
108 arrow
110 distal tip of retracting device holder, end, distal end
111 proximal end
112 distal end
115 guide wire lumen
117 casing
121 leg
123 leg
125 welding section
127 middle opening
131 opening
133 opening
135 first arm
137 second arm
139 groove
141 constriction
202 suture, holding device
203 piston
204 groove
207 groove
301 vessel, vessel wall, tissue
302 (vessel) aperture, slit opening, aperture opening
303 outside of a patient body
304 skin of a patient body
305 inside of a patient body
410 engaging device
420 curve, step
500 connector; hemostasis valve
501 opening, sealing lips, slit
502 opening, sealing lips, slit
503 flush line, sheath flush line
600 closing device
602 proximal end, junction, groove
603 distal end, pointed end, closing member, tip of the closing device, end of the closing device
604 arm
604a arm
604b arm
605 curled or curved section
607 non-curved or straight section
609 attaching area
611 through-opening
611a extension
708 anchor, anchor form of the closing device
709 tip 603 penetrates the tissue wall
722 perforation of 603
800 closing member
801 longitudinal direction arrow, arrow indicating orientation of support/closing device holder
802 closing device holder
803 channel, lateral channel
804 distal end, closing device holder end
805 proximal end, closing device holder end
806 delivery support
807 bumper
808 pusher tube
809 bar (of the closing device holder)
810 groove (between the bars)
900 handle member
902 first slider
904 second slider
906 switch 908 opening of handle member
910 multilumen extrusion or opening
912 knob
914 sleeve
916 guide slot
916a first slot section
916b second slot section
916c turning point
1000 guide wire
1006 vessel lumen
1411 aperture wall, edge
1420 arrow
1421 upward movement
1422 angle
1722 protractor
2204 wall, aperture wall, long sides
2600 suture
2700 arrow
B breadth
L longitudinal axis
$D_R$ cross section diameter
$D_N$ main axis length
W width

The invention claimed is:

1. A medical apparatus for closing an aperture in a tissue of a patient, wherein the tissue defines at least part of a blood vessel or other body lumen, the medical apparatus comprising:

closing device holders, each for releasably receiving one or more closing devices, wherein each of the one or more closing devices comprises a staple or a clip made at least partly of a deformable shape memory alloy and/or having a self-expanding shape memory section within the closing device holders in a stressed state such that when the one or more closing devices is manipulated to exit a distal end of the respective closing device holder during use of the medical apparatus, the one or more closing devices releases its stress, or part of it; and a retracting unit configured to come into contact with opposite sides of the aperture and for retracting the opposite sides of the aperture and/or for spreading the aperture causing the aperture to change its shape into a slit, wherein a multitude of arms are provided to act as the retraction unit or as part thereof;

wherein the medical apparatus comprises one or more bars or other protrusions that are arranged between or adjacent to openings of the closing device holders for discharging the one or more closing devices, the one or more bars or other protrusions being arranged to protrude over an opening area of at least one of the openings, wherein the closing device holders and the multitude of arms of the retracting unit are configured to be inserted into the aperture such that the one or more closing devices, when received in the closing device holders, is deployable, from the distal end of the respective closing device holder, inside of the blood vessel or other body lumen so as to close the aperture from inside of the blood vessel or other body lumen.

2. The medical apparatus according to claim 1, the retracting unit comprising:

at least one retracting device holder; and
at least one retracting device, at least partially received in the at least one retracting device holder, wherein the at least one retracting device is at least partially releasably received in the at least one retracting device holder;

wherein the at least one retracting device is arranged in a moveable or slidable manner with respect to the at least one retracting device holder.

3. The medical apparatus according to claim 2, comprising a deploying device configured to be at least partially releasably received in a lumen of the at least one retracting device holder.

4. The medical apparatus according to claim 3, wherein the at least one retracting device holder or its lumen exhibits, assumes or shows a first shape or a first cross section being a circular cross-section with a cross section diameter ($D_R$), while positioning the retracting unit into the aperture, and a second shape or a second cross section being an oval cross section with a main axis length ($D_N$) larger than the cross section diameter ($D_R$) and being an elliptical cross section with two symmetry axes, main axis and minor axis, after pulling the deploying device, partly or completely, out of the at least one retracting device holder.

5. The medical apparatus according to claim 4, wherein a shape of one of the closing device holders or of its cross section assumes mainly the second shape or features the second cross section, corresponds to it and/or has an oval cross section.

6. The medical apparatus according to claim 3, wherein one of the closing device holders is, at least partially releasably, received in the at least one retracting device holder, and translationally movable in a longitudinal direction of one of the closing device holders.

7. The medical apparatus according to claim 2, wherein the at least one retracting device is positioned at the distal tip, distal end or distal end section of the at least one retracting device holder, wherein the at least one retracting device and the at least one retracting device holder are designed integrally with each other and/or connected to each other in a non-releasable manner.

8. The medical apparatus according to claim 7, wherein the at least one retracting device comprises the multitude of arms that comprises or consists of a first arm and a second arm, the first arm and the second arm being positioned or provided parallel to each other at least while or before positioning the retracting unit into the aperture.

9. The medical apparatus according to claim 8, wherein the first arm and the second arm are arranged at the surface of a deploying device and/or in contact with it while advancing the at least one retracting device to the aperture, and wherein the first arm and the second arm are expanded, in a passive manner and/or without using a motor, manual assistance and/or a mechanism, to a retracting state for retracting the aperture after pulling the deploying device out from the at least one retracting device holder.

10. The medical apparatus according to claim 2, comprising a connector to be connected, or an integral part of, the at least one retracting device holder, providing an opening for advancing a deploying device and/or one of the closing device holders into an inner lumen of the at least one retracting device holder.

11. The medical apparatus according to claim 10, wherein at least one of the inner lumen of the at least one retracting device holder, or of a cross section thereof, and the opening area of the opening comprise sections that both delimit an at least partially round shape and sections that delimit an at least partially oval shape.

12. The medical apparatus according to claim 1, the retracting unit comprising at least a retracting device having at least one of:

a first side and an opposite second side, the multitude of arms comprising or consisting of a first arm and a second arm, a first retracting device and a second retracting device, a first retracting device holder and a second retracting device holder and a first engaging device and a second engaging device; and a mechanism for moving the first side apart or away from the second side, the first arm apart or away from the second arm, the first retracting device apart or away from the second retracting device, the first retracting device holder apart or away from the second retracting device holder and/or the first engaging device apart or away from the second engaging device.

13. The medical apparatus according to claim 1, wherein the closing device holders are arranged to remain, at least in parts, parallel to each other throughout the closing of the aperture or to part or deviate from each other when being advanced towards the aperture and/or out of a closing member.

14. The medical apparatus according to claim 1, wherein a delivery support for assuring—or assisting in—that the closing device holders deviate or part from each other when being advanced towards the aperture and/or out of a closing member is provided.

15. The medical apparatus according to claim 1, wherein at the outer or lateral sides of a closing member, of the closing device holders or of delivery support bumpers or spacers are arranged.

16. The medical apparatus according to claim 1, comprising a handle member, wherein the handle member comprises a sleeve or another element having a guide slot.

17. The medical apparatus according to claim 16, wherein the handle member, a knob or the sleeve itself comprises an elastic element or a spring arranged to guide a pin through a turning point of the guide slot.

18. The medical apparatus according to claim 1, wherein at least one of the multitude of arms comprises two legs surrounding or circumscribing at least one opening or middle opening between them.

19. The medical apparatus according to claim 1, wherein at least one opening of the retracting unit through which at least one of the multitude of arms exit in use of the medical apparatus has a width that is smaller than its length.

20. The medical apparatus according to claim 19, wherein at least one of the at least one opening of the retracting unit through which the at least one of the multitude of arms exits has an oval opening area or cross section.

21. The medical apparatus according to claim 1, comprising:

the one or more closing devices including a closing device comprised in one of the closing device holders.

22. The medical apparatus according to claim 21, wherein the closing device has two arms, wherein at least one of the arms has a or one first bending direction and a or one second bending direction.

23. The medical apparatus according to claim 22, wherein in a closed state of the closing device or the aperture, the end or tip of a first one of the arms points away from a second one of the arms, whereas the end or tip of the second arm points away from the first arm.

24. A method for closing an aperture of a tissue, encompassing the steps:

providing a medical apparatus according to claim 1, comprising a retracting device holder, a retracting device comprising the multitude of arms comprising or consisting of a first arm and a second arm, and a deploying device, wherein the retracting device is positioned at the distal tip, end or end section of the retracting device holder or attached to the latter;

inserting the deploying device into a lumen of the retracting device holder;

pushing forward both the deploying device and the retracting device holder comprising the retracting device up to the aperture until at least parts of the first arm and the second arm are positioned inside the aperture;

pulling the deploying device back and out of the lumen of the retracting device holder;

inserting one of the closing device holders having the one or more closing devices into the lumen of the retracting device holder, so that the distal opening or openings of one of the closing device holders for discharging the one or more closing devices from one of the closing device holders is/are positioned at the aperture;

pushing out, releasing or bringing out the one or more closing devices for closing the aperture.

25. A method for closing an aperture of a tissue, encompassing the steps:

providing a medical apparatus according to claim 1;

closing the aperture by means of the medical apparatus.

* * * * *